(12) United States Patent
Sone et al.

(10) Patent No.: US 9,746,037 B2
(45) Date of Patent: Aug. 29, 2017

(54) LINK ACTUATING DEVICE

(71) Applicant: NTN CORPORATION, Osaka (JP)

(72) Inventors: Keisuke Sone, Iwata (JP); Hirokazu Ooba, Iwata (JP); Arito Matsui, Iwata (JP); Hiroki Mukai, Iwata (JP)

(73) Assignee: NTN CORPORATION, Osaka (JP)

( * ) Notice: Subject to any disclaimer, the term of this patent is extended or adjusted under 35 U.S.C. 154(b) by 267 days.

(21) Appl. No.: 14/346,536

(22) PCT Filed: Sep. 24, 2012

(86) PCT No.: PCT/JP2012/074350
§ 371 (c)(1),
(2) Date: Mar. 21, 2014

(87) PCT Pub. No.: WO2013/047414
PCT Pub. Date: Apr. 4, 2013

(65) Prior Publication Data
US 2014/0227023 A1 Aug. 14, 2014

(30) Foreign Application Priority Data

Sep. 29, 2011 (JP) ................................ 2011-215082
Sep. 29, 2011 (JP) ................................ 2011-215083
(Continued)

(51) Int. Cl.
*B25J 17/00* (2006.01)
*B25J 17/02* (2006.01)
(Continued)

(52) U.S. Cl.
CPC .................. *F16D 3/30* (2013.01); *A61F 5/01* (2013.01); *F16H 21/54* (2013.01);
(Continued)

(58) Field of Classification Search
CPC .... B25J 9/0048; B25J 17/0266; B25J 9/0051; B25J 9/0087; B25J 9/0006; B25J 18/005;
(Continued)

(56) References Cited

U.S. PATENT DOCUMENTS 125,880 A * 4/1872 Clemens .................. F16D 3/20
464/106
5,472,412 A 12/1995 Knoth
(Continued)

FOREIGN PATENT DOCUMENTS

CN 1878640 12/2006
CN 101541483 9/2009
(Continued)

OTHER PUBLICATIONS

Extended European Search Report dated Aug. 6, 2015 in corresponding European Patent Application No. 12835921.3.
(Continued)

*Primary Examiner* — William Kelleher
*Assistant Examiner* — Jake Cook

(57) ABSTRACT

A link actuating device includes input side and output side link hubs, and two sets of link mechanisms. Each of the link mechanisms is a three-link-chain link mechanism including four revolute pairs, and includes input side and output side end links rotatably connected to the input side and output side link hubs and an intermediate links rotatably connected to input side and output side end links. The link mechanism have a positional relationship in which the revolute pair axes between the link hubs and the end links are located on the same plane and cross each other. At least one of the two sets of link mechanisms is provided with interlocking unit that interlocks the input side end link and the output side end link to each other so as to be rotationally displaced.

37 Claims, 39 Drawing Sheets

(30) Foreign Application Priority Data

| Nov. 2, 2011 | (JP) | 2011-241070 |
|---|---|---|
| Nov. 2, 2011 | (JP) | 2011-241071 |
| Aug. 24, 2012 | (JP) | 2012-184747 |

(51) Int. Cl.

| B25J 18/00 | (2006.01) |
|---|---|
| F16D 3/30 | (2006.01) |
| F16H 21/54 | (2006.01) |
| F16M 11/12 | (2006.01) |
| F16M 11/18 | (2006.01) |
| F16M 13/00 | (2006.01) |
| A61F 5/01 | (2006.01) |

(52) U.S. Cl.
CPC ........... *F16M 11/121* (2013.01); *F16M 11/18* (2013.01); *F16M 13/00* (2013.01); *Y10T 403/36* (2015.01)

(58) Field of Classification Search
CPC .... B25J 17/0275; B25J 9/1623; A61F 5/0123; A61F 2005/0134; A61F 2005/0139; A61F 2005/0144; A61F 2005/0155; A61F 2005/0137; A61F 2005/0141; F16D 3/30
See application file for complete search history.

(56) References Cited

U.S. PATENT DOCUMENTS

| 6,001,075 | A | 12/1999 | Clemens et al. | |
|---|---|---|---|---|
| 8,109,171 | B2 | 2/2012 | Nakao et al. | |
| 8,132,481 | B2 | 3/2012 | Nishida et al. | |
| 2005/0159075 | A1* | 7/2005 | Isobe | B25J 17/0266 446/104 |
| 2005/0199085 | A1 | 9/2005 | Isobe et al. | |
| 2008/0028881 | A1 | 2/2008 | Sone et al. | |
| 2008/0310945 | A1 | 12/2008 | Tsujita et al. | |
| 2009/0255363 | A1 | 10/2009 | Nishida et al. | |
| 2009/0255364 | A1 | 10/2009 | Nishida et al. | |
| 2010/0037721 | A1 | 2/2010 | Nakao et al. | |
| 2010/0043577 | A1* | 2/2010 | Rosheim | B25J 17/0266 74/5.4 |

FOREIGN PATENT DOCUMENTS

| CN | 101554727 | 10/2009 |
|---|---|---|
| CN | 101554731 | 10/2009 |
| JP | 06-337625 | 12/1994 |
| JP | 08-011080 | 1/1996 |
| JP | 09-154900 | 6/1997 |
| JP | 10-288811 | 10/1998 |
| JP | 11-109502 | 4/1999 |
| JP | 2004-009276 | 1/2004 |
| JP | 2005-069462 | 3/2005 |
| JP | 2005-230099 | 9/2005 |
| JP | 2005-299828 | 10/2005 |
| JP | 2007-114370 | 5/2007 |
| JP | 2007-275482 | 10/2007 |
| JP | 2008-307310 | 12/2008 |
| JP | 2012-66323 | 4/2012 |

OTHER PUBLICATIONS

Chinese Office Action dated Dec. 2, 2015 in corresponding Chinese Patent Application No. 201280047520.7.
PCT International Preliminary Report on Patentability and Written Opinion of the International Searching Authority mailed Apr. 10, 2014 in corresponding International Patent Application No. PCT/JP2012/074350.
PCT International Preliminary Report on Patentability and Written Opinion of the International Searching Authority mailed Apr. 15, 2014 in corresponding International Patent Application No. PCT/JP2012/074350.
International Search report mailed on Dec. 25, 2012 in corresponding International Application No. PCT/JP2012/074350.
Japanese Decision of Grant dated Aug. 4, 2015 in corresponding Japanese Patent Application No. 2011-241071.

* cited by examiner

——— TORQUE ACTING ON LINK MECHANISM 4A
------ TORQUE ACTING ON LINK MECHANISM 4B

Time(sec)

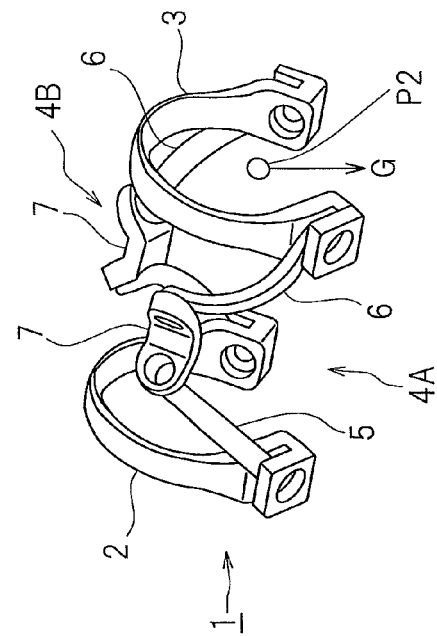
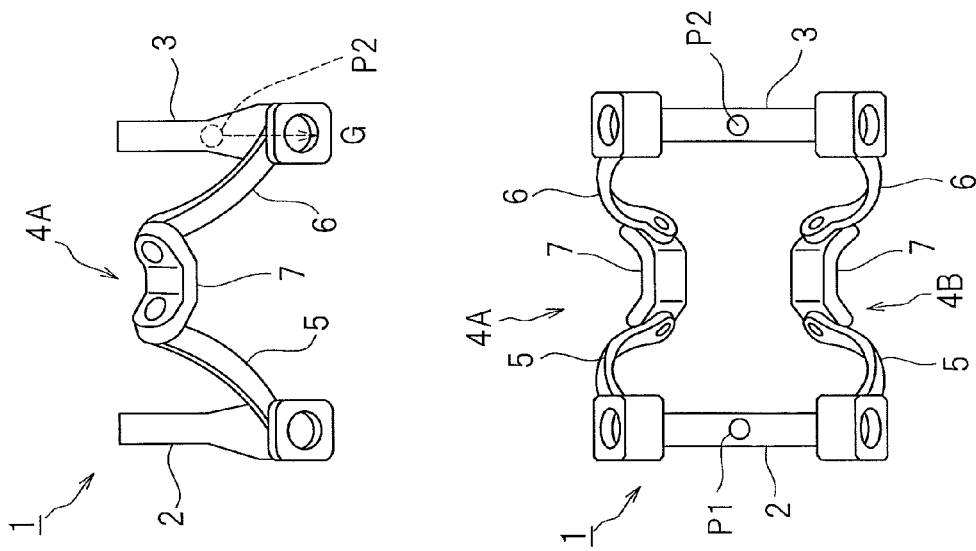
Fig. 6A
Fig. 6B
Fig. 6C

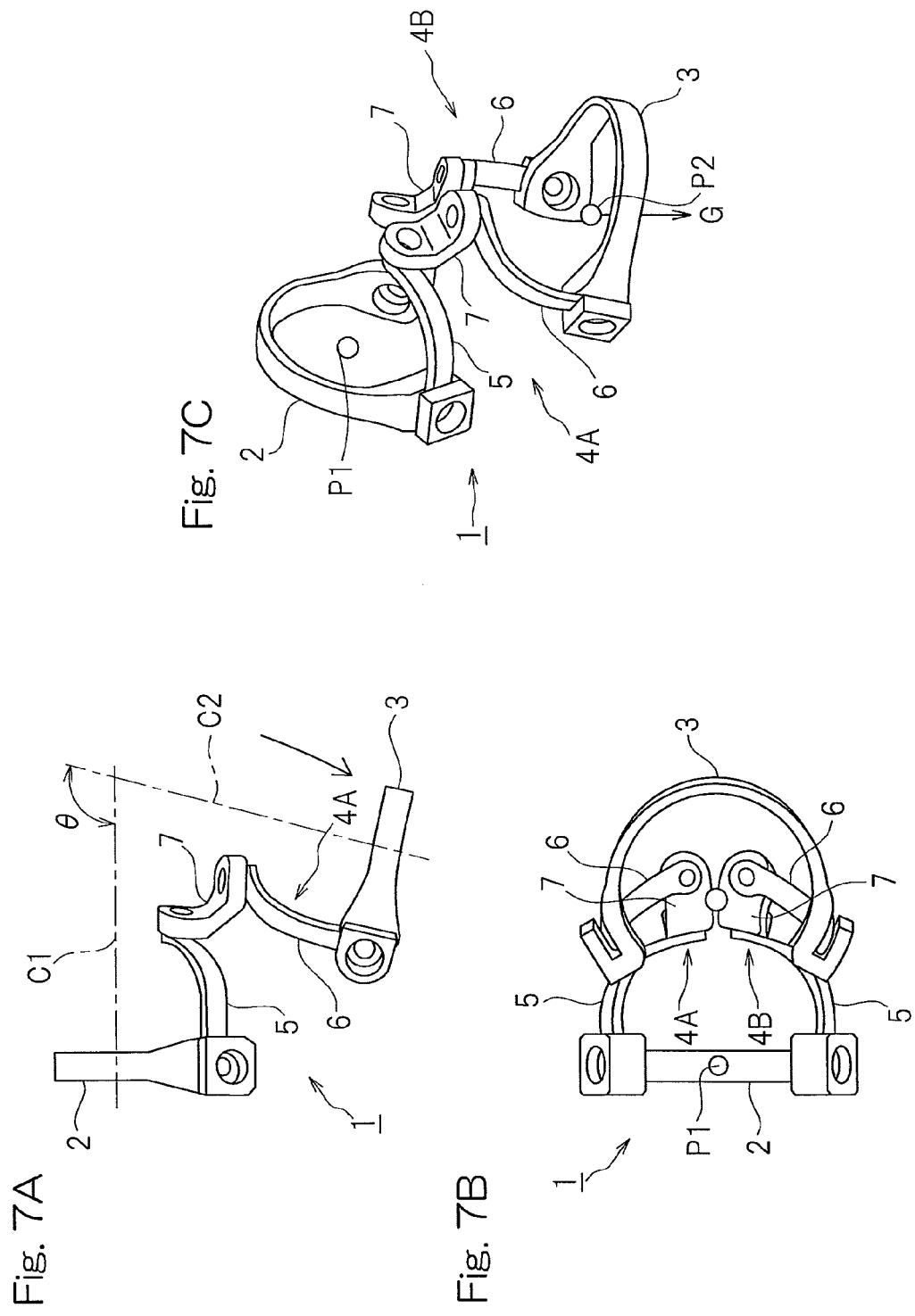

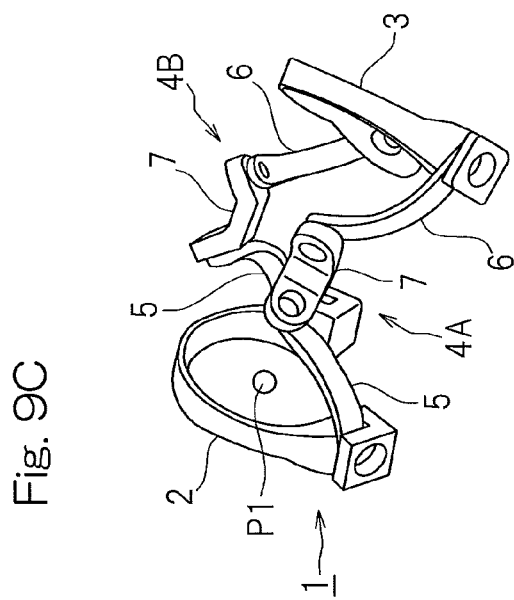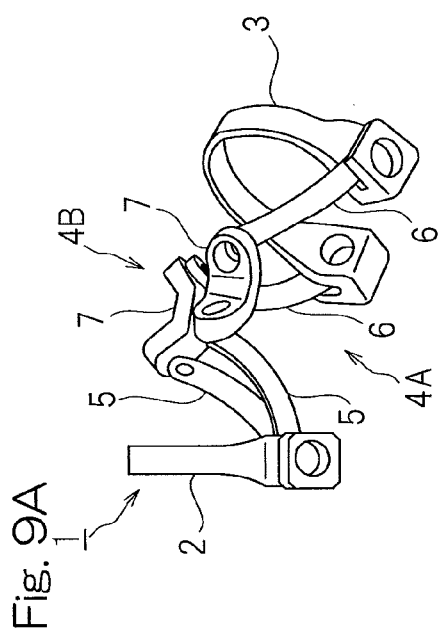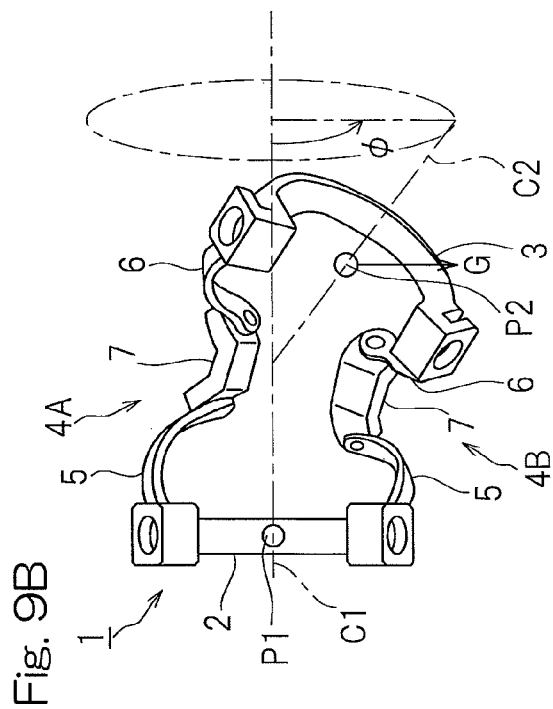

PRIOR ART

LINK ACTUATING DEVICE

CROSS REFERENCE TO THE RELATED APPLICATION

This application is based on and claims Convention priority to Japanese Patent Application Nos. 2011-215082 and 2011-215083, filed on Sep. 29, 2011, Japanese Patent Application Nos. 2011-241070 and 2011-241071, filed on Nov. 2, 2011, and Japanese Patent Application No. 2012-184747, filed on Aug. 24, 2012, the entire disclosure of which is herein incorporated by reference as a part of this application.

BACKGROUND OF THE INVENTION

Field of the Invention

The present invention relates to a link actuating device for a robot joint portion, an industrial machine and the like that is used for speedily and precisely performing operations, such as handling of articles and complex processing, in a three-dimensional space over a wide range. Particularly, the invention relates to a link actuating device that is suitable for, in the medical field, being mounted around a human joint portion for use in assisting the recovery of the function of the joint and the movement thereof, and a platform that includes a link actuating device of this kind and supports an optical device such as a camera so that the angle of the optical device can be changed in at least two directions.

Description of Related Art

As the above-described link actuating device, there have been proposed configurations in which an input side link hub and an output side link hub are connected by a three-link-chain link mechanism including four revolute pairs so as to permit the attitude of the output side link hub to be changed relative to the input side link hub (e.g., Patent Documents 1 and 2). The three-link-chain link mechanism composed of the four revolute pairs includes input side and output side end links rotatably connected to the input side and output side link hubs, respectively, and an intermediate link rotatably connected to the input side and output side end links. Patent Document 1 discloses an example in which, in a geometric model obtained by representing a link mechanism by straight lines, the portion on the input side and the portion on the output side relative to the central portion of the intermediate link have shapes that are mirror symmetrical, and an example in which they have shapes that are point symmetrical. Patent Document 2 discloses an example in which the portion on the input side and the portion on the output side have shapes that are point symmetrical.

Conventional link actuating devices, including Patent Documents 1 and 2 described above, have three sets of link mechanisms. The reason for this is that, in the case of forming the link mechanism by only links, the minimum number of link mechanisms required to define the attitude of the output side link hub relative to the input side link hub is three.

Furthermore, some link actuating devices are mounted around a human limb joint portion for the purposes of the assistance of movements, including passive movement of bending and stretching of a joint portion and walking or the like, for the angle correction around the affected area as a result of a limb fracture and the function recovery. For example, Patent Document 3 discloses a device that controls CPM devices used in the medical field, and the device controls one degree of freedom of the CPM devices. All the conventional CPM devices described in Patent Document 3 have one degree of freedom in the bending angle direction of the joint portion. Patent Document 4 discloses a mounted type assisting device that is mounted to the side surface of a leg to assist the movement of the leg, and the device assists only bending and stretching movements of the leg.

In addition, platforms including a link actuating device of this type are proposed in Patent Documents 5, 6, and 7, for example. Patent Document 5 proposes a two-degree-of-freedom platform capable of changing the angle of an optical device such as a camera in two directions, namely, a tilt direction (vertical rotational direction) and a pan direction (horizontal rotational direction). Patent Document 6 proposes a three-degree-of-freedom platform capable of changing the angle of the optical device also in an inclined direction, in addition to the tilt direction (vertical rotational direction) and the pan direction (horizontal rotational direction). Patent Document 7 proposes a three-degree-of-freedom platform having a structure constituted by one spherical pair.

PRIOR ART DOCUMENT

[Patent Document 1] JP Patent No. 4476603
[Patent Document 2] JP Laid-open Patent Publication No. 2004-009276
[Patent Document 3] JP Patent No. 3638048
[Patent Document 4] JP Patent No. 4178185
[Patent Document 5] JP Patent No. 4250164
[Patent Document 6] JP Patent No. 3568375
[Patent Document 7] JP Patent No. 3212535

When the number of sets of link mechanisms of a link actuating device is three, link mechanisms 204 (204A, 204B, and 204C) are disposed at intervals of substantially 120° as shown in FIG. 45. In this case, the mutual distance between the respective link mechanisms 204 is small, so that a revolute pair portion 212 between a link hub 203 and an end link 206 in one link mechanism 204A, and a revolute pair portion 214 between an end link 206 and an intermediate link 207 in another link mechanism 204B are brought close to each other. Therefore, in order to prevent the two revolute pair portions 212 and 214 from interfering with each other, the revolute pair portion 214 is provided toward the outer diameter. This results in a problem that the overall outer diameter of the link actuating device 201 is increased. The outer diameter is further increased when the link hubs 202 and 203 are formed to have a hollow shape, and an air tube, an electric wire or the like is passed through the inside thereof.

Furthermore, when the number of sets of the link mechanisms is three, it is difficult to assemble the link mechanisms 204 while appropriately maintaining the mutual angles of the central axes of rotation of the revolute pair portions 211, 212, 213, and 214. Moreover, the larger the number of the link mechanisms 204, the higher the cost.

When the number of sets of the link mechanisms 204 is three, inconveniences will arise depending on the application as described above. Therefore, the applicant made an attempt to develop a link actuating device capable of defining the attitude of the output side link hub relative to the input side link hub even when the number of sets of the link mechanisms 204 is two. However, simply decreasing the number of sets of the link mechanisms 204 to two results in a reduction in the overall rigidity as compared with a link actuating device having three sets of link mechanisms.

Further, the link actuating device having the three-link-chain link mechanisms 204 includes the output side link hub capable of movement with two degrees of freedom in the rotational direction relative to the input side link hub, and therefore it can be used in the medical field, for example, by being mounted around a human joint portion for the recovery of the joint function and the movement assistance. However, the link actuating device having three link mechanisms 204 has a small mutual distance between the respective link mechanisms 204, and therefore it is difficult to insert a joint portion between the input side and output side link hubs. Moreover, when the link actuating device is mounted around a human joint portion, a part of one of the three link mechanisms 204 inevitably comes into contact with the patient body. Accordingly, it has been practically difficult for the link actuating device to be mounted around a human joint portion for use.

Further, the above-described limb joint portion mounted apparatus has one degree of freedom in the direction of bending angle of the joint portion. However, a human limb joint is not limited to one degree of freedom in the direction of bending direction, and is capable of complex movement. For example, the knee joint is capable of making torsional movement relative to the length direction of the lower limb, in addition to bending and stretching in the front-back direction. Also, the shoulder joint is capable of making a substantially 360° turning movement. That is to say, the human limb joint makes movement with two or more degrees of freedom.

Accordingly, with a limb joint portion mounted apparatus only capable of making angular movement with one degree of freedom, the angular adjustment in another one-degree-of-freedom direction cannot be made, and therefore, it is difficult to perform angle correction. Furthermore, in rehabilitation, when the limb joint portion mounted apparatus has one degree of freedom of movement, the muscles used and the movable portion within the joint are limited. This makes it necessary to remount the limb joint portion mounted apparatus in a different orientation and repeat the movement assistance. As described above, when sufficient measures cannot be provided by the conventional limb joint portion mounted apparatuses, rehabilitation works have to rely on physiotherapists. In that case, there will be the problems of time constraints and higher costs of treatment. Since the directions of movements are limited in assisting movements such as walking, free movement cannot be achieved. For the reasons described above, there is a need for a limb joint portion mounted apparatus capable of two degrees of freedom of rotation.

In the case of using the link actuating device 201 as a limb joint portion mounted apparatus, the link hubs 202 and 203 are formed to have a hollow shape, a limb joint portion is placed between the pair of link hubs 202 and 203, and the limb joint portion mounted apparatus is mounted around the limb joint portion with an area continuous with the limb joint portion being inserted in the hollow portions 220. To allow insertion of the area continuous with the limb joint portion into the hollow portions 220, it is necessary to widen the hollow portions 220, resulting in a further increase in the outer diameter. When the overall outer diameter of the link actuating device 201 is large, in the above-described mounted state, a part of the link actuating device 201 may collide with an area other than the limb joint portion or an object in the surroundings, resulting in a hazardous situation. Furthermore, to facilitate the insertion of the area continuous with the limb joint portion into the hollow portions 220, the hollow portions 220 may have a shape that is open to the outside of the device. However, the open portions cannot be sufficiently widened because the three sets of link devices 204 are arranged in the circumferential direction.

Since the platforms disclosed in Patent Documents 5 and 6 includes the revolute pair in the tilt direction and the revolute pair in the pan direction disposed in serial with each other, overall weight balance is rendered to be poor, and therefore, it is difficult to be maintain the platforms in a fixed attitude (e.g., horizontal attitude) in a self-supporting manner. If these platforms were to be self-supported in a fixed attitude, they need to be each provided with a large and heavy base portion. In general, a base body (Patent Document 5) or a connecting member (Patent Document 6) serving as the base portion is fixed to a tripod, and this tripod is used to perform the attitude adjustment (e.g., leveling) for the platform. The attitude adjustment is performed by separately changing the angles of the legs of the tripod, and this adjustment operation is complex and troublesome. Accordingly, it takes time to perform the positioning of the optical device.

The platform disclosed in Patent Document 7 has one common center of rotation in three directions, and it is therefore difficult to achieve a weight balance. Consequently, it is also necessary to provide a large and heavy base portion in order to allow the platform to be self-supported in a fixed attitude. This platform can simultaneously undergo the angular changes in three directions. Thus, in the case of fixing a pedestal serving as the base portion to the tripod, it is possible to perform the positioning of the optical device without fixing the attitude of the pedestal at, for example, a level, in advance. Accordingly, the positioning operation of the optical device can be performed easily and in a short period of time. However, the spherical pair structure poses a drawback in that the operating angle range is narrow and the optical device cannot be positioned in a wide range.

SUMMARY OF THE INVENTION

It is an object of the present invention to provide a link actuating device that has a compact configuration with a small outer diameter, is easy to assemble, and can be produced at a low cost.

It is another object of the invention to provide a link actuating device that has high rigidity, while it can be composed of two sets of link mechanisms and has a compact configuration with a small outer diameter.

It is yet another object of the invention to provide a link actuating device that has a compact configuration with a small outer diameter and that can easily prevent contact between objects to be, for example, restrained, supported, or guided and link mechanisms.

It is still another object of the invention to provide a limb joint mounted apparatus that is capable of two degrees of freedom of rotation, has a compact configuration with a small outer diameter, and can be easily mounted around a limb joint portion.

Furthermore, it is still yet another object of the invention to provide a platform whose angle can be changed in at least two directions, that has a wide range of operating angles and enables a simple angle changing operation.

A link actuating device according to the present invention includes input side and output side link hubs; input side and output side end links to be rotatably connected to the input side and output side link hubs, respectively; an intermediate link to be rotatably connected to the input side and output side end links; and a three-link-chain link mechanism including four revolute pairs composed of the input side end link, the intermediate link and the output side end link. In the link actuating device, two sets of the three-link-chain link mechanisms including the four revolute pairs are provided, and the four revolute pairs have a first revolute pair axis between the input side link hub and the input side end link, a second revolute pair axis between the output side link hub and the output side end link, a third revolute pair axis between the input side end link and the intermediate link, a fourth revolute pair axis between the output side end link and the intermediate link. In such case, the two sets of link mechanisms have a positional relationship in which, on both the input side and the output side, the respective first revolute pair axes of the two sets of link mechanisms are located on the same plane and cross each other. In such case, at least one of the two sets of link mechanisms is provided with interlocking unit that interlocks the input side end link and the output side end link to each other so as to be rotationally displaced. A term "revolute pair axis" as used herein means a central axis of rotation of a revolute pair.

In this structure, the input side and output side link hubs and the input side and output side end links respectively connected thereto constitute spherical surface link mechanisms, and in each of the spherical surface link mechanisms, the input side and output side end links are connected via the intermediate links. Here, the two intermediate links of each of the link mechanisms have one degree of freedom that is limited to translation movement on the circumference of a circle with which each of the spherical surface link mechanisms overlaps. Assuming that the radius of curvature of a link is infinite, the spherical surface link mechanisms on the input side and the output side constitute a four-link mechanism on a plane and the input side and the output side each independently have one degree of freedom. When there is no interlocking unit between the input side and output side end links, the link actuating device has three degrees of freedom, including one degree of freedom of the two intermediate links and one degree of freedom of each of the input side and output side spherical surface link mechanisms. Here, the interlocking unit is provided between the input side and output side end links in the link actuating device. Accordingly, the respective spherical surface link mechanisms are interlocked, and the two spherical surface link mechanisms provide one degree of freedom. As described above, the link actuating device is a mechanism having a total of two degrees of freedom, including one degree of freedom of the intermediate links and one degree of freedom of the spherical surface link mechanisms. Note the positional displacement of the intermediate link is an angular change between the input side and output side link hubs, and accordingly, the link actuating device has a structure in which the angular change in two directions is possible between the input side and output side link hubs.

The two-degree-of-freedom mechanism can ensure a wide movable range for the output side link hub relative to the input side link hub. For example, a maximum bending angle between the central axis of the input side link hub and the central axis of the output side link hub can be 90° or more, so that it is possible to set the turning angle of the output side link hub relative to the input side link hub in the range of 0° to 360°. The central axis refers to an axis connecting the input side and output side link hub centers, the input side link hub center being a point of intersection between the first revolute pair axes of the two link mechanisms, the output side link hub center being a point of intersection between the second revolute pair axes of the two link mechanisms in a state in which the input side and output side link hubs are parallel to each other.

Since the link actuating device described above includes the interlocking unit, the attitude of the output side link hub relative to the input side link hub can be defined even if the number of sets of the link mechanism is two. Since the number of sets of the link mechanism is two, which is fewer than conventionally used three sets, the interference between the two link mechanisms can be more easily prevented, thus achieving a high degree of freedom in design. This enables the link actuating device to have a compact configuration with a small overall outer diameter. Furthermore, it is possible to achieve cost reduction due to the smaller number of the link mechanisms.

According to the present invention, the interlocking unit may interlock the input side end link and the output side end link such that rotational directions thereof relative to the intermediate link are opposite to each other and rotational displacement angles thereof are the same. In this case, at the time of changing the attitude of the output side link hub relative to the input side link hub, a plane that is located at an intermediate point between the centers of the input side and output side link hubs and is perpendicular to the straight line connecting the centers always coincides with a transverse cross section that is perpendicular to the direction of arrangement of the two revolute pairs between the intermediate link and each of the input side and output side end links. Accordingly, the input side and the output side move symmetrical with respect to the transverse cross section. Thus, the output side is displaced in the same manner as the displacement of the input side and there will be no displacement variation, resulting in good operability.

According to the present invention, it is preferable that geometric models obtained by respectively representing the two sets of link mechanisms by straight lines have the same shape. To be precise, the geometric model refers to a model obtained by representing the four revolute pairs and the straight line connecting between these revolute pairs. In this case, the link mechanism that does not have the interlocking unit makes the same movement as the link mechanism that has the interlocking unit. This facilitates the control of the rotational angle performed by the interlocking unit. Furthermore, when the two sets of link mechanisms have the same shape, it is possible to reduce the number of types of parts, thus achieving cost reduction.

According to the present invention, geometric models obtained by respectively representing the two sets of link mechanisms by straight lines may have shapes in which an input side portion and an output side portion relative to a central portion of the intermediate link are minor symmetrical to each other. In this case, the input side end link and the output side end link have the same movable range in the circumferential direction, and therefore the region, in which the input side and output side end links and the intermediate links do not enter, is rendered to be large in the space between the input side link hub and the output side link hub. This makes it possible to place an article into the space from the region in which these links do not enter. In this region, other articles may be brought closer to the link actuating device, and therefore this device will be compact when it is mounted to a robot, an industrial machine, or the like. Furthermore, at the time of attaching an assembly of the intermediate link and the input side and output side end links to the input side and output side link hubs, the circumferential positions of the revolute pair axes of the attachment portions coincide with each other on the input side and the output side, and it is therefore possible to attach the assembly from one direction, thus improving the ease of assembly.

According to the present invention, it is preferable that the intermediate link of each of the two sets of link mechanisms is located on a side on which an angle between the first revolute pair axes of the two link mechanisms is greater than 180°. In this case, the revolute pair portions of the link hub and the end links of one link mechanism are prevented from interfering with the revolute pair portions of the end links and the intermediate links of the other link mechanism. This eliminates the need to provide the revolute pair portions of the end links and the intermediate link so as to protrude in the outer diameter direction to avoid the above-described interference, and it is thus possible to achieve a compact configuration with a small outer diameter.

According to the present invention, it is preferable that the link actuating device further includes rolling bearings that rotatably support the input side and output side end links relative to the input side and output side link hub, respectively, in which case, each of the input side and output side link hubs is provided with a bearing enclosing portion enclosing an outer ring of the corresponding rolling bearing. By providing the rolling bearing so as to be accommodated in the link hub in this way, it is possible to simplify the revolute pair portion between the link hub and the end link. Thereby, the revolute pair portions do not protrude toward the outer diameter and thus can be made compact.

According to the present invention, the input side and output side link hubs respectively may include input side and output side hollow portions each of which penetrates through in a direction parallel to an axis connecting input side and output side link hub centers, the input side and output side link hub centers being a point of intersection between the first revolute pair axes of the two link mechanisms and a point of intersection between the second revolute pair axes of the two link mechanisms, respectively in a state in which the input side and output side link hubs are parallel to each other. In such case, the input side and output side hollow portions have a shape in communication with outside of the respective input side and output side link hubs via input side and output side opening portions, the input side opening portion being provided between the first revolute pair axes of the two link mechanisms, and the output side opening portion being provided between the second revolute pair axes of the two link mechanisms. In such case, the input side and output side opening portions are located on the same side with respect to the first and second revolute pair axes, respectively. In other words, in an attitude in which the input side link hub and the output side link hub are parallel to each other, the opening portions of the input side and output side link hubs are located on planes on the same side. Note that "state in which the input side and output side link hubs are parallel" means that the directions of reference planes of these link hubs are parallel. When the link hubs include the hollow portions, cables such as an electric wire and an air tube can be provided through the hollow portions, thereby preventing the cables from easily coming into contact with the links and anything other than the link actuating device. Furthermore, when the hollow portions in communication with the outside of the link hubs via the opening portions are provided, it is possible to place the cables in the hollow portions even if they are connected to devices during insertion of the cables through the hollow portions, thus improving the operability.

According to the present invention, the interlocking unit may be configured to interlock the input side and outside side end links to each other so as to be rotationally displaced by meshing between a gear provided in the input side end link and a gear provided in the output side end link. When the interlocking unit is achieved by meshing between a plurality of gears, no error will occur in the rotational displacement of the input side end link and the output side end link due to, for example, sliding. Accordingly, they can be interlocked accurately.

According to the present invention, each of the two sets of link mechanisms may be provided with an actuator capable of arbitrarily changing a rotational angle of one of the four revolute pairs. By providing the actuator in the above-described location, it is possible to control the movements of the two sets of link mechanisms to arbitrarily change the attitude of the output side link hub relative to the input side link hub. When the actuator is provided so as to change the rotational angle between the revolute pair between the input side link hub and the output side end link on the stationary side (for example, the input side), it is possible to reduce the load weight of the output side link hub on the movable side (for example, the output side), resulting in an increase in the weight capacity of the output side link hub. Furthermore, inertial force at the time of operating the link actuating device is reduced, thus facilitating the attitude control for the output side link hub.

According to the present invention, each of the two sets of link mechanisms may be provided with an extendable linear actuator whose opposite ends are connected directly or indirectly to two link mechanism components that include the input side and output side links or the input side and output side link hubs.

When the linear actuator is extended or contracted, the relative angle or position between the two link mechanism components to which opposite ends of the linear actuator are connected is changed. Accordingly, the aforementioned relative angle or position is determined by controlling the amount of extension/contraction of the linear actuator, and thereby, the attitude of the output side link hub relative to the input side link hub is also determined. By providing the linear actuator, a link configuration is achieved that is closed by a plurality of link mechanism components including the two link mechanism components and the linear actuator, and the force acting between the two link mechanism components is received by the linear actuator. Accordingly, the rigidity of the link actuating device is improved.

According to the present invention, the opposite ends of the extendable linear actuator may be directly or indirectly connected to the input side or output side link hub and the input side or output side end link connected to the corresponding link hub. Since the link hub and the end link is connected by one revolute pair, by providing the linear actuator between the link hub and the end link, the connecting portion between the link hub and the linear actuator and the connecting portion between the end link and the linear actuator can both constitute revolute pair. In other words, two-dimensional pairs can be realizes. Accordingly, a bearing such as a deep groove ball bearing can be used for the connecting portions, and it is therefore possible to reduce the cost and the rotational resistance as compared with the use of a spherical pair or a cross joint. Additionally, there is no limitation on the rotational angle in the case of using a bearing such as a deep groove ball bearing, and therefore the degree of freedom in design increases.

When the extendable linear actuator includes an outer cylinder body and an advancing or retracting shaft that is located inside the outer cylinder body and advances or retracts relative to the outer cylinder body, the outer cylinder body may be fixed to the input side or output side link hub and the advancing or retracting shaft is connected to the input side or output side end link via an auxiliary link that adjusts a positional relationship between the advancing or retracting shaft and the input side or output side end link in response to advancement or retraction of the advancing or retracting shaft. When the outer cylinder body of the linear actuator and the advancing or retracting shaft are compared, the outer cylinder body has a larger diameter and a larger weight than the advancing or retracting shaft. By fixing the heavier outer cylinder body to the link hub serving as the fixed side, it is possible to reduce the weight of the movable portion, thereby improving the responsiveness to the driving of the linear actuator. Furthermore, since the moving portion of the linear actuator can be made compact, it is possible to make the linear actuator less prone to interference with the other members of the link actuating device or articles other than the link actuating device.

According to the present invention, the opposite ends of the extendable linear actuator may be directly or indirectly connected to the input side or output side link hub and the intermediate link. In this case, the link actuating device has a link configuration that is closed by the link hub, the end link, the intermediate link, and the linear actuator, and therefore the rigidity is improved. The link hub and the intermediate link relatively move in three dimensions, and therefore connecting portion between the link hub and the linear actuator and the connecting portion between the intermediate link and the linear actuator both constitute spherical pairs. Thereby, the rigidity is also improved as a result of decrease in the number of chains that are provided only by serial connection.

According to the present invention, the opposite ends of the linear actuator may be directly or indirectly connected to the input side end link and the output side end link. In this case, the link actuating device has a link configuration that is closed by the input side end link, the intermediate link, the output side end link and the linear actuator, and therefore the rigidity is improved. The input side end link and the output side end link move, for example, in a mirror-symmetrical manner, and therefore do not assume twisted positions. On the other hand, the inclination of arbitrary surface of the end link changes in two directions relative to a linear axis of the linear actuator, and therefore, the connecting portion between the input side end link and the linear actuator and the connecting portion between the output side end link and the linear actuator both constitute cross joint couplings. Consequently, the number of chains that are provided only by serial connection is reduced, which also improves the rigidity.

According to the present invention, one of the two sets of link mechanisms may be provided with two or more actuators that are capable of arbitrarily changing rotational angles of the revolute pairs or that change a relative distance between two of a plurality of link mechanism components that include the input side and output side end links or the input side and output side link hubs. The link mechanism that is provided with the interlocking unit and the link mechanism that is provided with the actuator may be the same or different. Additionally, at least two of the two or more actuators are installed at positions at which the input side and the output side relative to the central portion of the intermediate link are not symmetrical.

With this configuration, the interlocking unit is provided between the input side and output side end links in addition to spherical surface link mechanisms on the input side and the output side. Thereby, for each of the two sets of link mechanisms, the positions of the input side and output side link hubs and the input side and output side end links relative to the central portion of the intermediate link are determined simultaneously. Accordingly, even if the two actuators are disposed in positions that are symmetrical to the central portion of the intermediate link, the position control is performed with only one degree of freedom, leaving one degree of freedom unused. Accordingly, in order to perform the positional control with two degrees of freedom, it is necessary to dispose the actuators at positions that are not symmetrical to the central portion of the intermediate link.

By providing the two or more actuators that are capable of arbitrarily changing the rotational angles of the revolute pairs of the link mechanism or that change the relative distance between the two link mechanism components, it is possible to arbitrarily change the attitude of the output side link hub relative to the input side link hub with two degrees of freedom in the rotational direction. Since the two or more actuators are provided in one of the two sets of link mechanisms, the actuators and the components therearound are concentrated on the side of the link mechanism in which the actuators are provided. Accordingly, in the case where the link actuating device is used for, for example, restraining, supporting, or guiding an object, for example, in the case where the link actuating device is mounted around a human joint portion, the link mechanisms can be prevented from coming into contact with the patient body or the like by mounting the link actuating device such that the side of the link mechanism in which the actuators are provided is positioned away from the restrained object such as the body. Furthermore, since the number of sets of link mechanisms is two, it is possible to ensure a relatively large circumferential range in which no portion of the two sets of link mechanisms is located regardless of the attitude of the output side link hub relative to the input side link hub. Accordingly, the contact between the body and the link mechanisms can also be easily prevented.

According to the present invention, the two or more actuators may include a first actuator that changes a rotational angle of the first or second revolute pair and a second actuator that changes a rotational angle of the third or fourth revolute pair. The attitude of the output side link hub relative to the input side link hub can be arbitrarily changed with two degrees of freedom in the rotational direction by providing the two actuators in this way.

Furthermore, the two or more actuators may include a first actuator that changes a rotational angle of the first or second revolute pair and a second actuator that changes a relative distance between the input side or output side link hub and the intermediate link. The attitude of the output side link hub relative to the input side link hub can be arbitrarily changed with two degrees of freedom in the rotational direction also by providing the two actuators in this way. When the actuator that changes the relative distance between the link hub and the intermediate link is a linear actuator, a link configuration is achieved that is closed by the link hub, the end link the intermediate link, and the linear actuator, so that the load acting on the link mechanism is received by the linear actuator. Accordingly, the rigidity of the link actuating device is improved.

According to the present invention, the two or more actuators may include a first actuator that changes a rotational angle of the first or second revolute pair and a fourth actuator that changes a relative distance between the input side and output side end links. The attitude of the output side link hub relative to the input side link hub can be arbitrarily changed with two degrees of freedom in the rotational direction also by providing the two actuators in this way. When the actuator that changes the relative distance between the input side and output side end links is a linear actuator, a link configuration is achieved that is closed by the input side end link, the intermediate link, the output side end link and the linear actuator, so that the load acting on the link mechanism is received by the linear actuator. Accordingly, the rigidity of the link actuating device is improved.

A limb joint mounted apparatus according to the present invention includes any one of the above-described link actuating devices. In the limb joint portion mounted apparatus, the input side and output side link hubs respectively include input side and output side hollow portions each of which penetrates through in a direction parallel to an axis connecting input side and output side link hub centers, the input side and output side link hub centers being a point of intersection between the first revolute pair axes of the two link mechanisms and a point of intersection between the second revolute pair axes of the two link mechanisms, respectively in a state in which the input side and output side link hubs are parallel to each other. In such case, in a state in which a limb joint portion is located between the input side and output side link hubs and an area continuous with the limb joint portion is inserted in the input side and the output side hollow portion, the limb joint portion mounted apparatus may be mounted around the limb joint portion. Note that "state in which the input side and output side link hubs are parallel" means that the directions of reference planes of these link hubs are parallel. The reference planes are arbitrarily determined for the two link hubs in the same determining method, based on the shapes of the link hubs, the positions of the revolute pair portions of the link hubs and the two end links or the revolute pair axes thereof. For example, when both of the link hubs have flat shapes, planes perpendicular to the thickness direction may be determined as the reference planes, and the reference planes may be parallel to each other. Alternatively, planes in which the revolute pair axes of the link hubs and the two end links form a given same angle may be determined as reference planes, and the reference planes may be parallel to each other.

With this configuration, by connecting the input side and output side link hubs to each other by a three-link-chain link mechanism including four revolute pairs, the output side link hub can be rotated with two degrees of freedom relative to the input side link hub.

In order for the limb joint portion mounted apparatus to perform limited two degrees of freedom of rotation, the two sets of link mechanisms preferably have a positional relationship in which, on both the input side and the output side, revolute pair axes between each of the link hubs and the end links thereof are located on the same plane and cross each other. However, in a state in which the limb joint portion mounted apparatus is mounted around a limb joint portion as described below, the limb imposes a limit to the movement of the link mechanisms, and therefore, the limb joint portion mounted apparatus performs substantially limited two degrees of freedom of rotation. Thus, the link mechanisms may not have the above-described positional relationship.

In a state in which a human limb joint portion, which is the affected area, is located in the space between the input side and output side link hubs and an area continuous with the limb joint portion is inserted in the hollow portion of each of the link hubs, the limb joint portion mounted apparatus is mounted around the limb joint portion. In this mounted state, the angle of the limb joint portion can be adjusted by adjusting each of the rotational angles of the revolute pairs in the two sets of link mechanisms. Also, the aforementioned angle can be fixed by fixing the rotation of the revolute pairs of the link mechanisms. By adjusting or fixing the angle of the limb joint portion in this way, it is possible to cope with varying angular differences depending on the physical characteristics of the patient and the condition of the affected area. The input side and output side link hubs receive the load on both sides of the limb joint portion, and it is therefore possible to reduce the load on the limb joint portion.

With this configuration of the limb joint portion mounted apparatus, the number of sets of the link mechanism is two, and therefore, the interference between the link mechanisms can be more easily prevented, thus achieving a high degree of freedom in design. This enables the limb joint portion mounted apparatus to have a compact configuration with a small overall outer diameter. Since the overall outer diameter of the limb joint portion mounted apparatus does not increase so much even if the hollow portions of the link hubs are widened, it is possible to widen the hollow portions of the link hubs, thereby increasing the ease of mounting around the limb joint portion. Furthermore, it is possible to achieve cost reduction due to the smaller number of the link mechanisms.

According to the present invention, it is preferable to provide the interlocking unit that interlocks the input side end link and the output side end link such that rotational directions thereof relative to the intermediate link are opposite to each other and rotational displacement angles thereof are the same. In this structure, the input side and output side link hubs and the input side and output side end links respectively connected thereto constitute spherical surface link mechanisms, and in each of the spherical surface link mechanisms, the input side and output side end links are connected via the intermediate links. Here, the two intermediate links of each of the link mechanisms have one degree of freedom that is limited to translation movement on the circumference of a circle with which each of the spherical surface link mechanisms overlaps. Assuming that the radius of curvature of a link is infinite, the spherical surface link mechanisms on the input side and the output side constitute a four-link mechanism on a plane and the input side and the output side each independently have one degree of freedom. When there is no interlocking unit between the input side and output side end links, the link actuating device has three degrees of freedom, including one degree of freedom of the two intermediate links and one degree of freedom of each of the input side and output side spherical surface link mechanisms. Here, the interlocking unit is provided between the input side and output side end links in the link actuating device. Accordingly, the respective spherical surface link mechanisms are interlocked, and the two spherical surface link mechanisms provide one degree of freedom. As described above, the link actuating device is a mechanism having a total of two degrees of freedom, including one degree of freedom of the intermediate links and one degree of freedom of the spherical surface link mechanisms. Note the positional displacement of the intermediate link is an angular change between the input side and output side link hubs, and accordingly, the link actuating device has a structure in which the angular change in two directions is possible between the input side and output side link hubs.

With a mechanism having two degrees of freedom, the attitude of the output side link hub relative to the input side link hub can be determined by simply determining the rotational angle of the revolute pair in one location in at least one of the two sets of link mechanisms. Accordingly, the attitude of the output side link hub can be easily changed or fixed. In the case where the interlocking unit interlocks the input side end link and the output side end link such that rotational directions thereof relative to the intermediate link are opposite to each other and rotational displacement angles thereof are the same, at the time of changing the attitude of the output side link hub relative to the input side link hub, a plane that is located at an intermediate point between the centers of the input side and output side link hubs and is perpendicular to the straight line connecting the centers always coincides with a transverse cross section that is perpendicular to the direction of arrangement of the two revolute pairs between the intermediate link and each of the input side and output side end links. Accordingly, the input side and the output side move symmetrical with respect to the transverse cross section. Thus, the output side is displaced in the same manner as the displacement of the input side and there will be no displacement variation, resulting in good operability.

According to the present invention, it is preferable that each of the input side and output side link hubs is divided into two link hub halves arranged in a circumferential direction along an outer circumference of the input side and output side hollow portions, with the two link hub halves being coupled to each other by a coupling portion and the input side or output side end link of one of the two sets of link mechanisms is rotatably connected to each of the two link hub halves. By dividing each link hub into two link hub halves, the area continuous with the limb joint portion can be easily placed into the hollow portion of the link hub. Since the two link hub halves can be coupled to each other by the coupling portions, the limb joint portion mounted apparatus in a state in which the area continuous with the limb joint portion is placed into the hollow portion of the link hub can be mounted around the joint portion safely and easily.

Preferably, one of the coupling portions that are provided in two locations in the circumferential direction and that couple the two link hub halves to each other is configured to have a hinge structure that pivotably couples the two link hub halves to each other. In this case, it is possible to open and close the hollow portion by pivoting the two link hub halves relative to each other with the coupling portion having a hinge structure as the fulcrum. Accordingly, the area continuous with the limb joint portion can be more easily placed into and out of the hollow portion.

According to the present invention, at least one of the four revolute pairs in each of the link mechanisms may be provided with a limiter that limits relative rotation angular displacement of the at least one of the four revolute pairs. By limiting the relative rotation angular displacement of the revolute pair by the limiter, the movable range of the output side link hub relative to the input side link hub is limited. As a result, the movable range of the limb joint portion, to which the limb joint portion mounted apparatus is mounted, is also limited. By changing the settings of the limiter, the movable range can be easily adjusted according to the condition of the limb joint portion, which is the affected area.

According to the present invention, at least one of the four revolute pairs in each of the link mechanisms may be provided with a damper that elastically limits relative rotation angular displacement of the at least one of the four revolute pairs. When impact force is applied to the limb, load is abruptly applied to the limb in contact with the link hub. According to the above structure, since the load is reduced by the damper, it is possible to reduce the burden on the limb.

According to the present invention, it is preferable that each of the two sets of link mechanisms is provided with an actuator that permits relative rotation angular displacement of at least one of the four revolute pairs to be changed, and a controller that controls the actuator such that the limb joint portion is moved within a movable range is provided. In this case, by driving the actuators under control of the controller so as to forcibly change the attitude of the output side link hub relative to the input side link hub, it is possible to perform rehabilitation exercises in which the limb joint portion is moved within the movable range. Since the attitude of the output side link hub relative to the input side link hub can be changed with two degrees of freedom, it is possible to determine the initial position with respect to the mounting angle of the link hubs located in the vicinity of the joint portion, according to the condition of the joint portion of the patient. Furthermore, not only simple bending and stretching of the limb joint portion, but also twisting movement can be performed according to the condition of the patient. Accordingly, many muscles around the limb joint portion can be moved effectively, thus achieving effective rehabilitation exercises. As a result, the recuperative period can be shortened. Additionally, the burden on physiotherapists can be reduced.

According to the present invention, each of the two sets of link mechanisms may be provided with an actuator that permits relative rotation angular displacement of at least one of the four revolute pairs to be changed, and a controller that controls the actuator so as to assist movement of the limb joint portion within a movable range may be provided. In this case, it is possible to assist, for example, bending and stretching of the limb joint portion by driving the actuators under control of the controller so as to adjust the movable range and the movable speed of the output side link hub relative to the input side link hub. Since the attitude of the output side link hub relative to the input side link hub can be changed with two degrees of freedom, it is possible to assist torsional movement and turning movement, in addition to simple bending and stretching of the limb joint portion.

A platform according to the present invention includes a device mount to which an optical device is mounted; and any one of the above described link actuating device that supports the device mount such that an attitude of the device mount is changed. In the platform, the link actuating device includes: a proximal end side link hub constituted by the input side link hub installed on a fixed installation object; a distal end side link hub constituted by the output side link hub fixed to the device mount; proximal side and distal side end links to be rotatably connected to the proximal end side and distal end side link hubs, respectively; an intermediate link to be rotatably connected to the proximal side and distal side end links; and two sets of three-link-chain link mechanism each including four revolute pairs composed of the proximal side end link, the intermediate link and the distal side end link, in which case, the four revolute pairs has a first revolute pair axis between the proximal end side link hub and the proximal side end link, a second revolute pair axis between the distal end side link hub and the distal side end link, a third revolute pair axis between the proximal side end link and the intermediate link, a fourth revolute pair axis between the distal side end link and the intermediate link. In such case, the two sets of link mechanisms have a positional relationship in which, on both the input side and the output side, the respective first revolute pair axes of the two sets of link mechanisms are located on the same plane and cross each other, and at least one of the two sets of link mechanisms is provided with interlocking unit that interlocks the input side end link and the output side end link to each other so as to be rotationally displaced. In such case, for each of the two sets of link mechanisms, at least one of the four revolute pairs is provided with rotation limiting unit that limits relative rotation between the two link mechanism components constituting the at least one of the four revolute pairs.

In the link actuating device, the proximal end side and distal end side link hubs and the proximal side and distal side end links respectively connected thereto constitute spherical surface link mechanisms, and in each of the spherical surface link mechanisms, the proximal side and distal side end links are connected via the intermediate links. By achieving the positional relationship in which the first or second revolute pair axes of the two link mechanisms are located on the same plane and cross each other, the two intermediate links of each of the link mechanisms have one degree of freedom that is limited to translation movement on the circumference of a circle with which each of the spherical surface link mechanisms overlaps. Assuming that the radius of curvature of a link is infinite, the spherical surface link mechanisms on the proximal end side and the distal end side constitute a four-link mechanism on a plane and the proximal end side and the distal end side each independently have one degree of freedom.

When there is no interlocking unit between the proximal side and distal side end links, the link actuating device has three degrees of freedom, including one degree of freedom of the two intermediate links and one degree of freedom of each of the proximal end side and distal end side spherical surface link mechanisms. Since the interlocking unit is provided between the proximal side and distal side end links in the link actuating device, the respective spherical surface link mechanisms are interlocked, and the two spherical surface link mechanisms provide one degree of freedom.

As described above, the link actuating device is a mechanism having a total of two degrees of freedom, including one degree of freedom of the intermediate links and one degree of freedom of the spherical surface link mechanisms. Note the positional displacement of the intermediate link is an angular change between the proximal end side and distal end side link hubs, and accordingly, the link actuating device has a structure in which the angular change in two directions is possible between the proximal end side and distal end side link hubs.

For each of the two sets of link mechanisms, at least one of the four revolute pairs is provided with the rotation limiting unit. Thereby, it is possible to perform the angular change in two directions, while limiting this angle change operation in two directions. This makes it possible to position the distal end side link hub relative to the proximal end side link hub in arbitrary position and attitude.

In the platform, a device mount is supported by the above described link actuating device such that the attitude of the device mount can be changed, and an optical device is mounted to the device mount. Accordingly, the angle of the optical device can be changed in two directions, thus achieving a wide operating angle and simple angle changing operations.

Unlike the platforms disclosed in Patent Documents 5 and 6 in which the revolute pair in the tilt direction and the revolute pair in the pan direction are disposed in serial, this platform supports the device mount by the two sets of link mechanisms that are provided in parallel. Accordingly, the device mount can be supported in a stable manner, and it is possible to reduce the size and weight of the proximal end side link hubs serving as the basal portions. Thus, in addition to using the platform by being fixed to a tripod, the platform can be used while being placed on any base.

Furthermore, with this platform, the number of sets of the link mechanisms of the link actuating device is two, and therefore a wide opening can be provided in a circumferential portion of the link hubs as compared with, for example, the device including three sets of link mechanisms disclosed in Patent Document 4. A hand can be placed from the wide opening into the space portion between the two sets of link mechanisms, thus facilitating the operation of mounting the optical device to the device mount.

According to the present invention, the rotation limiting unit is, for example, the rotation limiting unit is grease that is sealed between rotatable opposed portions of the two link mechanism components that are opposed each other and are rotatably displaced relative to each other. By sealing grease between the rotatable opposed portions of the two link mechanism components, the relative rotation between the two link mechanism components is permitted, and at the same time, the relative rotation between the two link mechanism components is limited. Furthermore, rattling between the two link mechanism components is obviated owing to the viscous resistance of the grease, thereby preventing wobbling during the manual operation and improving operability.

When the two link mechanism components are rotatably connected each other via a rolling bearing at a location other than the rotatable opposed portions, the grease may be sealed inside the rolling bearing. In this case, the starting torque at the time of operating the link actuating device is reduced. Furthermore, the operation during the actuation is smooth, thus achieving good operability.

According to the present invention, when one of the two link mechanism components includes a shaft member that is concentric with the revolute pair axis, the other link mechanism component includes an opposed surface that opposes an end face of the shaft member contactlessly, the rotation limiting unit may include a contact element in contact with the opposed surface and a pressing spring member that is provided between the end face of the shaft member and the opposed surface and presses the contact element against the opposed surface. In this case, the relative rotation between the two link mechanism components is limited by the friction between the opposed surface and the contact element.

According to the present invention, it is preferable that the proximal end side link hub is installed with a central axis thereof facing in a vertical direction, and at least one of the proximal side end link, the intermediate link, the distal side end link, and the distal end side link hub is provided with a balance weight that achieves a weight balance among the link actuating device, the device mount, and the optical device mounted to the device mount. The provision of the balance weight makes it possible to reduce the moment acting on the revolute pair portions of the link actuating device due to the self-weight of the platform and the weight of the optical device. This makes it possible to reduce the load on the rotation limiting unit, thus simplifying the configuration of the rotation limiting unit.

According to the present invention, it is preferable that the proximal end side link hub is installed such that a link hub central axis thereof faces in a vertical direction, and a counter weight, which corresponds to an amount of moment around a link center of the optical device that is mounted to the device mount, is provided on a side opposite to a side of the optical device with respect to the link center. As used herein, the term "the link hub center" refers a point of intersection between the link hub central axis on the proximal end side and the link hub central axis on the distal end side when an angle is formed between the proximal end side link hub and the distal end side link hub. When the counter weight is provided, the moment acting on each of the revolute pair portions can be kept suppressed low even if the weight balance is changed due to the operation of the link actuating device.

According to the present invention, between the two link mechanism components of the three-link-chain link mechanism including the four revolute pairs, a biasing spring member that biases the two link mechanism components so as to form a predetermined angle together may be provided. By properly adjusting the angle between the link mechanism components of the revolute pair by the spring force of the biasing spring member, the inclination of the distal end side link hub due to the weight of the optical device is corrected. This makes it possible to reduce the moment acting on the revolute pair portions.

When the biasing spring member is a torsion spring that is provided around the revolute pair axis between the two link mechanism components, one end of the torsion spring being fixed to one of the two link mechanism components and the other end thereof being fixed to the other of the link mechanism component, the biasing spring member can be installed in a compact manner.

According to the present invention, when $\alpha$ represents an angle between the first or second revolute pair axes of the two link mechanisms, $\beta$ represents an inter-axis angle between the first and third revolute pair axes or an inter-axis angle between the second and fourth revolute pair axes, and $\gamma$ represents an inter-axis angle between the third and fourth revolute pair axes, it is preferable that $\alpha+2\beta+\gamma=360°$ is satisfied. If the above relationship is satisfied, then the link actuating device can laid out flat. This improves the ease of storage and carrying of the platform.

According to the present invention, the proximal end side link hub and the fixed installation object may be connected by a revolute pair that is rotatable about the proximal end side link hub central axis, or the distal end side link hub and the device mount may be connected by a revolute pair that is rotatable about the distal end side link hub central axis. Thereby, in addition to the above described angular change in two directions, it is possible to perform the angular change about the link hub central axis on the proximal end side or the distal end side, thus achieving a configuration that can perform the angular change in a total of three directions. Accordingly, it is possible to perform the positioning in the pan direction (horizontal rotational direction) for the optical device, in addition to leveling and the positioning in the tilt direction (vertical rotational direction).

According to the present invention, it is preferable that the optical device is mounted to the device mount such that the distal end side link hub central axis and an optical axis of the optical device coincide or extend parallel to each other. In this case, the positioning of the optical axis in the tilt direction (vertical rotational direction) and the pan direction (horizontal rotational direction) can be performed by the operation of positioning the distal end side link hub relative to the proximal end side link hub of the link actuating device. Accordingly, the optical axis can be linearly moved at the time of positioning the optical axis, thus speeding up the operation.

Furthermore, it is preferable that the optical device is mounted to the device mount such that at least a part of the optical device is disposed in a space portion between the two sets of link mechanisms. In this case, the optical device can be mounted to the platform in a compact manner.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 6A is a front view showing a state of the link actuating device;

FIG. 6B is a bottom view of FIG. 6A;

FIG. 6C is a perspective view of FIG. 6A;

FIG. 7A is a front view showing a different state of the link actuating device;

FIG. 7B is a bottom view of FIG. 7A;

FIG. 7C is a perspective view of FIG. 7A;

FIG. 9A is a front view showing still another different state of the link actuating device;

FIG. 9B is a bottom view of FIG. 9A;

FIG. 9C is a perspective view of FIG. 9A;

DESCRIPTION OF EMBODIMENTS

Figure 1:
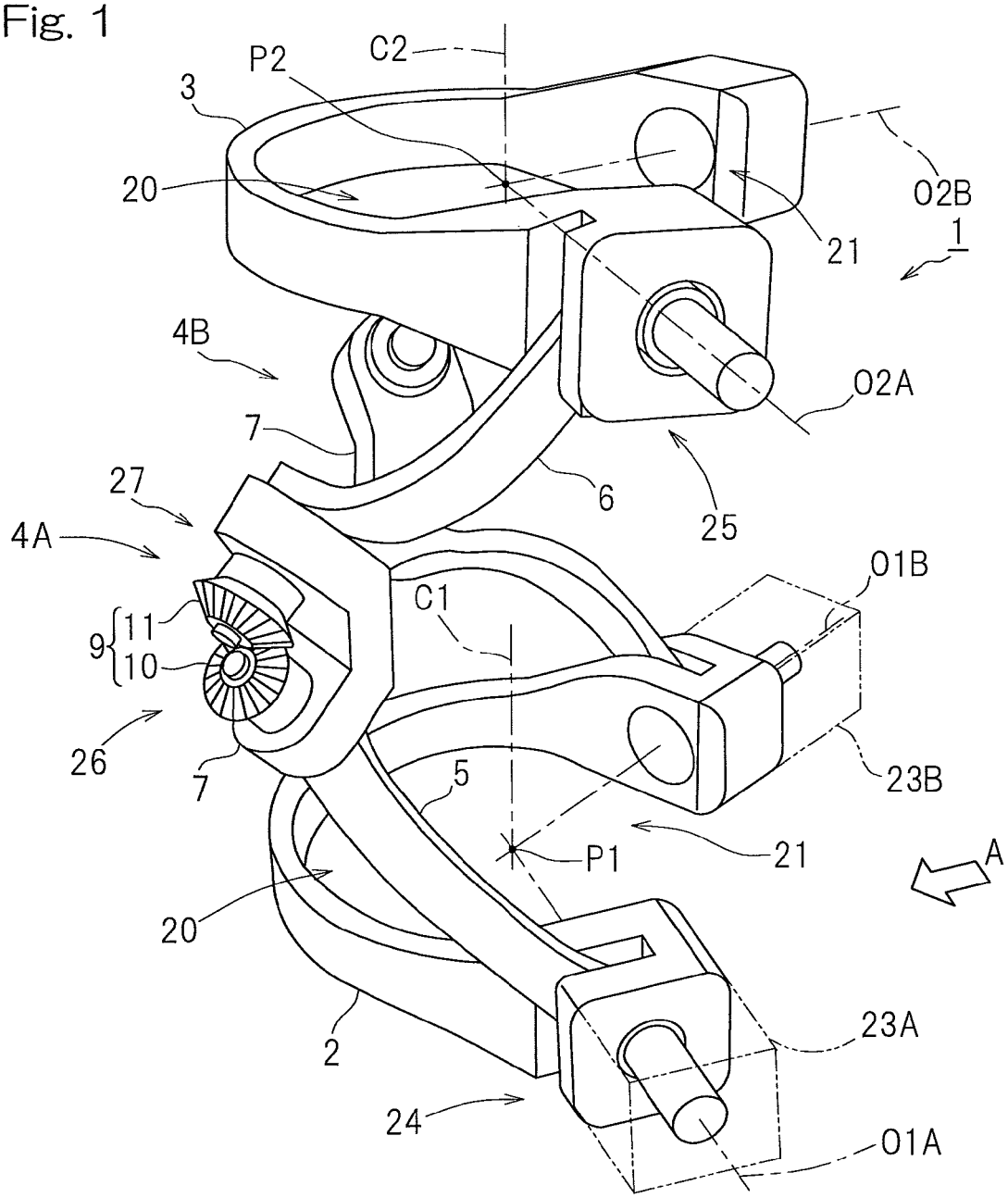
FIG. 1 is a perspective view of a link actuating device according to a first embodiment of the present invention.
Figure 2:
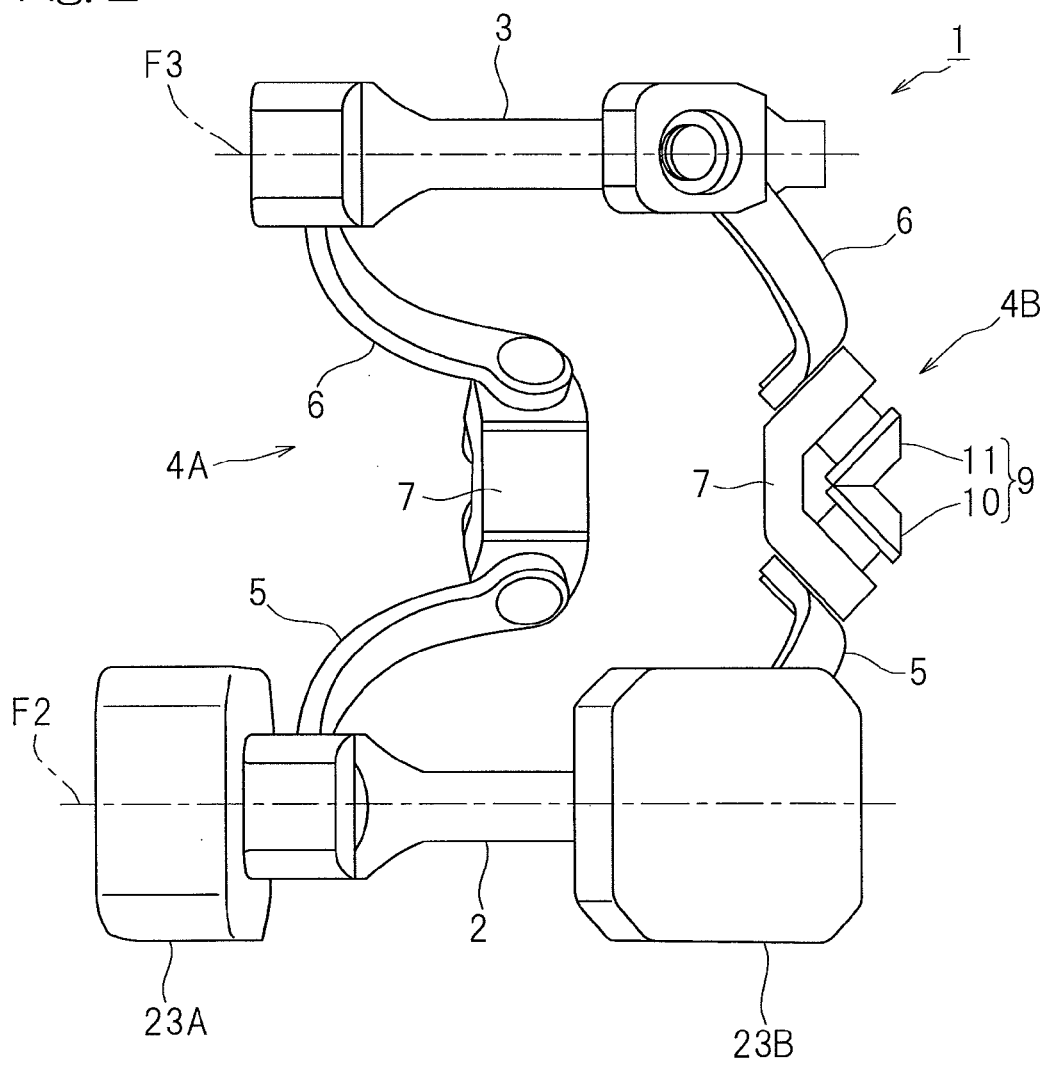
FIG. 2 is a view taken in the direction of the arrow A in FIG. 1.
Figure 3:
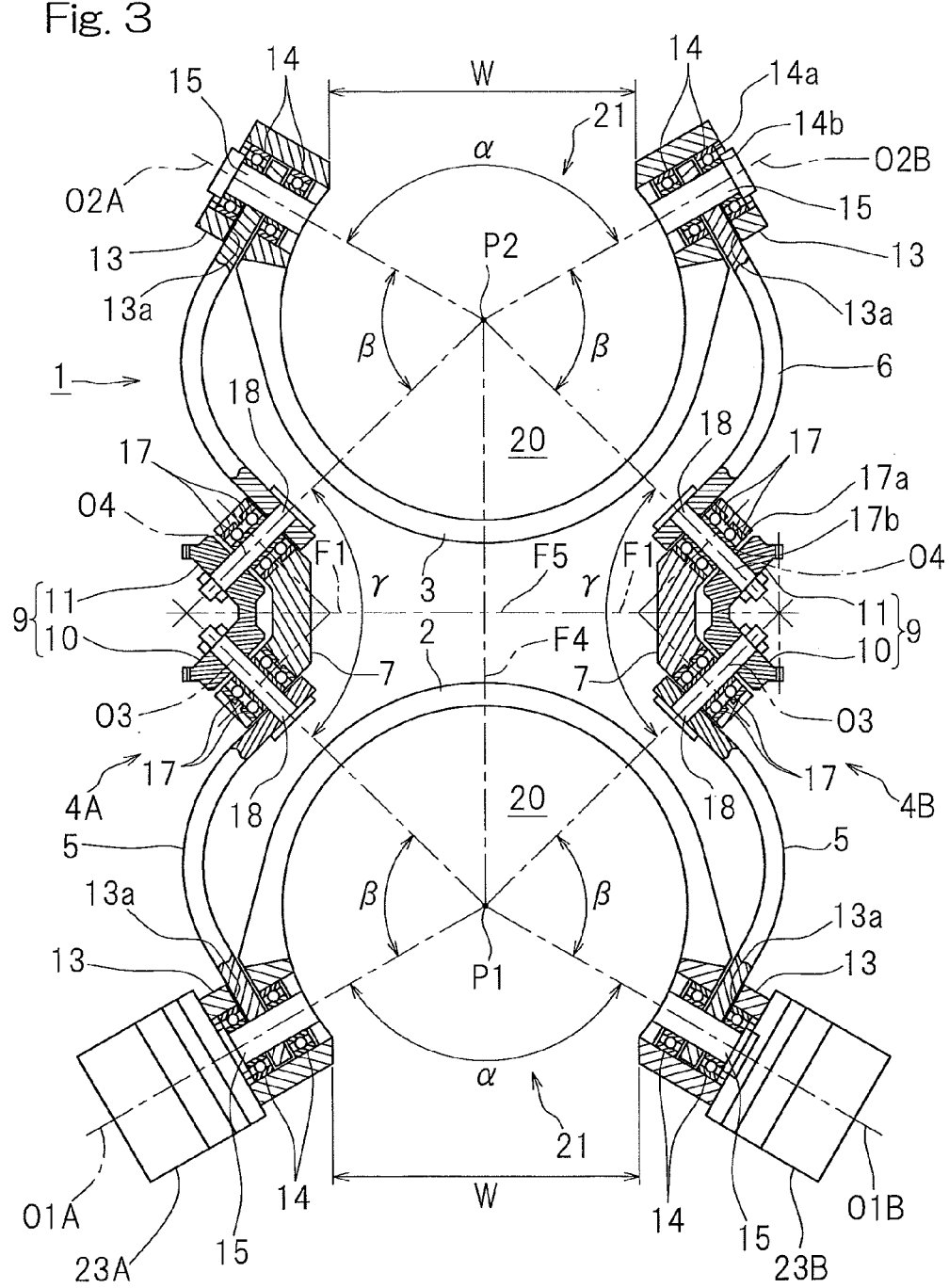
FIG. 3 is a partially broken exploded view showing the link actuating device.

A first embodiment of the present invention will be described with reference to FIG. 1 through FIGS. 9A to 9C. FIGS. 1 and 2 are perspective views of a link actuating device according to the first embodiment as viewed from different angles. FIG. 3 is a partially broken exploded view of the link actuating device. As shown in FIGS. 1 to 3, the link actuating device 1 includes an input side link hub 2, which is a proximal end link hub, and an output side link hub 3, which is a distal end link hub. The link hubs 2 and 3 are connected by two sets of first and second link mechanisms 4A and 4B. Each of the link mechanisms 4A and 4B is a three-link-chain link mechanism including four revolute pairs (first to fourth revolute pair), and includes an input side end link 5 that is rotatably connected to the input side link hub 2 at one end thereof, an output side end link 6 that is rotatably connected to the output side link hub 3 at one end thereof, and an intermediate link 7 that is rotatably connected, at opposite ends thereof, to the other end of each of the end links 5 and 6. Note that although in second and subsequent embodiments described below, a configuration is shown in which the link actuating device 1 includes a link actuating device body 1a and driving unit 1b that drives the link actuating device body 1a, and the link actuating device body 1a and the driving unit 1b are described, this substantially applies to the first embodiment, and thus will not be particularly described.

Figure 4:
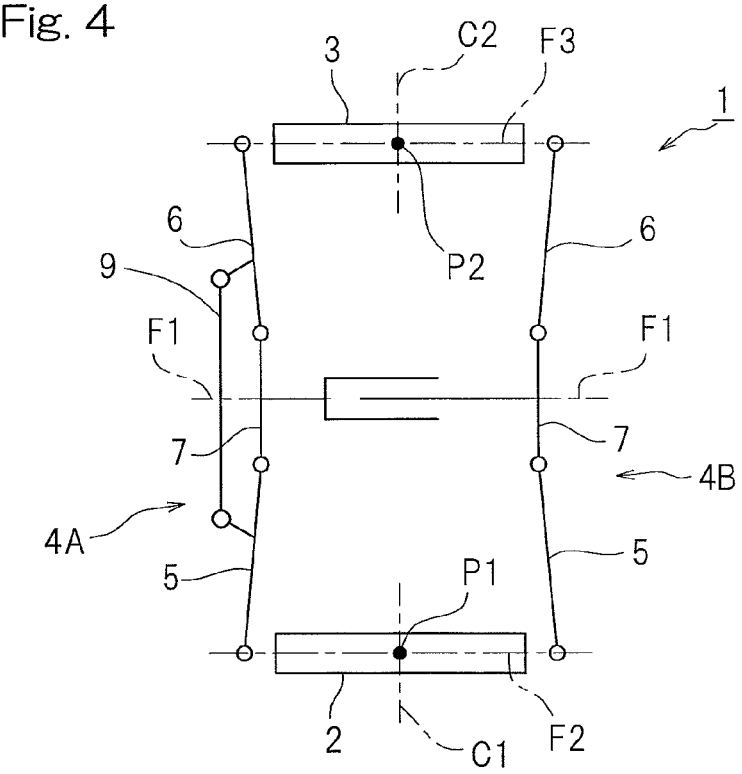
FIG. 4 is a diagram of a link mechanism of the link actuating device represented by straight lines.

The two sets of link mechanisms 4A and 4B have the same geometric shape. Having the same geometric shape means having the same geometric model in which the link mechanism is represented by straight lines as shown in FIG. 4, or in other words, the same model represented by the revolute pairs and the straight lines connecting these revolute pairs. Additionally, the geometric model represented by straight lines of each of the link mechanisms 4A and 4B has an input side portion and an output side portion with respect to the central portion of the intermediate link 7 that have shapes mirror symmetrical to each other. In other words, the input side portion and the output side portion are mirror symmetrical to each other with respect to a transverse cross section F1, serving as a plane of symmetry, that is perpendicular to the direction of arrangement of the two revolute pairs between the intermediate link 7 and each of the input side and output side end links 5 and 6. The transverse cross section F1 can also be regarded as a plane bisecting the angle between the third and fourth revolute pair axes O3 and O4. The third revolute pair axis O3 is an axis of the third revolute pair between the intermediate link 7 and the input side end link 5, and the four revolute pair axis O3 is an axis of the fourth revolute pair between the intermediate link 7 and the output side end link 6.

The input side and output side end links 5 and 6 of each of the link mechanisms 4A and 4B both have a spherical surface link structure. The spherical surface link structure refers to a structure in which the first revolute pair axes O1A and O1B (second revolute pair axes O2A and O2B) between the input side link hub 2 (output side link hub 3) and the input side end link 5 (output side end link 6), and the third revolute pair axis O3 (fourth revolute pair axis O4) between the intermediate link 7 and the input side end link 5 (output side end link 6) all pass through an input side spherical surface link center P1 (output side spherical surface link center P2) as shown in FIG. 3.

The two sets of link mechanisms 4A and 4B have a positional relationship in which the respective first revolute pair axes O1A and O1B (second revolute pair axes O2A and O2B) cross each other. That is, the inter-axis angle between the respective first revolute pair axes O1A and O1B (second revolute pair axes O2A and O2B) is not 180°. Also, the intermediate link 7 of each of the link mechanisms 4A and 4B is located on the side on which the inter-axis angle between the respective first revolute pair axes O1A and O1B (second revolute pair axes O2A and O2B) is greater than 180°. In the illustrated example, the smaller inter-axis angle α is 120°.

Note that in FIG. 3, the two sets of link mechanisms 4A and 4B are disposed at positions where they are mirror symmetrical to each other with respect to a longitudinal cross section F4 passing through the input side and output side spherical surface link centers P1 and P2 and bisecting the inter-axis angle between the respective first revolute pair axes O1A and O1B (second revolute pair axes O2A and O2B) between the input side link hub 2 (output side link hub 3) and the input side end link 5 (output side end link 6).

Each of the third and fourth revolute pair axes O3 and O4 between the input side and output side end links 5 and 6 and the intermediate link 7 may have a certain crossing angle or may be parallel. In the illustrated example, the inter-axis angle γ between the third and fourth revolute pair axes O3 and O4 is 90°. Additionally, in FIG. 3 in which the input side and output side link hubs 2 and 3 are located on the same plane, the inter-axis angle β between each of the respective first revolute pair axes O1A and O1B (second revolute pair axes O2A and O2B) and each of the third revolute pair axes O3 (fourth revolute pair axes O4) is 75°.

In FIGS. 1 to 3, the input side end link 5 and the output side end link 6 of each of the ink mechanisms 4A and 4B are configured to be interlocked by an interlocking unit 9 so as to be rotationally displaced. In the present embodiment, the interlocking unit 9 has a configuration in which a pair of bevel gears 10 and 11 that are rotatable relative to the input side end link 5 and the output side end link 6, respectively, are meshed with each other. The pair of bevel gears 10 and 11 have the same specifications, and interlock the input side end link 5 and the output side end link 6 such that they have rotational directions opposite to each other and have the same rotational displacement angle. When the interlocking unit 9 is achieved by meshing between a plurality of gears such as the bevel gears 10 and 11 in this way, no error will occur in the rotational displacement of the input side end link 5 and the output side end link 6 due to, for example, sliding. Accordingly, the interlocking unit can interlock them accurately and can be made compact.

The interlocking unit 9 is not necessarily achieved by the meshing of a pair of bevel gears 10 and 11 having the same specifications. Link mechanisms, cams, belts or the like may be used in place of the bevel gears. Note that the spur gears are used when the inter-axis angle γ (FIG. 3) is 0°. The pair of gears may have different numbers of teeth. In that case, the input side end link 5 and the output side end link 6 have different rotational displacement angles. Furthermore, the relative rotation between the input side end link 5 and the output side end link 6 may be controlled by using means other than gears, including, for example, rotary actuators or motors.

The input side link hub 2 (output side link hub 3) has an arc shape extending along an input side plane F2 (output side plane F3), on which the first revolute pair axes O1A and O1B (second revolute pair axes O2A and O2B) are located, with the input side spherical surface link center P1 (output side spherical surface link center P2) as the center, and bearing enclosing portions 13 are respectively provided at opposite ends thereof. The bearing enclosing portions 13 each internally include a double row rolling bearings 14, and rotational shafts 15 integrally provided at proximal ends of the input side and output side end links 5 and 6 are rotatably supported by the rolling bearings 14. The axis of each of the rotational shafts 15 coincides with the corresponding revolute pair axis O1A, O1B, O2A, or O2B. The two rolling bearings 14 are disposed with an axial gap, and the proximal end of each of the input side and output side end links 5 and 6 is located at the gap portion. A groove 13a in which the basal portion of each of the end links 5 and 6 is rotationally fitted is formed in each of the bearing enclosing portions 13. Regulating the rotational range of the end links 5 and 6 by using the groove 13a enables the intermediate link 7 of each of the link mechanisms 4A and 4B to be always located on the side where the inter-axis angle between the respective first revolute pair axes O1A and O1B (second revolute pair axes O2A and O2B) is greater than 180° as described above.

An outer ring 14a of each rolling bearing 14 is fitted to the inner circumference of the bearing enclosing portion 13 by press-fitting or the like, and an inner ring 14b thereof is fitted to the outer circumference of the rotational shaft 15 by press-fitting or the like. The rolling bearing 14 is, for example, a ball bearing such as a deep groove ball bearing or an angular contact ball bearing. Besides double row ball bearings as the illustrated example, a roller bearing may be used as the rolling bearing 14. Alternatively, a sliding bearing may be used in place of the rolling bearings 14.

Additionally, rolling bearings 17 are provided at opposite end portions of the intermediate link 7, and rotational shafts 18 that are integrally provided at distal ends of the end links 5 and 6 are supported by the rolling bearings 17. The axis of each of the rotational shafts 18 coincides with the corresponding third or fourth revolute pair axis O3 or O4. An outer ring 17a of each rolling bearing 17 is fitted to the end portion of the intermediate link 7 by press-fitting or the like, and an inner ring 17b thereof is fitted to the outer circumference of the rotational shaft 18 by press-fitting or the like. The rolling bearing 17 is, for example, a ball bearing such as a deep groove ball bearing or an angular contact ball bearing. Beside double row ball bearing in the illustrated example, a roller bearing may be used as the rolling bearing 17. Alternatively, a sliding bearing may be used in place of the rolling bearings 17.

The input side and output side link hubs 2 and 3 each have an arc shape as previously described, and each internally includes a hollow portion 20 passing through in a direction perpendicular to the input side and output side planes F2 and F3, respectively, or in other words, in the direction of input side and output side central axes C1 and C2 (FIGS. 1 and 3). The hollow portion 20 is in communication with the outside of the link hubs 2 and 3 via an opening portion 21 formed between the pair of bearing enclosing portions 13. The opening portion 21 is located on the same side as each of the revolute pair axes O1A, O1B, O2A, and O2B for both of the input side and output side link hubs 2 and 3. That is, as shown in FIG. 1, the opening portions 21 of the input side and output side link hubs 2 and 3 face the same side when the input side link hub 2 and the output side link hub 3 are in an attitude in which they are parallel to each other.

The first and second link mechanisms 4A and 4B are each provided with respective first and second actuators 23A and 23B capable of arbitrarily changing the attitude of the input side end link 5 relative to the input side link hub 2. The actuators 23A and 23B are, for example, rotary actuators, and rotate the corresponding input side end link 5 by rotationally driving the rotational shafts 15. The input side end link 5 may be rotated by using actuators other than rotary actuators. In addition, the installation locations of the actuators 23A and 23B are not limited to the above-described locations. It is sufficient that the actuators 23A and 23B can arbitrarily change the rotational angle of one of the four revolute pairs of the link mechanisms 4A and 4B.

When the input side end links 5 are rotated by the actuators 23A and 23B, the input side end links 5 and the output side end links 6 are rotationally displaced in conjunction with each other by the interlocking unit 9 in both the link mechanisms 4A and 4B. Thereby, the movement or the attitude of the output side link hub 3 relative to the input side link hub 2 is uniquely determined. That is, the link actuating device 1 is a mechanism having two degrees of freedom of rotation, in which the attitude of the output side link hub relative to the input side link hub is uniquely determined.

This will be described in detail. In this structure, the input side link hub 2 and the input side end link 5 connected thereto, and the output side link hub 3 and the output side end link 6 connected thereto constitute spherical surface link mechanisms. In each of the spherical surface link mechanisms, the input side and output side end links 5 and 6 are connected via the intermediate link 7. Here, the two intermediate links 7 of the first and second link mechanisms 4A and 4B have one degree of freedom in which they are limited to translation movements on the circumference of a circle with which the corresponding spherical surface link mechanisms overlap. Assuming that the radius of curvature of a link is infinite, the spherical surface link mechanisms on the input side and the output side are four-link mechanisms on a plane, and each of the spherical surface link mechanisms on the input side and the output side independently has one degree of freedom. When no interlocking unit 9 is provided between the input side and output side end links 5 and 6, the two intermediate links 7 have one degree of freedom and each of the spherical surface link mechanisms on the input side and the output side has one degree of freedom, resulting in a total of three degrees of freedom.

Here, since the link actuating device 1 includes the interlocking unit 9 between the input side and output side end links 5 and 6, the respective spherical surface link mechanisms are interlocked, and thus the two spherical surface link mechanisms have one degree of freedom. As described above, the link actuating device 1 is a mechanism having a total of two degrees of freedom, including one degree of freedom of the intermediate links 7 and one degree of freedom of the spherical surface link mechanism. Note that the positional displacement of each intermediate link 7 is an angular change between the input side and output side link hubs 2 and 3. Accordingly, a structure can be provided that allows the angular change in two directions between the input side and output side link hubs 2 and 3.

As in the present embodiment, in the two sets of link mechanisms 4A and 4B, when the angle and the length of the respective end links 5 and 6 and the geometric shape of the respective end links 5 and 6 are the same on the input side and the output side and the shape of the intermediate link 7 is the same on the input side and the output side, the input side link hub 2 and the input side end link 5, and the output side link hub 3 and the output side end link 6 move identically due to the geometric symmetry by setting the same angle positional relationship between the intermediate link 7 and the input side and output side end links 5 and 6 that are connected to the input side and output side link hubs 2 and 3 relative to the plane of symmetry of the intermediate link 7 for the input side and the output side.

Figure 5:
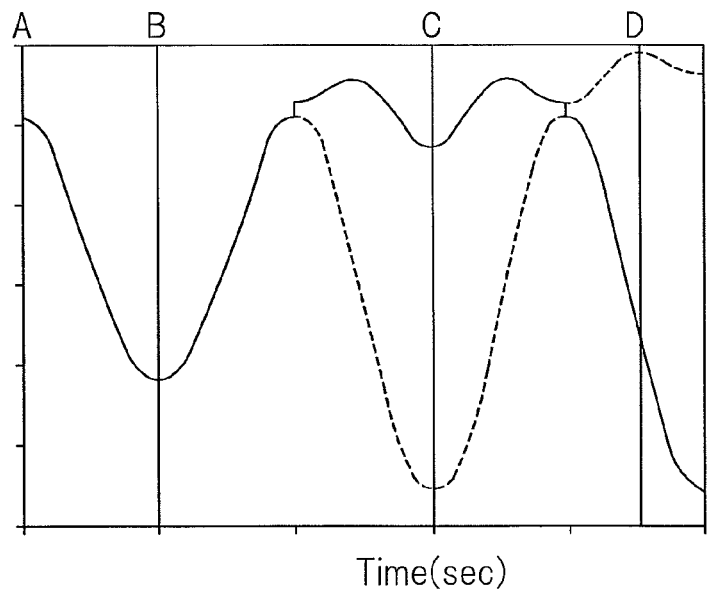
FIG. 5 is a graph showing changes in magnitude of torque applied to the link actuating device.

Specific operations of the link actuating device 1 will be described. FIG. 5 is a graph on which change in torque acting on the first and second link mechanisms 4A and 4B, when the rotational angle of the revolute pair between the input side link hub 2 and the input side end link 5 is changed by the actuators 23A and 23B, is nondimensionalized by the torque in the state shown in FIGS. 6A to 6C. FIGS. 6A to 6C through FIGS. 9A to 9C each show a front view, a bottom view, and a perspective view representing the link actuating device 1 as a simplified model, and FIGS. 6A to 6C, 7A to 7C, 8A to 8C and 9A to 9C respectively show the attitudes at the time points A, B, C, and D in FIG. 5. This model shows a case where the input side plane F2 (FIG. 2) including the respective first revolute pair axes O1A and O1B (FIG. 3) between the input side link hub 2 and the input side end link 5 is brought into an upright state and the opening portion 21 is disposed in the gravity G direction. In FIGS. 6A to 6C to FIGS. 9A to 9C, the input side and output side spherical surface link centers P1 and P2 are shown as spheres and a weight is disposed at the center P2 of the output side link hub 3. The weight is set to be sufficiently heavier than the weight of the device.

Figure 8C:
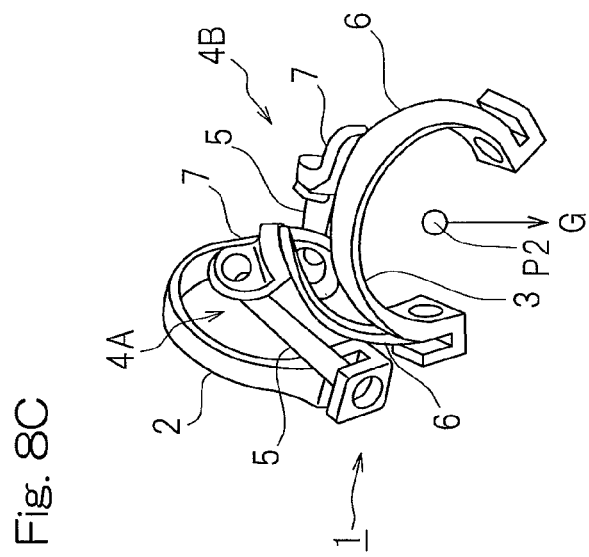
FIG. 8C is a perspective view of FIG. 8A.
Figure 8A:
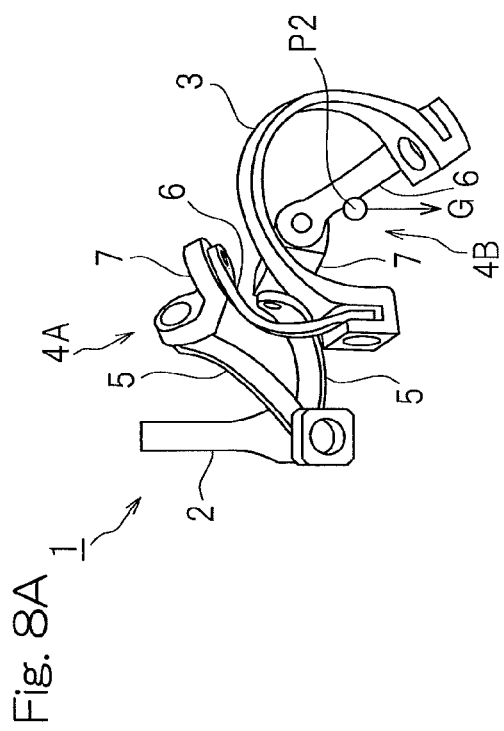
FIG. 8A is a front view showing another different state of the link actuating device.
Figure 8B:
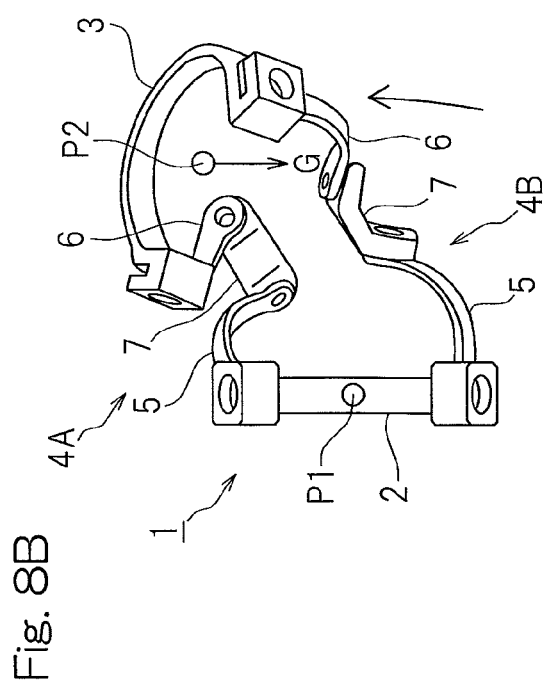
FIG. 8B is a bottom view of FIG. 8A.

FIGS. 6A to 6C show a state in which the output side link hub 3 is parallel to the input side link hub 2. At this time, in order to maintain the attitudes of the output side link hub 3 and the respective links 5, 6, and 7 of the first and second link mechanisms 4A and 4B against the gravity G, the actuators 23A and 23B (FIGS. 1 to 3) cause the same predetermined value of torque to act on each of the first and second link mechanisms 4A and 4B. When the torque acting on the link mechanisms 4A and 4B is decreased to be smaller than the predetermined value from the state shown in FIGS. 6A to 6C, the output side link hub 3 is pivoted downward until the respective intermediate links 7 of the first and second link mechanisms 4A and 4B interfere with each other as shown in FIGS. 7A to 7C. When the angle between the input side link hub 2 and the input side end link 5 of the first link mechanism 4A is fixed and the torque acting on the second link mechanism 4B is decreased from the state shown in FIGS. 6A to 6C, the overall first link mechanism 4A contracts and the overall second link mechanism 4B extends as shown in FIGS. 8A to 8C, resulting in an attitude in which the output side link hub 3 is inclined forward (the near side in FIG. 8A). Furthermore, when the torque acting on the first link mechanism 4A and the torque acting on the second link mechanism 4B are separately changed from the predetermined value, the device is in an attitude in which the output side link hub 3 is twisted relative to the input side link hub 2 as shown in FIGS. 9A to 9C. In all of these states, even if the attitude of the output side link hub 3 relative to the input side link hub 2 changes, the distance between the input side and output side spherical surface link centers P1 and P2 does not change.

As shown in FIGS. 6A to 6C through FIGS. 9A to 9C, the link actuating device 1 can ensure a wide movable range for the output side link hub 3 relative to the input side link hub 2. For example, a maximum value (maximum bending angle) of the bending angle θ (FIG. 7 A) between the central axis C1 of the input side link hub 2 and the central axis C2 of the output side link hub 3 can be 90° or more. In addition, the turning angle φ (FIG. 9B) of the output side link hub 3 relative to the input side link hub 2 can be set in the range from 0° to 360°. The bending angle θ refers to the inclination angle of the central axis C2 of the output side link hub 3 relative to the central axis C1 of the input side link hub 2, and the turning angle φ refers to an horizontal angle by which the output side link hub 3 is inclined relative to the central axis C1 of the input side link hub 2.

By using the interlocking unit 9, the link actuating device 1 interlocks the input side end link 5 and the output side end link 6 such that rotational directions thereof relative to the intermediate link 7 are opposite to each other and rotational displacement angles thereof are the same. Thereby, at the time of changing the attitude of the output side link hub 3 relative to the input side link hub 2, the plane F5 (FIG. 3), that is located at an intermediate point between the input side and output side spherical surface link centers P1 and P2 and is perpendicular to the straight line connecting the input side and output side spherical surface link centers P1 and P2, always coincides with the transverse cross section F1 (FIG. 3) perpendicular to the direction of arrangement of the two revolute pairs between the intermediate link 7 and each of the input side and output side end links 5 and 6. In the illustrated example, both of the two sets of link mechanisms 4A and 4B include the interlocking unit 9, and therefore the link actuating device 1 has high rigidity, making it possible to accurately position the output side link hub 3.

Each of the first and second link mechanisms 4A and 4B includes the four revolute pairs composed of the connecting portion between the input side link hub 2 and the input side end link 5, the connecting portion between the output side link hub 3 and the output side end link 6, and the two connecting portions between the input side and output side end links 5 and 6 and the intermediate link 7. By forming these four revolute pairs as bearing structures, the frictional resistance in the respective connecting portions can be suppressed to reduce the rotational resistance, thus ensuring smooth power transmission and improving the durability.

The link actuating device 1 includes two sets of the link mechanisms 4A and 4B, which is less than conventionally used three sets of link mechanisms, and thus can more easily avoid interference between the first and second link mechanisms 4A and 4B and has a high degree of freedom in design. This enables the link actuating device 1 to have a compact configuration with a small overall outer diameter. Furthermore, it is possible to achieve cost reduction due to the reduction in the number of the link mechanisms 4A and 4B. Furthermore, since the first and second link mechanisms 4A and 4B have the same shape, it is possible to reduce the number of types of parts, which also makes it possible to achieve cost reduction.

The intermediate links 7 of the first and second link mechanisms 4A and 4B are located on the side on which the angle between the respective first revolute pair axes O1A and O1B (second revolute pair axes O2A and O2B) between the input side link hub 2 (output side link hub 3) and the input side end link 5 (output side end link 6) of the two sets of link mechanisms 4A and 4B is greater than 180°. Accordingly, in terms of the structure, the revolute pair portions 24 and 25 (FIG. 1) between the input side and output side link hubs 2 and 3 and the respective input side and output side end links 5 and 6 of one first link mechanism 4A (second link mechanism 4B) tend not to interfere with the revolute pair portions 26 and 27 (FIG. 1) between the input side and output side end links 5 and 6 and the intermediate link 7 of the other second link mechanism 4B (first link mechanism 4A). This eliminates the need to provide the revolute pair portions 26 and 27 between the input side and output side end links 5 and 6 and the intermediate link 7 so as to protrude in the outer diameter direction to avoid the above-described interference, and it is thus possible to achieve a compact configuration with a small outer diameter.

The input side and output side link hubs 2 and 3 respectively include hollow portions 20 passing through along the directions of the respective central axes C1 and C2. Accordingly, cables such as an electric wire and an air tube can be provided through the hollow portions 20, thereby preventing the cables from easily coming into contact with the respective links 5, 6, and 7 and anything other than the link actuating device 1. Since the hollow portions 20 are in communication with the outside of the link hubs 2 and 3 via the opening portions 21, it is possible to place the cables in the hollow portion 20 even if the cables are connected to devices during insertion of the cables through the hollow portions 20, thus improving the operability.

The two sets of link mechanisms 4A and 4B have shapes in which the input side portion and the output side portion are mirror symmetrical with each other with respect to the central portion of the intermediate links 7, and the input side end link 5 and the output side end link 6 have the same movable range in the circumferential direction. Accordingly, a circumferential region, in which the respective end links 5 and 6 and the intermediate links 7 do not enter, is rendered to be larger in the space between the input side link hub 2 and the output side link hub 3, enabling an article to be placed from this region into the space. In this region, the respective links 5, 6, and 7 may be brought closer to other members, and therefore the apparatus is more compact when mounted to a robot, industrial machine or the like.

Furthermore, at the time of attaching an assembly composed of the intermediate link 7 and the input side and output side end links 5 and 6 to the input side and output side link hubs 2 and 3, the revolute pair axes of the attachment portions (not shown) have the circumferential positions coincided with each other on the input side and the output side, and it is therefore possible to attach the assembly from one direction, thus improving the ease of assembly.

When each of the first and second link mechanisms 4A and 4B includes the actuator 23A or 23B capable of arbitrarily changing the rotational angle of one of the four revolute pairs of the corresponding link mechanisms 4A and 4B as in the present embodiment, it is possible to control the movements of the two sets of link mechanisms 4A and 4B to arbitrarily change the attitude of the output side link hub 3 relative to the input side link hub 2. Since the first and second link mechanisms 4A and 4B have the geometrically same shape, they can be controlled easily.

When the actuators 23A and 23B are provided so as to change the rotational angle of the revolute pair between the input side link hub 2 and the input side end link 5, which is positioned on the stationary side, as in the illustrated example, it is possible to reduce the load weight on the output side link hub 3, which is positioned on the movable side, resulting in an increase in the weight capacity of the output side link hub 3. Furthermore, inertial force at the time of operating the link actuating device 1 is reduced, thus facilitating the attitude control for the output side link hub 3.

Although both of the two sets of link mechanisms 4A and 4B includes the interlocking unit 9 in the present embodiment, it is sufficient that at least one of the two sets of link mechanisms 4A and 4B includes the interlocking unit 9. For example, it is assumed that the interlocking unit 9 is provided only in the first link mechanism 4A. In that case, in the first link mechanism 4A that is provided with the interlocking unit 9, the input side end link 5 and the output side end link 6 are rotationally displaced in conjunction with each other by the interlocking unit 9. Thereby, the movement of the output side link hub 3 relative to the input side link hub 2 is regulated to one degree of freedom of movement. The second link mechanism 4B in which the interlocking unit 9 is not provided is operable within the range of the one degree of freedom of the input side and output side link hubs 2 and 3. When one of the revolute pairs in the second link mechanism 4B in which the interlocking unit 9 is not provided is set in an arbitrary position by the actuator 23B, the attitude of the output side link hub 3 relative to the input side link hub 2 is uniquely determined. That is, the link actuating device 1 is also a mechanism having two degrees of freedom of rotation in which the attitude of the output side link hub 3 relative to the input side link hub 2 is uniquely determined.

Other embodiments will now be described. In the following description, the portions of embodiments that correspond to the portions described in the preceding embodiment are denoted by the same reference numerals, and any redundant description thereof has been omitted. When only a part of a configuration is described, the remaining part of the configuration is the same as that of the previously described embodiment unless otherwise specified.

Figure 10:
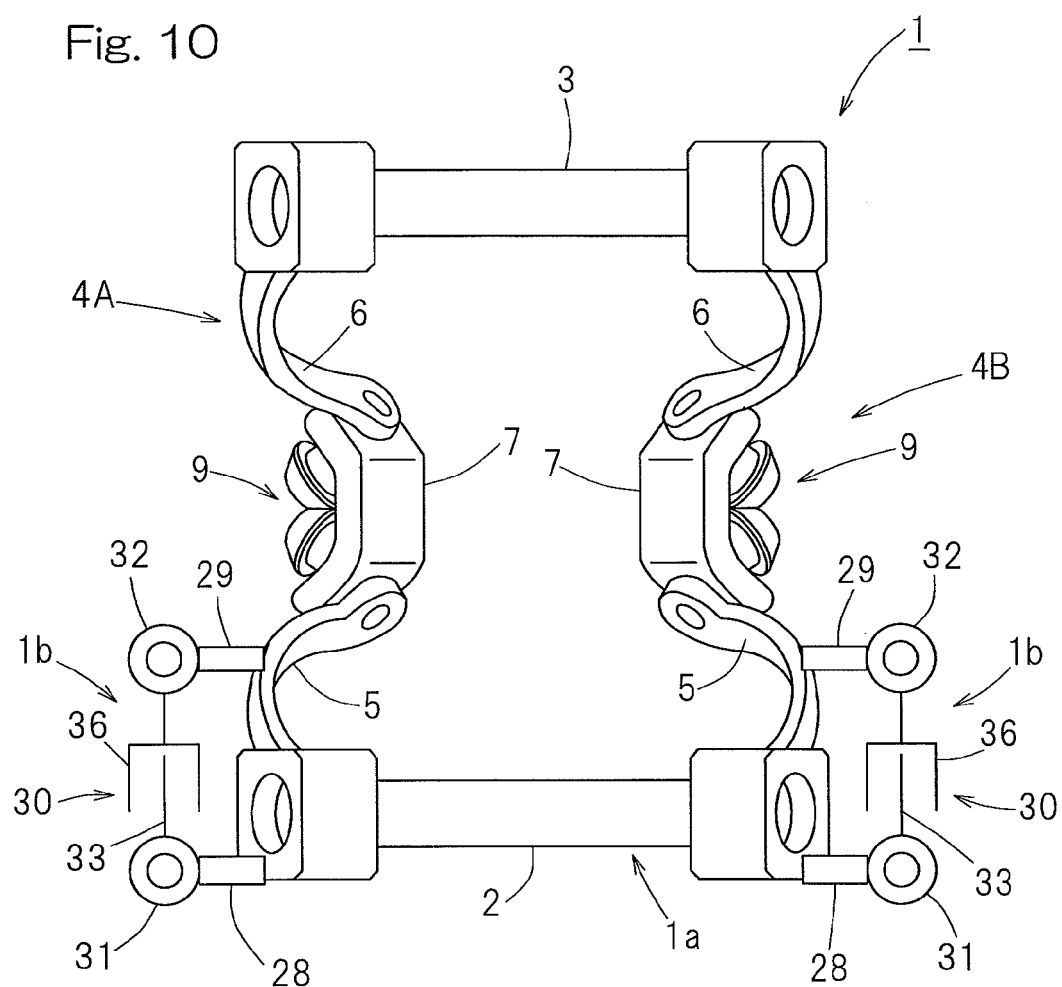
FIG. 10 is a bottom view of a link actuating device according to a second embodiment of the present invention.

A second embodiment of the present invention will be described with reference to the drawings. FIG. 10 is a bottom view of a link actuating device according to the second embodiment of the present invention. The link actuating device 1 includes a link actuating device body 1*a* and driving unit 1*b* that drives the link actuating device body 1*a*. The link actuating device body 1*a* will be described first. Note that FIG. 1, FIGS. 2 to 9A to 9C used in the description of the first embodiment above can also be employed in the description of the second embodiment as common drawings, and the detailed description thereof has been omitted. Note that in the second embodiment, reference will be made to FIG. 1 and FIG. 2, excluding the actuators 23A and 23B.

In FIG. 10, the driving unit 1*b* is provided in each of first and second link mechanisms 4A and 4B and changes the relative angle or position between two link mechanism components that are different from each other. The input side and output side link hubs 2 and 3, the input side and output side end links 5 and 6, and the intermediate link 7 correspond to the link mechanism components. In the second embodiment, the relative angle or position between each input side link hub 2 and each input side end link 5 are changed by connecting a first auxiliary plate 28 that is provided integrally with each input side link hub 2 and a second auxiliary plate 29 that is provided integrally with each input side end link 5 by an extendable linear actuator 30. Respective first and second connecting portions 31 and 32 between each linear actuator 30 and the first and second auxiliary plates 28 and 29 both constitute revolute pairs. Additionally, each first auxiliary plate 28 is fixed to the input side link hub 2 at a position away from the first revolute pair axes O1A and O1B between the input side link hubs 2 and the input side end links 5. The linear actuator 30 may be any drive mechanism that performs extending and contracting operations in the linear direction, and a mechanism using a ball screw or a hydraulic cylinder device may be used, for example.

Figure 11:
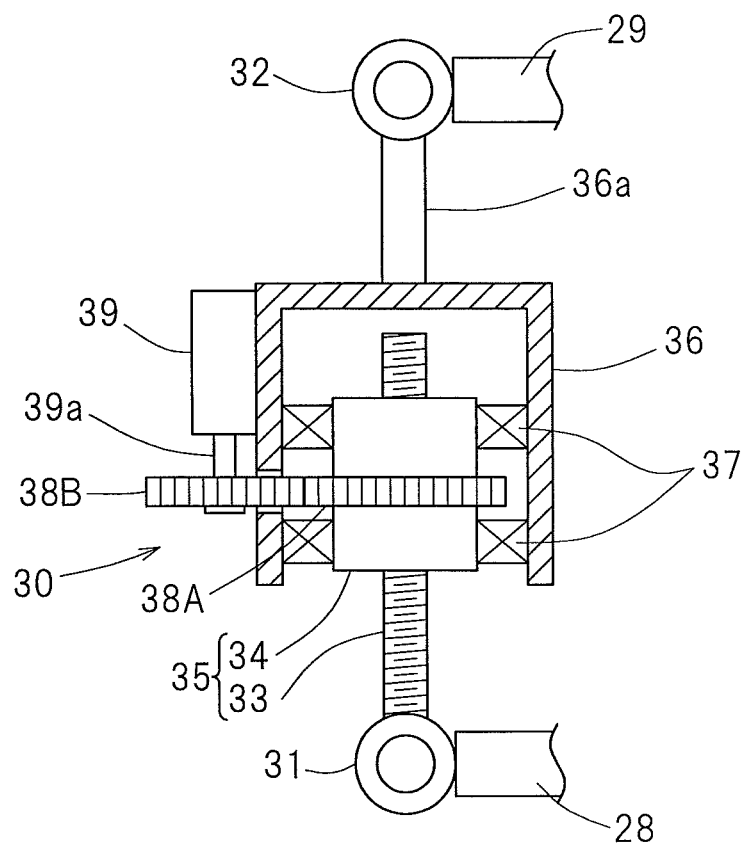
FIG. 11 is a vertical cross-sectional view showing an example of a linear actuator of the link actuating device.

FIG. 11 shows an exemplary linear actuator that uses a ball screw. The linear actuator 30 includes a nut 34 threadably engaged with a screw shaft 33 connected to the first auxiliary plate 28, and the screw shaft 33 and the nut 34 constitute a ball screw 35. The screw shaft 33 forms to an advancing or retracting shaft. The nut 34 is rotatably supported by two bearings 37 on an outer cylinder body 36 connected to the second auxiliary plate 29 via a rod 36*a*. A first spur gear 38A is provided on the outer circumference of the nut 34, and another second spur gear 38B is meshed with the first spur gear 38A. The second spur gear 38B is attached to an output shaft 39*a* of a motor 39 installed on the outer circumference of the outer cylinder body 36. By rotating the motor 39, the nut 34 is rotated via the first and second spur gears 38A and 38B, and the screw shaft 33 is advanced or retracted relative to the nut 34 by the ball screw 35. Thereby, the distance between the distal end of the screw shaft 33 and the distal end of the rod 36*a* is changed. In other words, the linear actuator 30 expands and contracts.

With the arrangement in which the opposite ends of the linear actuator 30 are connected to the input side link hub 2 and the input side end link 5 connected thereto as in the second embodiment, the first connecting portion 31 between the input side link hub 2 and the linear actuator 30 and the second connecting portion 32 between the input side end link 5 and the linear actuator 30 can both constitute revolute pairs. In other words, the first and second connecting portions 31 and 32 can constitute two-dimensional pairs. Accordingly, a bearing such as a deep groove ball bearing can be used for the first and second connecting portions 31 and 32, and it is therefore possible to reduce the cost and the rotational resistance as compared with the use of a spherical pair or a cross joint. Additionally, there is no limitation on the rotational angle in the case of using a bearing such as a deep groove ball bearing, and therefore the degree of freedom in design increases.

When the input side end link 5 is rotated relative to the input side link hub 2 by the extending or contracting operations of the linear actuator 30 of the driving unit 1*b*, this rotation of the input side end link 5 is transmitted to the output side end link 6 by the interlocking unit 9, and as a result, the input side end link 5 and the output side end link 6 are rotationally displaced in conjunction with each other. Since the driving unit 1*b* is provided in each of the link mechanisms 4A and 4B, the rotational displacement of the output side end link 6 of each of the link mechanisms 4A and 4B is determined. Thereby, the attitude of the output side link hub 3 relative to the input side link hub 2 is uniquely determined. That is, the link actuating device 1 is a mechanism having two degrees of freedom of rotation in which the attitude of the output side link hub 3 relative to the input side link hub 2 is uniquely determined.

In the second embodiment, the linear actuator 30 (FIG. 10), which replaces the actuators 23A and 23B in the first embodiment, causes the same predetermined value of torque to act on each of the link mechanisms 4A and 4B.

By the provision of the interlocking unit 9, the link actuating device 1 can define the attitude of the output side link hub 3 relative to the input side link hub 2 even if the number of sets of the link mechanisms 4A and 4B is two. Since the number of sets of the link mechanisms 4A and 4B is two, which is fewer than conventionally used three sets, the interference between the first and second link mechanisms 4A and 4B can be more easily prevented and thus an increased degree of freedom in design is achieved. This enables the link actuating device 1 to have a compact configuration with a small overall outer diameter. Furthermore, it is possible to achieve cost reduction due to the smaller number of the link mechanisms 4A and 4B. Although there is concern that reducing the number of the link mechanisms 4A and 4B may result in a lower rigidity, the link actuating device 1 according to the second embodiment achieves a high rigidity because it has a link configuration that is closed by the input side link hub 2, the input side end link 5, and the linear actuator 30.

Figure 12:
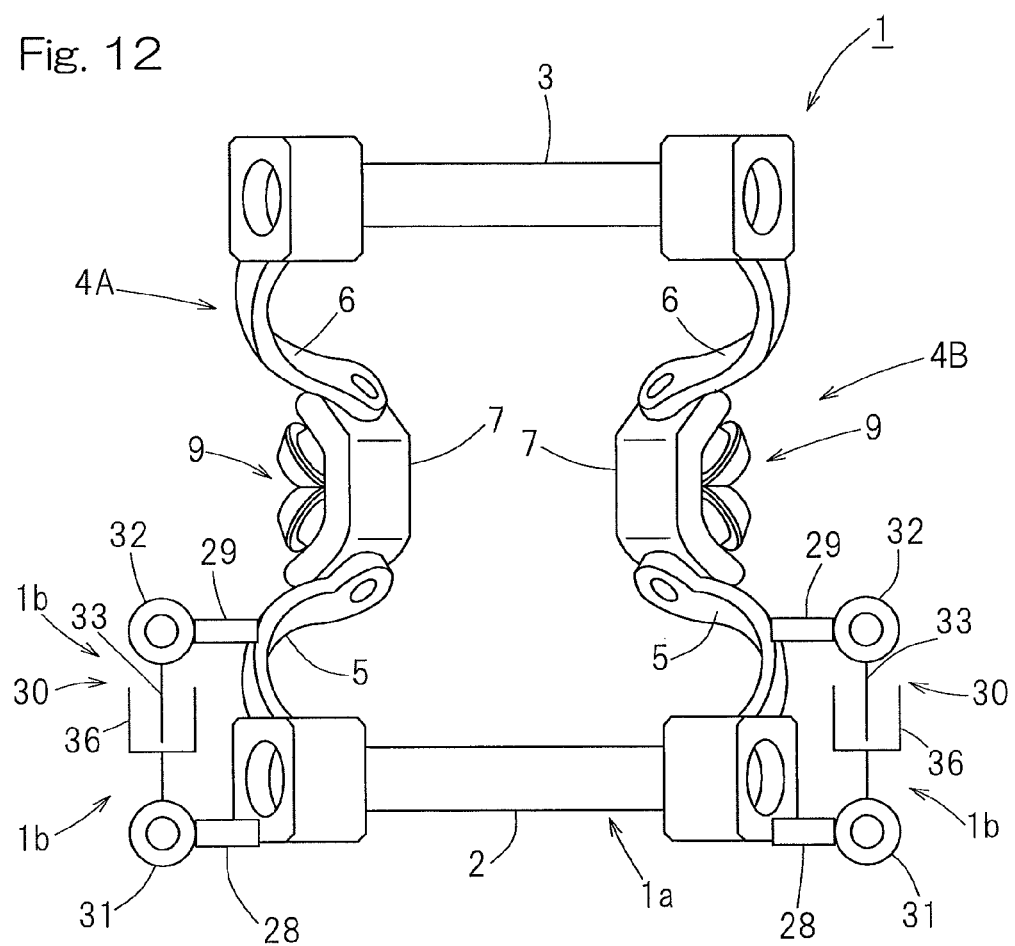
FIG. 12 is a bottom view of a link actuating device according to a third embodiment of the present invention.

As shown in a third embodiment of FIG. 12, the linear actuator 30 may have an arrangement in which the screw shaft 33 serving as the advancing or retracting shaft and the outer cylinder body 36 are disposed in an inverted manner. This arrangement also functions in the same manner as the arrangement shown in FIG. 10.

Figure 13:
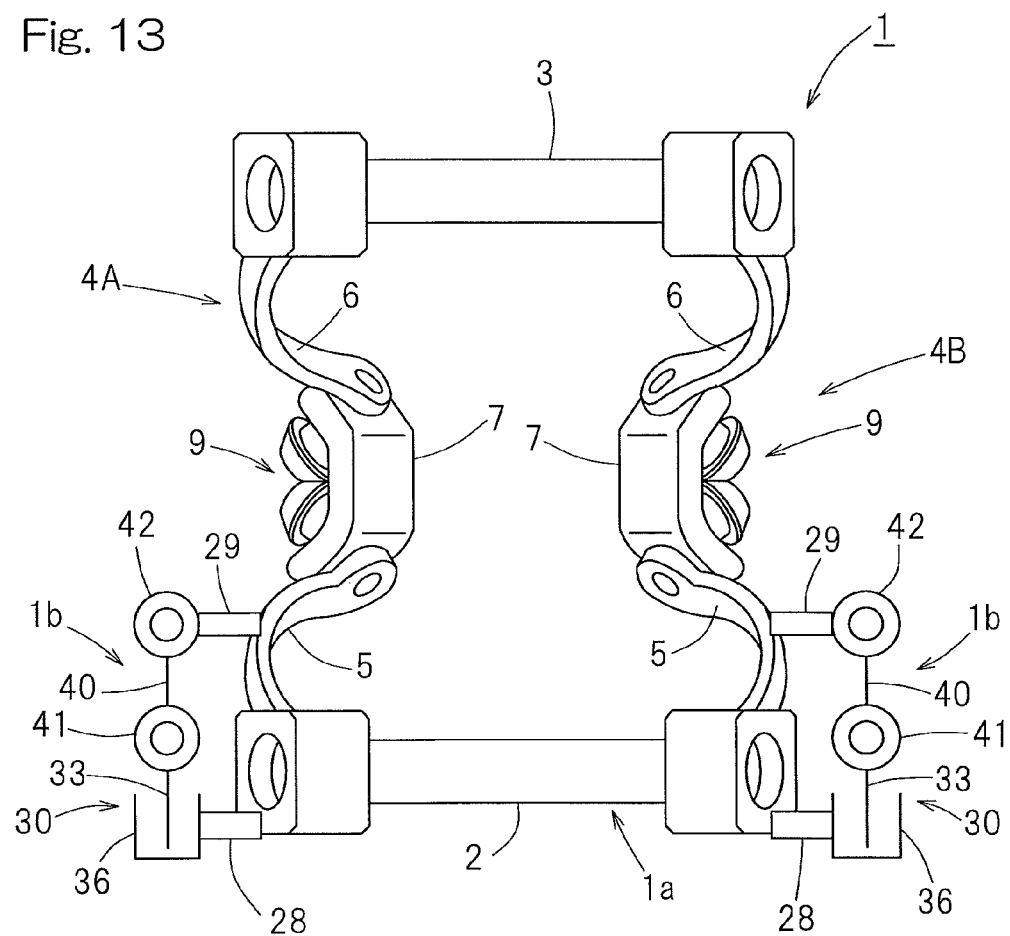
FIG. 13 is a bottom view of a link actuating device according to a fourth embodiment of the present invention.

As in a fourth embodiment shown in FIG. 13, the outer cylinder body 36 of the linear actuator 30 may be fixed to the first auxiliary plate 28 that is integrally provided with the input side link hub 2, and the screw shaft 33 serving as the advancing or retracting shaft may be connected via an auxiliary link 40 to the second auxiliary plate 29 that is provided with the input side end link 5. A first connecting portion 41 between the screw shaft 33 and the auxiliary link 40 and a second connecting portion 42 between the second auxiliary plate 29 and the auxiliary link 40 both constitute revolute pairs. The auxiliary link 40 serves to adjust the positional relationship between the screw shaft 33 and the input side end link 5 in response to the advancement or retraction of the screw shaft 33.

When the outer cylinder body 36 and the screw shaft 33 of the linear actuator 30 are compared, the outer cylinder body 36 has a larger diameter and a larger weight than the screw shaft 33. By fixing the heavier outer cylinder body 36 to the input side link hub 2 positioned on the fixed side, it is possible to reduce the weight of the movable portion, thereby improving the responsiveness to the driving of the linear actuator 30. Furthermore, since the moving portion of the linear actuator 30 can be made compact, it is possible to make the linear actuator 30 less prone to interference with the other members of the link actuating device 1 or articles other than the link actuating device 1.

Figure 14:
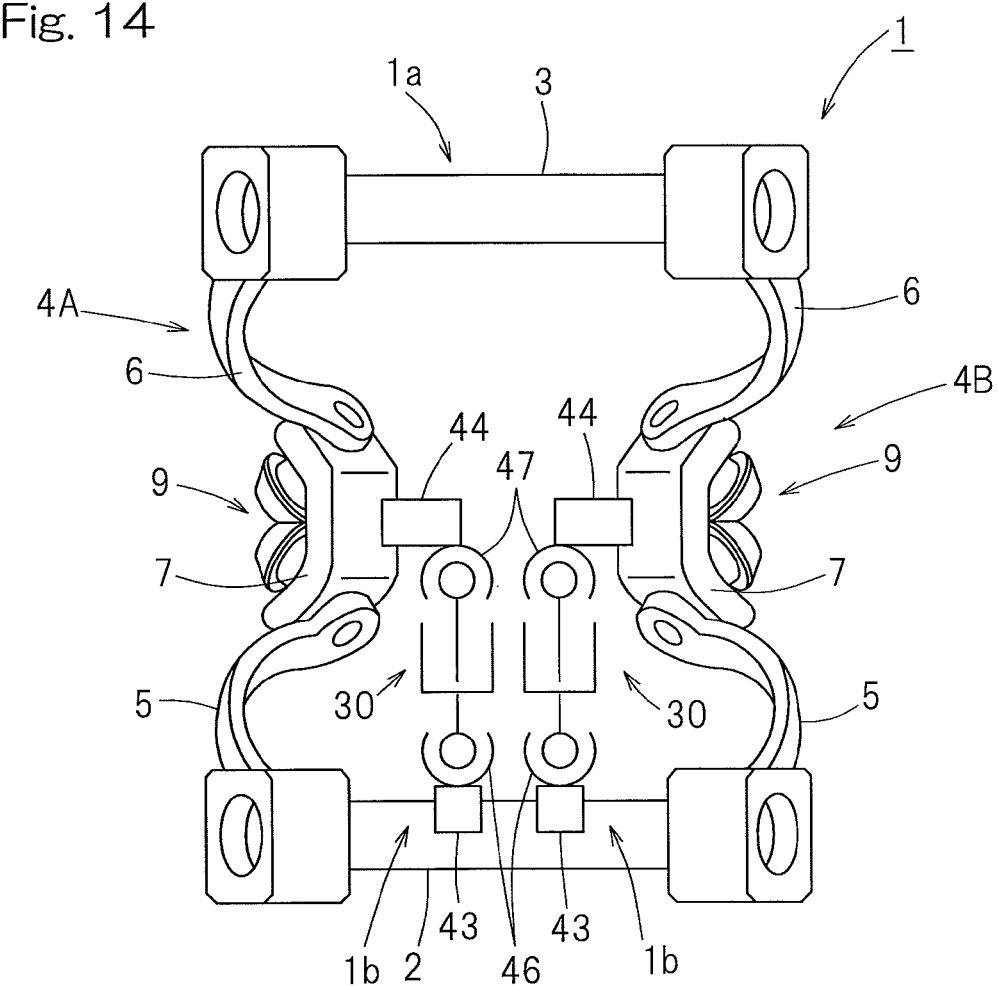
FIG. 14 is a bottom view of a link actuating device according to a fifth embodiment of the present invention.

FIG. 14 shows a fifth embodiment. With the link actuating device 1, the relative angle or position between the input side link hub 2 and the intermediate link 7 is changed by connecting a third auxiliary plate 43 that is provided integrally with the input side link hub 2 and a fourth auxiliary plate 44 that is provided integrally with the intermediate link 7 by the extendable linear actuator 30. The input side link hub 2 and the intermediate link 7 relatively move in three dimensions, and therefore connecting portions 46 and 47 between each linear actuator 30 and each of the third and fourth auxiliary plates 43 and 44 both constitute spherical pairs.

In this fifth embodiment, the link actuating device 1 has a link configuration that is closed by the input side link hub 2, the input side end link 5, the intermediate link 7 and the linear actuator 30, and therefore the rigidity is improved. Furthermore, the number of chains that are provided only by serial connection is reduced, which also improves the rigidity.

Figure 15:
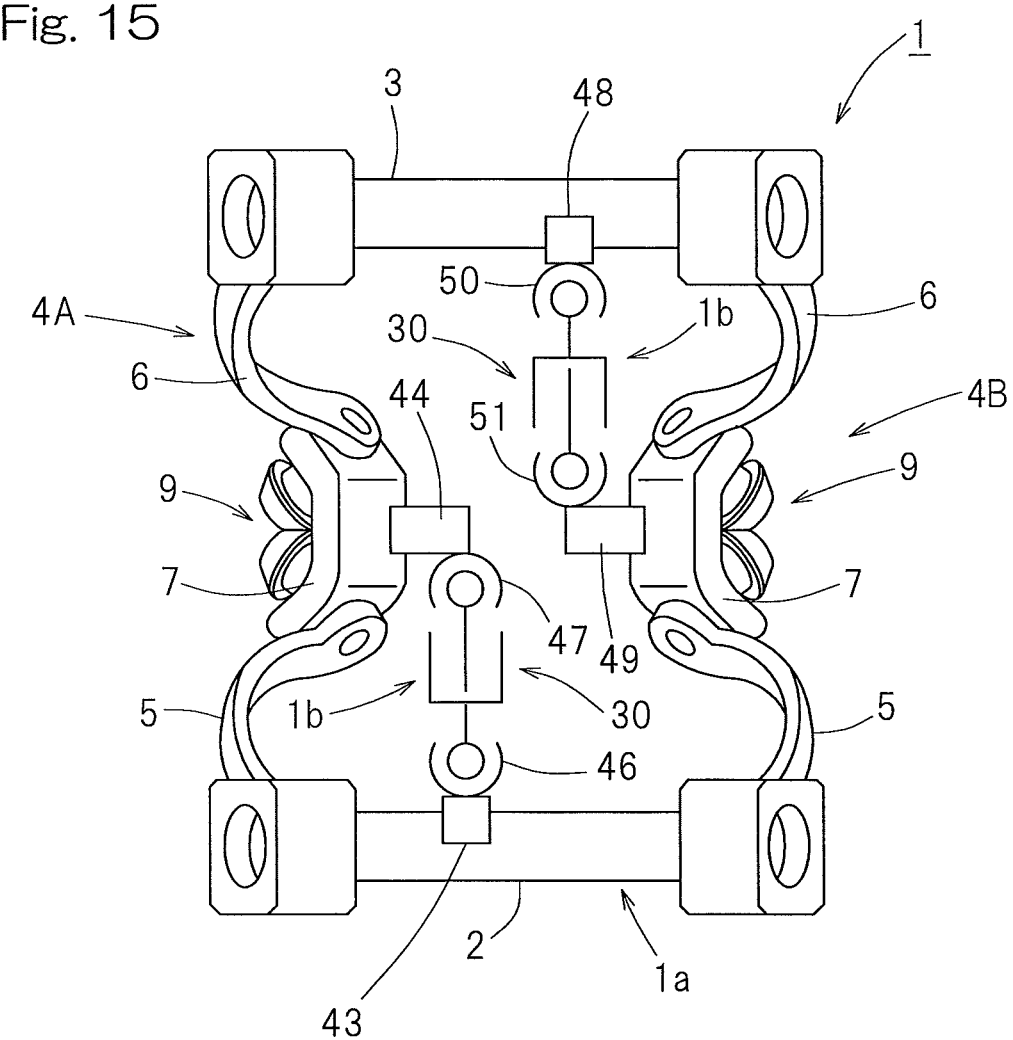
FIG. 15 is a bottom view of a link actuating device according to a sixth embodiment of the present invention.

As in a sixth embodiment shown in FIG. 15, a third auxiliary plate 43 that is provided integrally with the input side link hub 2 and a fourth auxiliary plate 44 that is provided integrally with the intermediate link 7 may be connected by a linear actuator 30 for one first link mechanism 4A, and a fifth auxiliary plate 48 that is provided integrally with the output side link hub 3 and a sixth auxiliary plate 49 that is provided integrally with the intermediate link 7 may be connected by a linear actuator 30 for the other second link mechanism 4B. Since the output side link hub 3 and the intermediate link 7 relatively move in three dimensions, connecting portions 50 and 51 between each linear actuator 30 and each of the fifth and sixth auxiliary plates 48 and 49 both constitutes spherical pairs.

Figure 16:
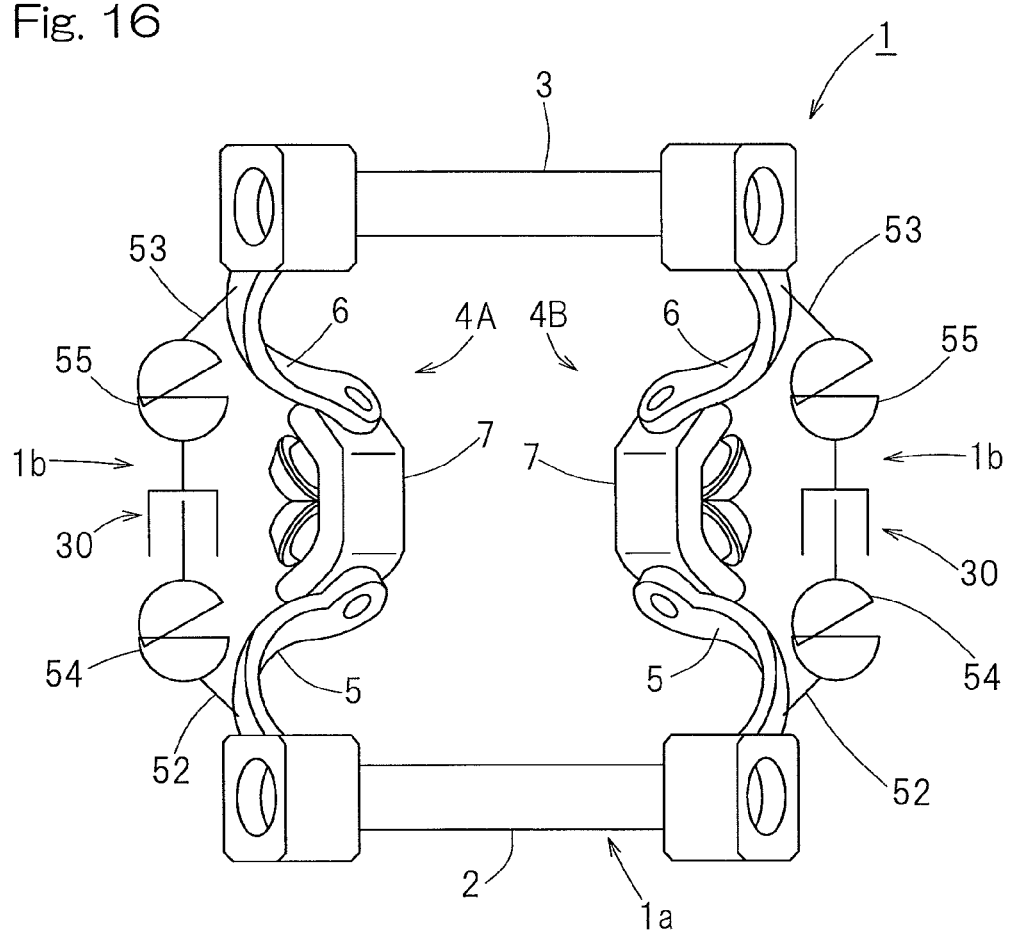
FIG. 16 is a bottom view of a link actuating device according to a seventh embodiment of the present invention.

FIG. 16 shows a seventh embodiment. With the link actuating device 1, the relative angle or position between the input side link hub 2 and the intermediate link 7 is changed by connecting a seventh auxiliary plate 52 that is provided integrally with the input side end link 5 and an eighth auxiliary plate 53 that is provided integrally with the output side end link 6 by the extendable linear actuator 30. The input side end link 5 and the output side end link 6 move in a mirror-symmetrical manner, and therefore, connecting portions 54 and 55 between the linear actuator 30 and each of the seventh and eighth auxiliary plates 52 and 53 both constitute cross joint structures.

In this seventh embodiment, the link actuating device 1 has a link configuration that is closed by the input side end link 5, the intermediate link 7, the output side end link 6 and the linear actuator 30, and therefore the rigidity is improved. Furthermore, the number of chains that are provided only by serial connection is reduced, which also improves the rigidity.

Figure 17:
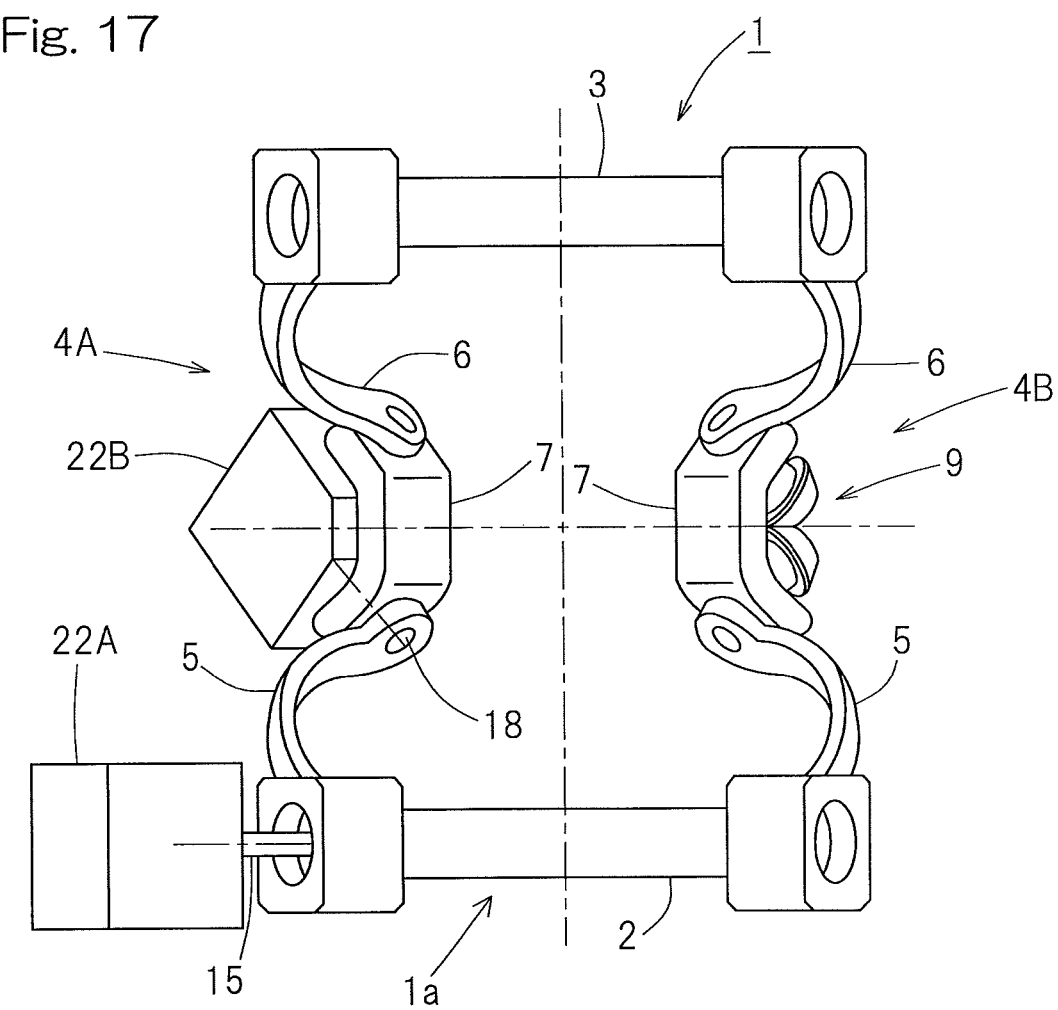
FIG. 17 is a bottom view of a link actuating device according to an eighth embodiment of the present invention.

An eighth embodiment of the present invention will be described with reference the drawings. FIG. 17 is a bottom view of a link actuating device according to the eighth embodiment. The link actuating device 1 includes a link actuating device body 1*a* and two actuators 22A and 22B that drive the link actuating device body 1*a*. The link actuating device body 1*a* will be described first. Note that as with the second embodiment, FIGS. 1, 2 to 9A to 9C used in the description of the first embodiment above can also be employed for the description of the eighth embodiment as common drawings, and the detailed description thereof has been omitted.

Figure 18:
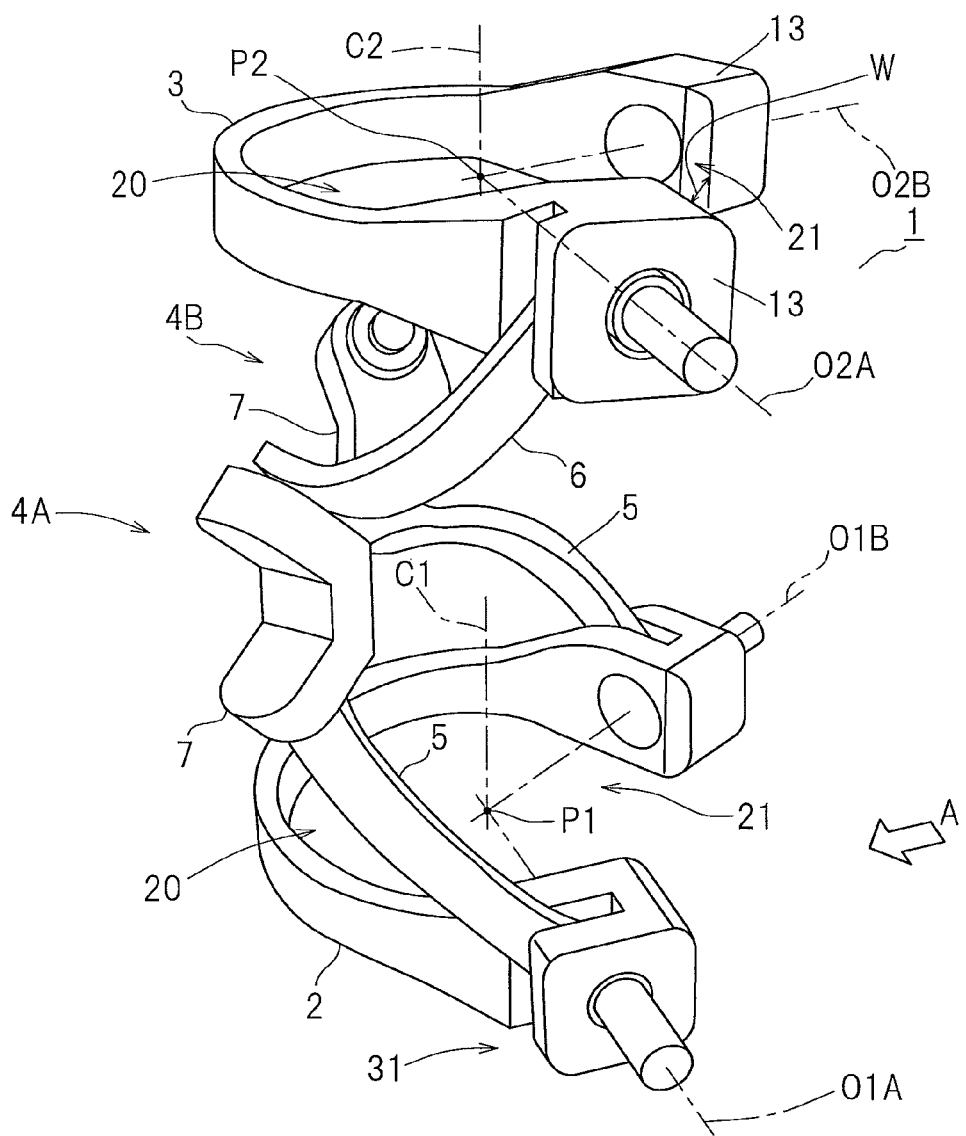
FIG. 18 is a perspective view of a link actuating device body of the link actuating device.

For the eighth embodiment, as shown in FIGS. 17 and 18, the input side end link 5 and the output side end link 6 of one second link mechanism 4B are configured to be rotationally displaced in conjunction with each other by the interlocking unit 9. The second link mechanism 4B that is provided with the interlocking unit 9 is a link mechanism that does not include actuators 22A and 22B described below.

When the link actuating device 1 is mounted around a human joint portion, the hollow portion 20 passing through in the direction of the central axes C1 and C2 shown in FIG. 18 is configured to have a size that allows insertion of an area continuous with the joint portion. The hollow portion 20 is in communication with the outside of the link hubs 2 and 3 via the opening portion 21 formed between the pair of bearing enclosing portions 13. The opening portion 21 has a width W that allows the passage of the area continuous with the joint portion.

In FIG. 17, one of the two sets of link mechanisms 4A and 4B, namely, the first link mechanism 4A is provided with the two actuators 22A and 22B. A first actuator 22A is fixed to the input side link hub 2, and rotates the rotational shaft 15 provided at the proximal end of the input side end link 5. In other words, the first actuator 22A is operable to change the rotational angle of the revolute pair between the input side link hub 2 and the input side end link 5. A second actuator 22B is fixed to the intermediate link 7, and rotates the rotational shaft 17 provided at the distal end of the input side end link 5. In other word, the second actuator 22B is operable to change the rotational angle of the revolute pair between the input side end link 5 and the intermediate link 7. The first and second actuators 22A and 22B are electric motors, for example.

The link actuating device body 1*a* is formed by connecting the input side and output side link hubs 2 and 3 by the two sets of link mechanisms 4A and 4B each having a three-link-chain structure composed of four revolute pairs. However, by setting the inter-axis angle between the respective first revolute pair axes O1A and O1B (second revolute pair axes O2A and O2B) between the input side link hub 2 (output side link hub 3) and the input side end link 5 (output side end link 6) to be other than 180° and providing, in one of the link mechanisms, namely, the second link mechanism 4B, the interlocking unit 9 that causes the input side end link 5 and the output side end link 6 to be rotationally displaced in conjunction with each other, the link actuating device body 1*a* has a structure having two degrees of freedom of rotation in which the attitude of the output side link hub 3 relative to the input side link hub 2 is uniquely determined as in the first embodiment.

By controlling the rotational angle of the input side end link 5 relative to the input side link hub 2 by the first actuator 22A provided in the first link mechanism 4A, it is possible to determine one degree of freedom of rotation of the two degrees of freedom of rotation with which the attitude of the output side link hub 3 relative to the input side link hub 2 is determined. Additionally, by controlling the rotational angle of the intermediate link 7 relative to the input side end link 5 by the second actuator 22B, it is possible to determine the rotational attitude of the remaining one degree of freedom.

When the input side and output side end links 5 and 6 are equal in angle and length and have the same geometric shape on the input side and the output side, and the input side and the output side of intermediate links 7 have the same geometric shape in the two sets of link mechanisms 4A and 4B as in this eighth embodiment, the input side link hub 2 and the input side end link 5, and the output side link hub 3 and the output side end link 6 move in the same manner due to the geometric symmetry by setting the angle positional relationship between the intermediate link 7 and the input side and output side end links 5 and 6 relative to the plane of symmetry of the intermediate link 7 to be equal on the input side and the output side.

Since the opening portion 21 in communication with the outside of the input side and output side link hubs 2 and 3 is provided in the hollow portion 20 of the input side and output side link hubs 2 and 3, the human limbs or the like can be easily placed in the hollow portion 20. Since the number of sets of link mechanisms is two, it is possible to ensure a relatively large circumferential range in which no portion of the two sets of link mechanisms 4A and 4B is located regardless of the attitude of the output side link hub 3 relative to the input side link hub 2 within a possible range. Accordingly, the contact between the body and the link mechanisms 4A and 4B can also be easily prevented.

Furthermore, since both of the actuators 22A and 22B are provided in the first link mechanism 4A, the actuators 22A and 22B and the components therearound are concentrated on the side of the first link mechanism 4A when viewed from the hollow portion 20 in the outer diameter direction (arrow A of FIG. 18). Thus, at the time of mounting the link actuating device 1 around a human joint portion, the link mechanisms or the like can be prevented from coming into contact with the patient body by mounting the link actuating device 1 such that the side of the first link mechanism 4A in which the actuators 22A and 22B are provided is positioned away from the body.

Figure 19:
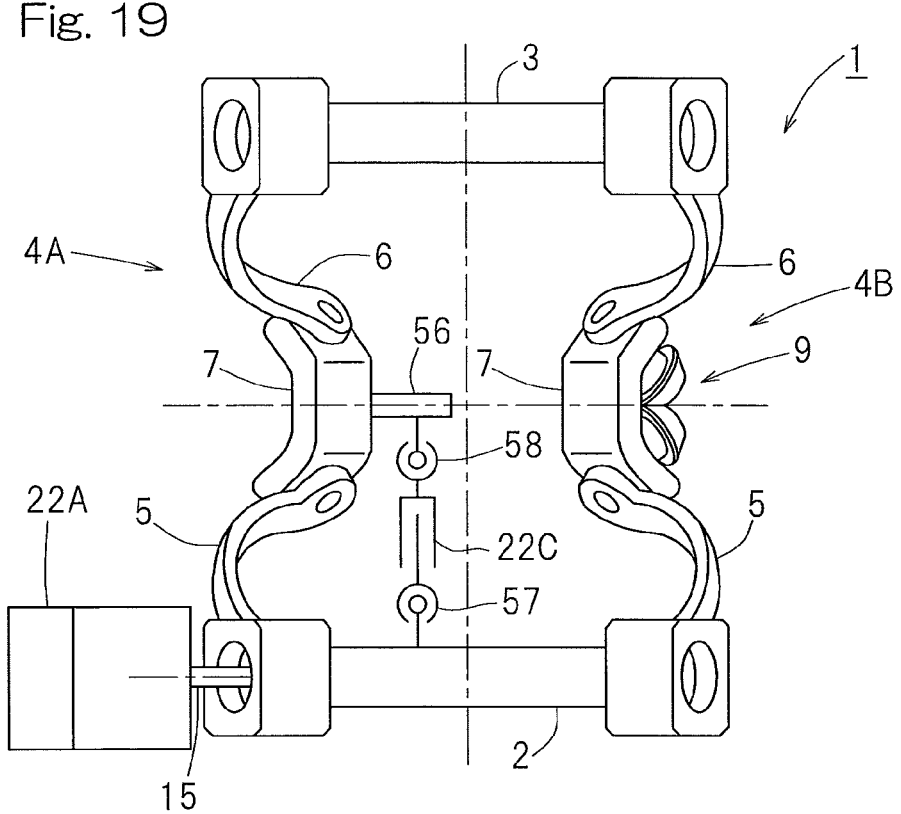
FIG. 19 is a bottom view of a link actuating device according to a ninth embodiment of the present invention.

FIG. 19 shows a ninth embodiment. In the link actuating device 1 as well, one set of the first link mechanism 4A is provided with two actuators 22A and 22C. The first actuator 22A is operable to change the rotational angle of the revolute pair between the input side link hub 2 and the input side end link 5 as described above. The third actuator 22C is a linear actuator whose opposite ends are connected to the input side link hub 2 and an attachment member 56 integral with the intermediate link 7, and that performs extension or contraction operation in the linear direction. In other words, the third actuator 22C is operable to change the relative distance between the input side link hub 2 and the intermediate link 7. A connecting portion 57 between the input side link hub 2 and the third actuator 22C and a connecting portion 58 between the attachment member 56 and the third actuator 22C both constitutes spherical pairs. As the third actuator 22C that is a linear actuator, it is possible to use, for example, a mechanism using a ball screw or a hydraulic cylinder device.

The attitude of the output side link hub 3 relative to the input side link hub 2 can be arbitrarily changed with two degrees of freedom in the rotational direction also by providing the two actuators 22A and 22C in this way. When the third actuator 22C that arbitrarily changes the relative distance between the input side link hub 2 and the intermediate link 7 is a linear actuator, a link configuration is achieved that is closed by the input side link hub 2, the input side end link 5, the intermediate link 7 and the third actuator 22C, so that load acting on the first link mechanism 4A is received by the third actuator 22C. Accordingly, the rigidity of the link actuating device 1 is improved.

Figure 20:
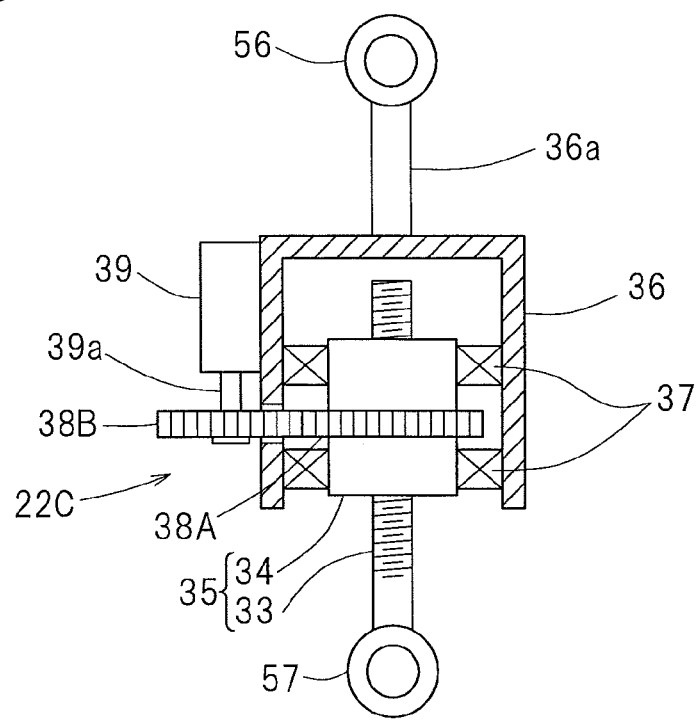
FIG. 20 is a vertical cross-sectional view showing an example of an actuator of the link actuating device.

FIG. 20 shows an exemplary linear actuator using a ball screw. The third actuator 22C that is a linear actuator includes a nut 34 threadably engaged with a screw shaft 33 whose one end is connected to the input side link hub 2 (FIG. 19), and the screw shaft 33 and the nut 34 constitute a ball screw 35. The nut 34 is rotatably supported by two bearings 37 on an outer cylinder body 36 that is connected to the other attachment member 56 (FIG. 19) via a rod 36a. A first spur gear 38A is provided on the outer circumference of the nut 34, and another second spur gear 38B is meshed with the first spur gear 38A. The other second spur gear 38B is attached to an output shaft 39a of a motor 39 that is installed on the outer circumference of the outer cylinder body 36. By rotating the motor 39, the nut 34 is rotated via the first and second spur gears 38A and 38B, and the screw shaft 33 is advanced or retracted relative to the nut 34 by the ball screw 35. This changes the distance between the distal end of the screw shaft 33 and the distal end of the rod 36a. In other words, the third actuator 22C extends or contracts.

Figure 21:
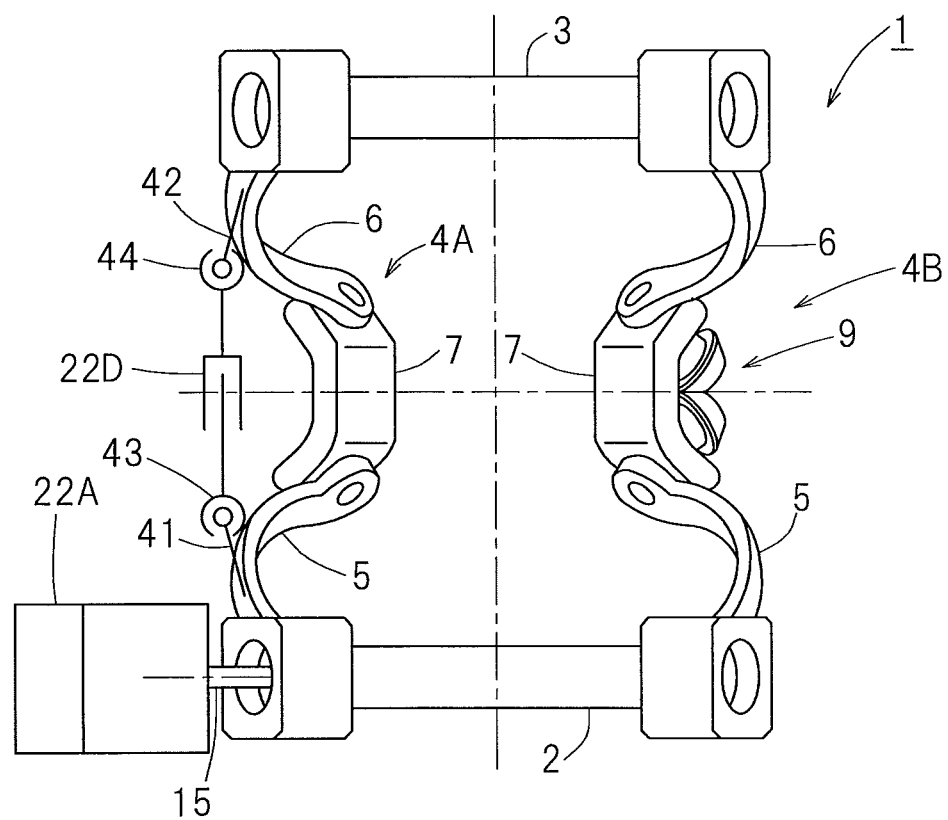
FIG. 21 is a bottom view of a link actuating device according to a tenth embodiment of the present invention.

FIG. 21 shows a tenth embodiment. In the link actuating device 1 as well, one set of the first link mechanism 4A is provided with two actuators 22A and 22D. The first actuator 22A is operable to change the rotational angle of the revolute pair between the input side link hub 2 and the input side end link 5 as described above. The fourth actuator 22D is a linear actuator whose opposite ends are connected to an attachment member 41 integral with the input side end link 5 and an attachment member 42 integral with the output side end link 6, and that performs extension or contraction operations in the linear direction. In other words, the fourth actuator 22D is operable to change the relative distance between the input side end link 5 and the output side end link 6. A connecting portion 43 between the attachment member 41 and the fourth actuator 22D and a connecting portion 44 between the attachment member 42 and the fourth actuator 22D both constitute spherical pairs.

The attitude of the output side link hub 3 relative to the input side link hub 2 can be arbitrarily changed with two degrees of freedom in the rotational direction also by providing the two actuators 22A and 22D in this way. When the fourth actuator 22D that changes the relative distance between the input side and output side end links 5 and 6 is a linear actuator, a link configuration is achieved that is closed by the input side end link 5, the intermediate link 7, the output side end link 6 and the fourth actuator 22D, so that load acting on the first link mechanism 4A is received by the fourth actuator 22D. Accordingly, the rigidity of the link actuating device 1 is improved.

Figure 22A:
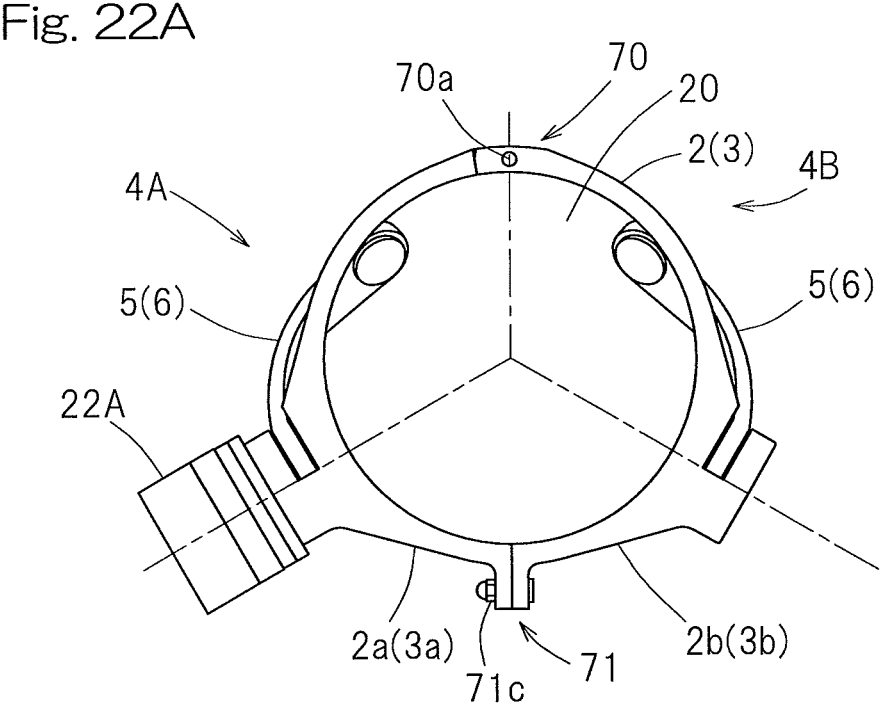
FIG. 22A is a diagram showing a state of a link hub having a different configuration.
Figure 22B:
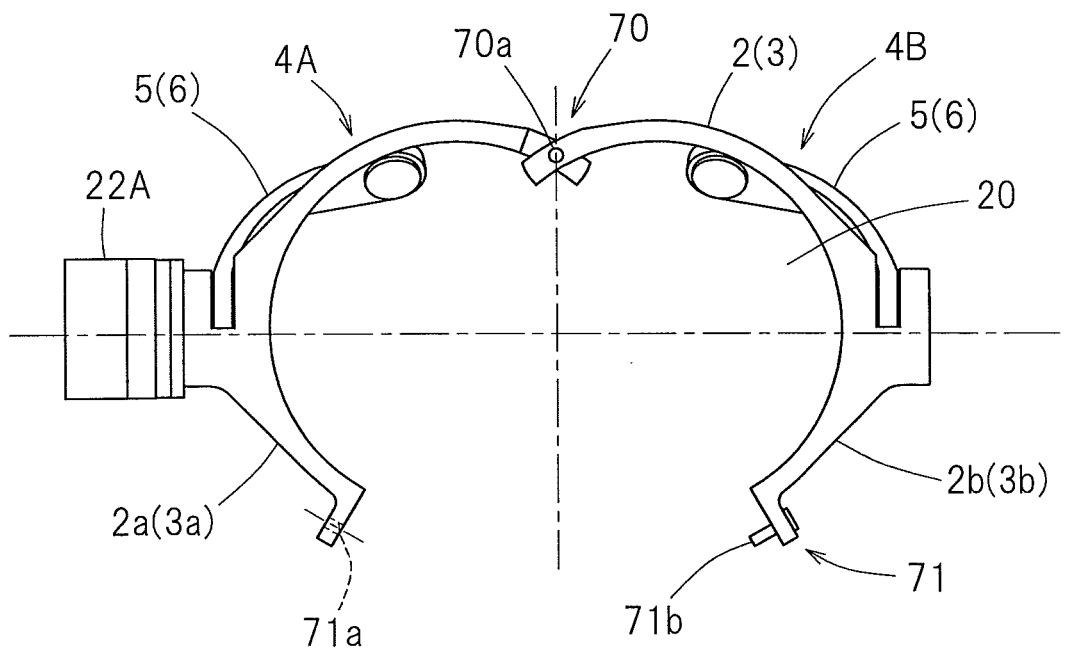
FIG. 22B is a diagram showing a different state of the link hub.

FIGS. 22A and 22B show a different configuration of a link hub. The input side link hub 2 (output side link hub 3) is divided into two input side link hub halves 2a and 2b (output side link hub halves 3a and 3b) arranged along the outer circumference of the hollow portion 20 in the circumferential direction. The input side end link 5 (output side end link 6) of one of the two sets of link mechanisms 4A and 4B is rotatably connected to each of the two input side link hub halves 2a and 2b (output side link hub halves 3a and 3b). The two input side link hub halves 2a and 2b (output side link hub halves 3a and 3b) are coupled to each other by first and second coupling portions 70 and 71.

One first coupling portion 70 has a hinge structure, and the two input side link hub halves 2a and 2b (output side link hub halves 3a and 3b) are pivotable relative to each other about a fulcrum shaft 70a. The other second coupling portion 71 is configured such that the two input side link hub halves 2a and 2b (output side link hub halves 3a and 3b) are coupled to each other by inserting, to a bolt hole 71a formed in one input side link hub half 2a (one output side link hub half 3a), a bolt 71b provided in the other input side link hub half 2b (other output side link hub half 3b), and fastening a nut 71c to the bolt 71b. By pivoting the input side link hub halves 2a and 2b (output side link hub halves 3a and 3b) about the fulcrum shaft 70a, it is possible to achieve a state in which the hollow portion 20 is open on the side of the second coupling portion 71 as shown in FIG. 22B and a state in which the hollow portion 20 is closed as shown in FIG. 22A.

By dividing the input side link hub 2 (output side link hub 3) into the two input side link hub halves 2a and 2b (output side link hub halves 3a and 3b) in this way, the area continuous with the joint portion can be easily placed into the hollow portion 20. Since the two input side link hub halves 2a and 2b (output side link hub halves 3a and 3b) can be coupled to each other by the first and second coupling portions 70 and 71, the link actuating device 1 can be mounted around the joint portion safely and easily. By configuring one of the two coupling portions 70 and 71, namely, the first coupling portion 70 so as to have a hinge structure, the two input side link hub halves 2a and 2b (output side link hub halves 3a and 3b) will not be separated, and thus ease of handling is improved.

Figure 23:
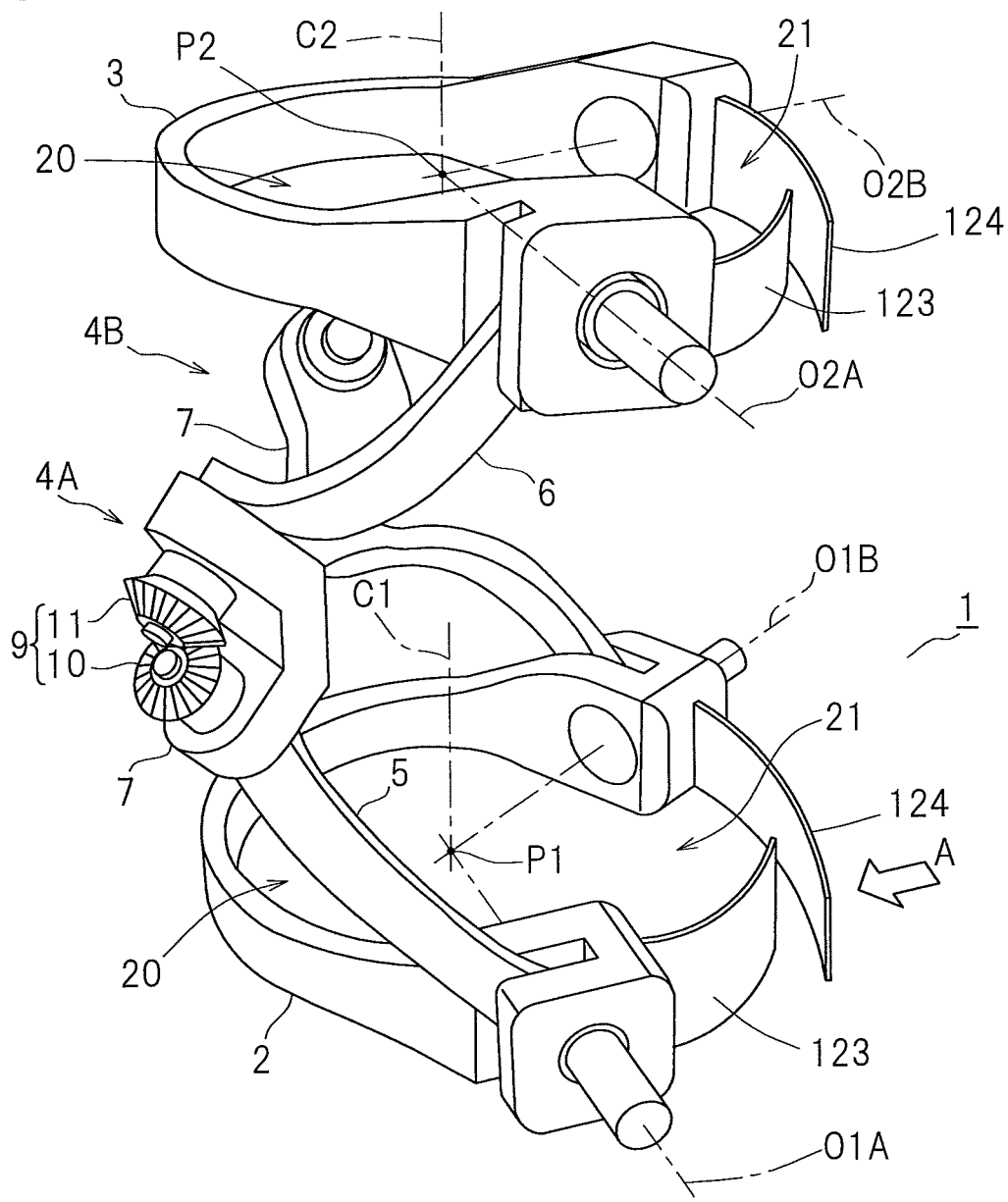
FIG. 23 is a perspective view of a limb joint portion mounted apparatus according to an eleventh embodiment of the present invention.
Figure 24:
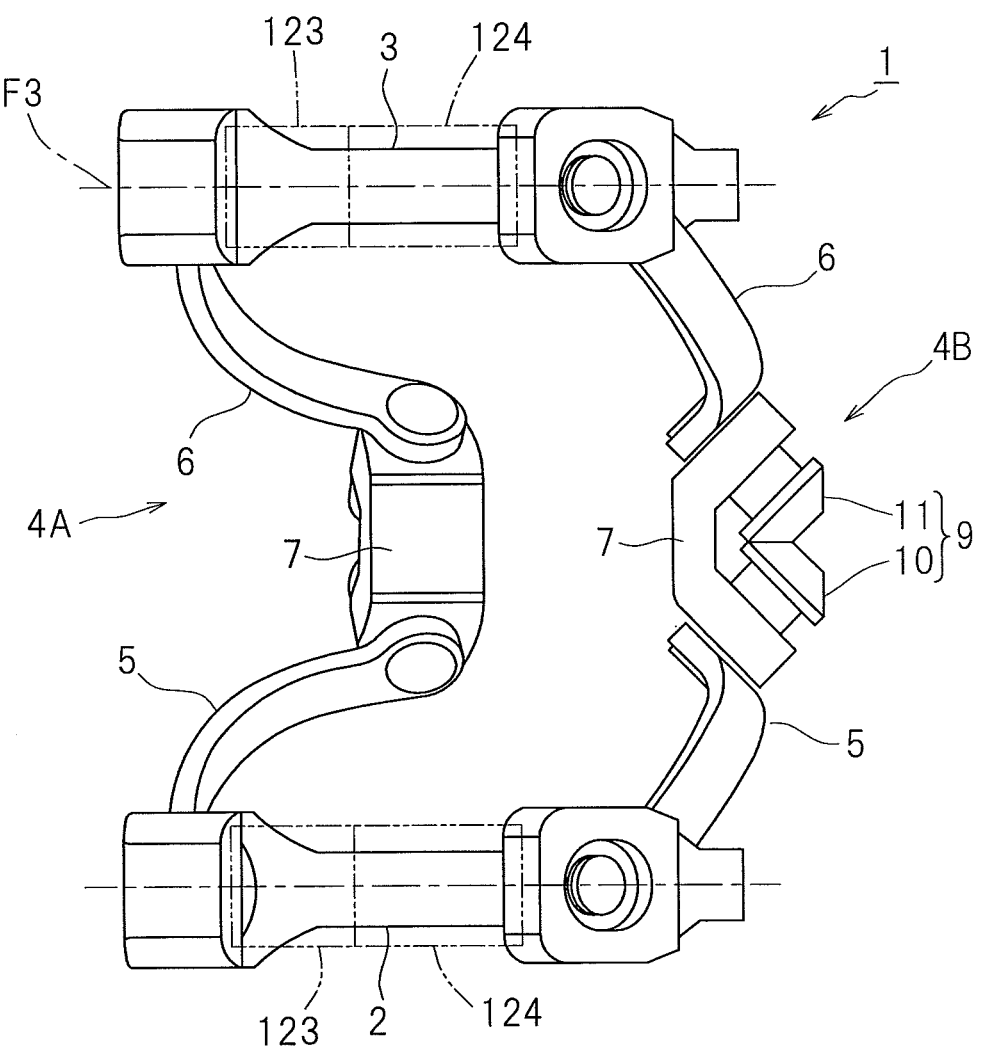
FIG. 24 is a view taken in the direction of the arrow A in FIG. 23.

An eleventh embodiment of the present invention will be described with reference to FIGS. 23 to 28. FIGS. 23 and 24 are perspective views of a limb joint portion mounted apparatus according to the eleventh embodiment viewed from different angles. Note that the basic configuration of a partially broken exploded view in a state in which the limb joint portion mounted apparatus is exploded is the same as that of FIG. 1 showing the first embodiment described above, and the illustration thereof has been omitted. As shown in FIG. 23, the basic configuration of a link actuating device 1 constituting the limb, joint portion mounted apparatus is similar to that of the first embodiment shown in FIG. 1, but is different in that the input side link hub 2 has a pair of first and second mounting belts 123 and 124, which will be described later.

Figure 25:
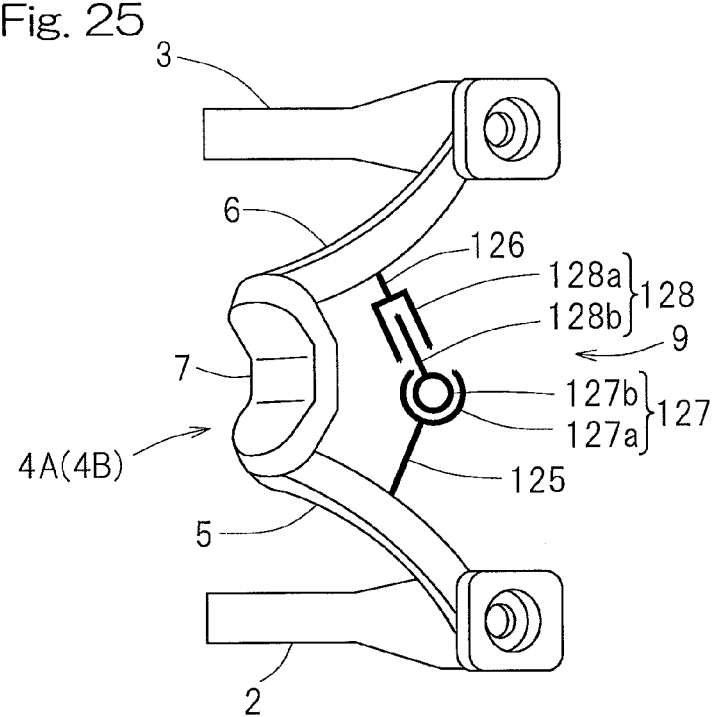
FIG. 25 is a diagram showing a different configuration of interlocking unit.

FIG. 25 shows different interlocking unit. In the interlocking unit 9, the input side and output side end links 5 and 6 are integrally provided with first and second auxiliary arms 125 and 126, respectively, and the auxiliary arms 125 and 126 are coupled to each other via a spherical pair 127 and a prismatic pair 128. The spherical pair 127 is a pair in which a pair of pair components 127a and 127b move along a spherical surface relative to each other. The prismatic pair 128 is a pair in which a pair of pair components 128a and 128b move in the linear direction relative to each other. By the interlocking unit 9 as well, the position of the output side end link 6 is determined in correspondence with the position of the input side end link 5. However, the input side end link 5 and the output side end link 6 do not move symmetrically with respect to the central portion of the intermediate link 7.

The size of the cross section parallel to the input side and output side planes F2 and F3 of the hollow portion 20 is a size that allows insertion of the area continuous with the limb joint portion, which is the affected area. The hollow portion 20 is in communication with the outside of the link hubs 2 and 3 via the opening portion 21 formed between the pair of bearing enclosing portions 13. The width W of the opening portion 21 is a width that allows passage of the area continuous with the limb joint portion. For both of the input side and output side link hubs 2 and 3, the opening portion 21 is located on the same side with respect to the respective revolute pair axes O1A, O1B, O2A, and O2B. That is, as shown in FIG. 23, the opening portions 21 of the input side and output side link hubs 2 and 3 face the same side in the attitude in which the input side link hub 2 and the output side link hub 3 are parallel to each other.

As shown in FIG. 23, first and second mounting belts 123 and 124 that can be mutually coupled are respectively attached to both ends of the link hubs 2 and 3 located across the opening portion 21. Although the pair of mounting belts 123 and 124 are coupled using a hook-and-loop fastener, including, for example, Magic Tape (registered trademark), they may be coupled using another method. Preferably, the mounting belts 123 and 124 are made of a flexible material.

The specific operations of a link actuating device 1 serving as the limb joint portion mounted apparatus are the same as those of the link actuating device according to the first embodiment described above, and the detailed description thereof has been omitted.

Figure 26:
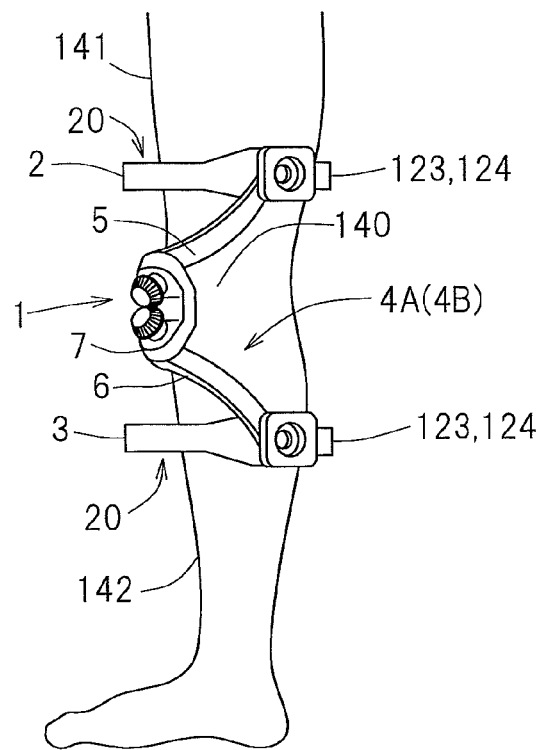
FIG. 26 is a diagram showing an exemplary usage state of the limb joint portion mounted apparatus.

The link actuating device 1 serving as the limb joint mounted apparatus is mounted around a limb joint portion for the purposes of rehabilitation, movement assistance and the like for the limb joint portion. For example, FIG. 26 shows a state in which the link actuating device 1 is mounted around a knee joint 140. In this case, the pair of mounting belts 123 and 124 of the input side and output side link hubs 2 and 3 are coupled to each other in a state in which the knee joint 140 is located between the input side and output side link hubs 2 and 3 and the area continuous with the knee joint 140, namely, a thigh portion 141 and a crus portion 142 are inserted through the hollow portions 20 of the input side and output side link hubs 2 and 3.

The bending angle and the angle in the varus and valgus directions of the knee joint 140 can be adjusted by adjusting each of the rotational angles of the revolute pairs in the two sets of link mechanisms 4A and 4B in a state in which the link actuating device 1 serving as the limb joint mounted apparatus is mounted. Also, the bending angle and the angles in the varus and valgus directions described above can be fixed by fixing the rotational angles of the revolute pairs of the link mechanisms 4A and 4B. By adjusting or fixing various angles of the knee joint 140 in this way, it is possible to cope with varying angular differences depending on the physical characteristics of the patient and the condition of the affected area. The input side and output side link hubs 2 and 3 receive the load on both sides of the knee joint 140, which is the affected area, and it is therefore possible to reduce the load on the knee joint 140.

Figure 27:
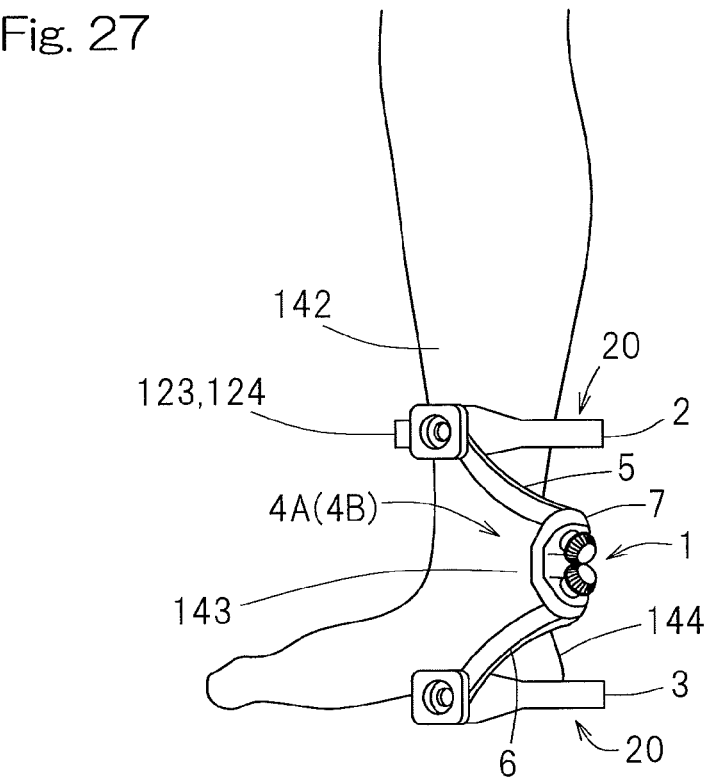
FIG. 27 is a diagram showing a different usage state of the limb joint portion mounted apparatus.

FIG. 27 shows a state in which the link actuating device 1 serving as the limb joint mounted apparatus is mounted around an ankle joint 143. In this case, the ankle joint 143 is located between the input side and output side link hubs 2 and 3 and the crus portion 142 is inserted through the hollow portion 20 of the input side link hub 2. A heel 144 is fitted to the hollow portion 20 of the output side link hub 3.

Then, the pair of mounting belts 123 and 124 of the input side link hub 2 are coupled, thereby attaching the link actuating device 1 serving as the limb joint mounted apparatus around the ankle joint 143. As in the case of the knee joint 140, the bending angle and the angles in the supination and pronation directions of the ankle joint 143 can be adjusted or fixed by adjusting the rotational angles or fixing the rotation of the revolute pairs of the link mechanisms 4A and 4B.

Figure 28:
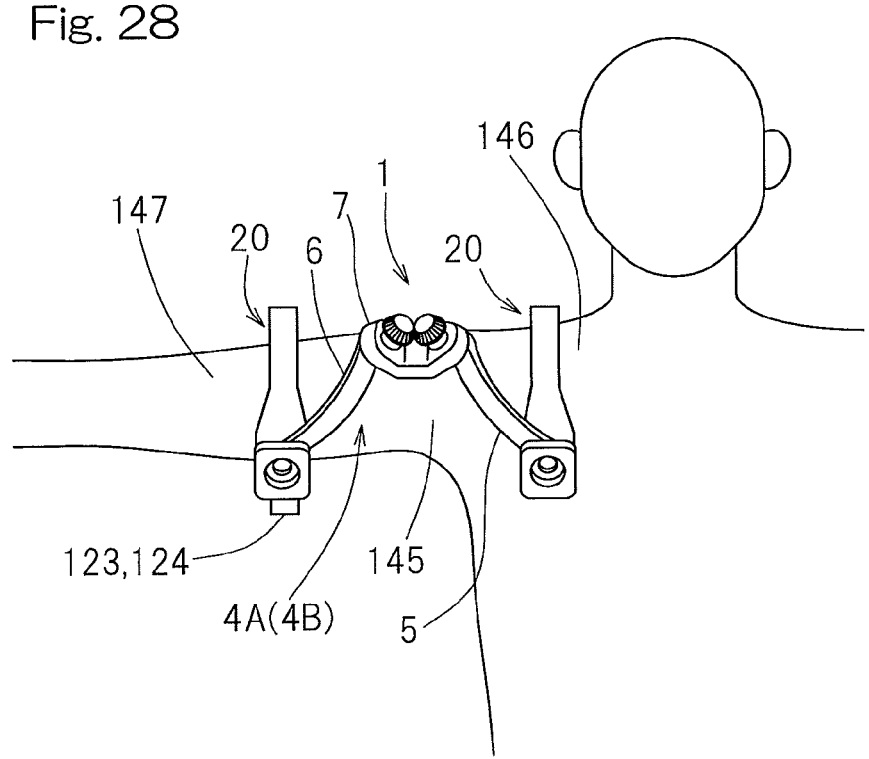
FIG. 28 is a diagram showing another different usage state of the limb joint portion mounted apparatus.

FIG. 28 shows a state in which the link actuating device 1 serving as the limb joint mounted apparatus is mounted around a shoulder joint 145. In this case, the shoulder joint 145 is located between the input side and output side link hubs 2 and 3, and a shoulder 146 is fitted into the hollow portion 20 of the input side link hub 2, and an upper arm portion 147 is inserted through the hollow portion 20 of the output side link hub 3. Then, the pair of mounting belts 123 and 124 of the link hub 3 are coupled, thereby mounting the link actuating device 1 serving as limb joint mounted apparatus around the shoulder joint 145. By adjusting the rotational angles or fixing the rotation of the revolute pairs of the link mechanisms 4A and 4B, it is possible to adjust or fix the turning angle of the shoulder joint 145.

With the above-described configuration, the opening portion 21 in communication with the outside of the input side and output side link hubs 2 and 3 is provided in the hollow portions 20 of the input side and output side link hubs 2 and 3, and therefore the area continuous with the limb joint portion can be easily inserted through the hollow portions 20.

Figure 29:
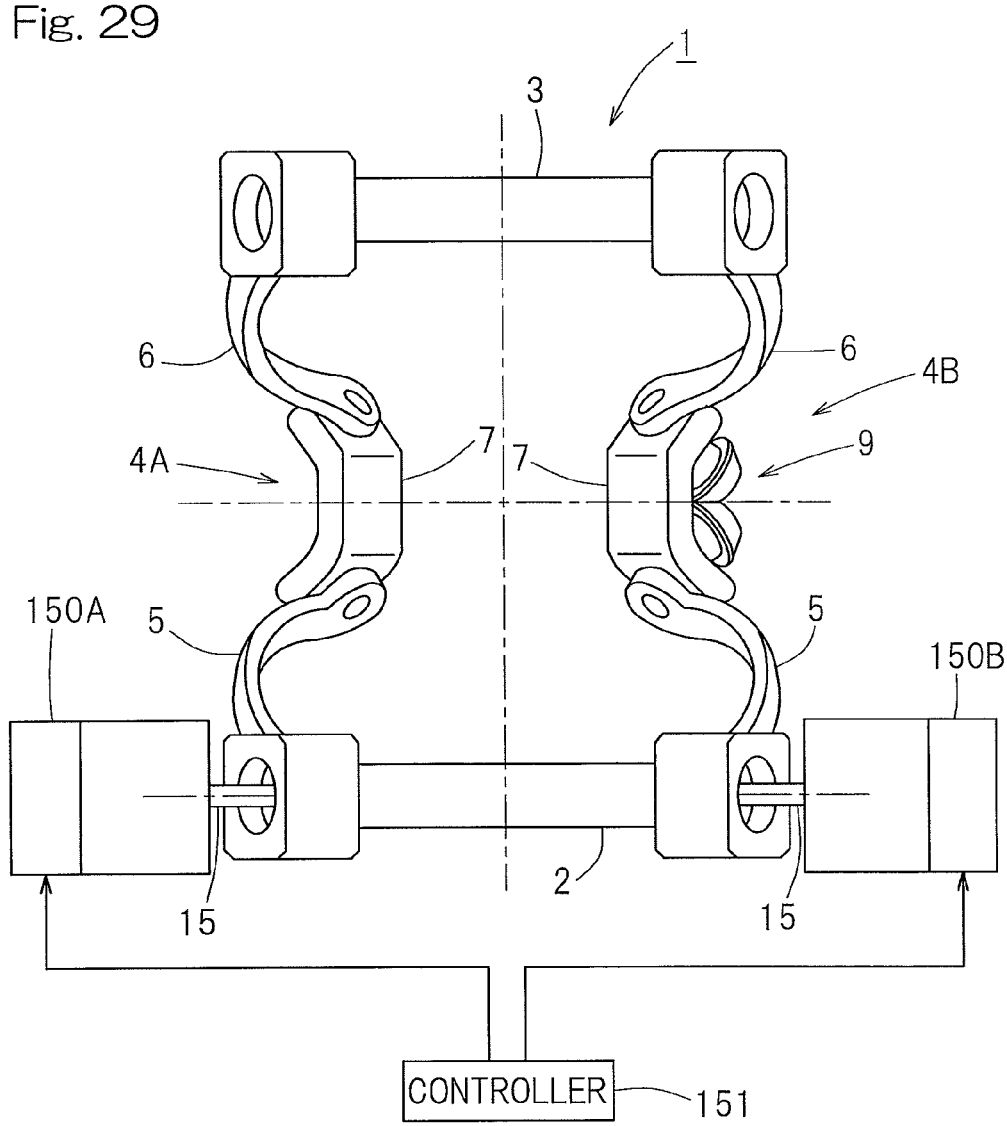
FIG. 29 is a front view of a limb joint portion mounted apparatus according to a twelfth embodiment of the present invention.

FIG. 29 shows a limb joint portion mounted apparatus according to a twelfth embodiment. In a link actuating device 1 serving as the limb joint portion mounted apparatus, actuators 150A and 150B capable of arbitrarily changing the angle of the input side end link 5 relative to the input side link hub 2 are respectively provided in both of the first and second link mechanisms 4A and 4B. The actuators 150A and 150B are, for example, rotary actuators or motors, and rotate the input side end link 5 by rotationally driving the rotational shaft 15. The locations of installation of the actuators 150A and 150B are not limited to the above-described locations, and may be any location so long as the relative rotation angular displacement of at least one of the four revolute pairs of the link mechanisms 4A and 4B can be changed. Each of the actuators 150A and 150B is controlled by a controller 151. Since the first and second link mechanisms 4A and 4B have the same geometric shape, they can be easily controlled. Note that in the illustrated example, the interlocking unit 9 is provided only in one of the link mechanisms, namely the second link mechanism 4B.

For example, the controller 151 controls the actuators 150A and 150B such that the limb joint portion, to which the link actuating device 1 serving as the limb joint portion mounted apparatus is mounted, is moved within a movable range. By driving the actuators 150A and 150B so as to forcibly change the attitude of the output side link hub 3 relative to the input side link hub 2, it is possible to perform rehabilitation exercises in which the limb joint portion is moved within the movable range. The link actuating device 1 serving as the limb joint portion mounted apparatus is a mechanism capable of two degrees of freedom of rotation. Accordingly, when mounted around, for example, the knee joint 40 as shown in FIG. 26, can be given not only simple bending and stretching of the knee joint 40, but also an angular change in the varus and valgus directions according to the condition of the patient. Accordingly, movements (rolling, sliding, and turning) within the joint capsule are increased, and many muscles around the limb joint portion can be moved effectively, thus achieving effective rehabilitation exercises. As a result, the recuperative period can be shortened. Additionally, the burden on physiotherapists can be reduced.

The controller 151 may control the actuators 150A and 150B so as to assist the movements within the movable range of the limb joint portion around which the link actuating device 1 serving as the limb joint portion mounted apparatus is mounted. In this case, the movement of the limb joint portion can be assisted by driving the actuators 150A and 150B so as to adjust the movable range and the movable speed of the output side link hub 3 relative to the input side link hub 2.

Figure 30:
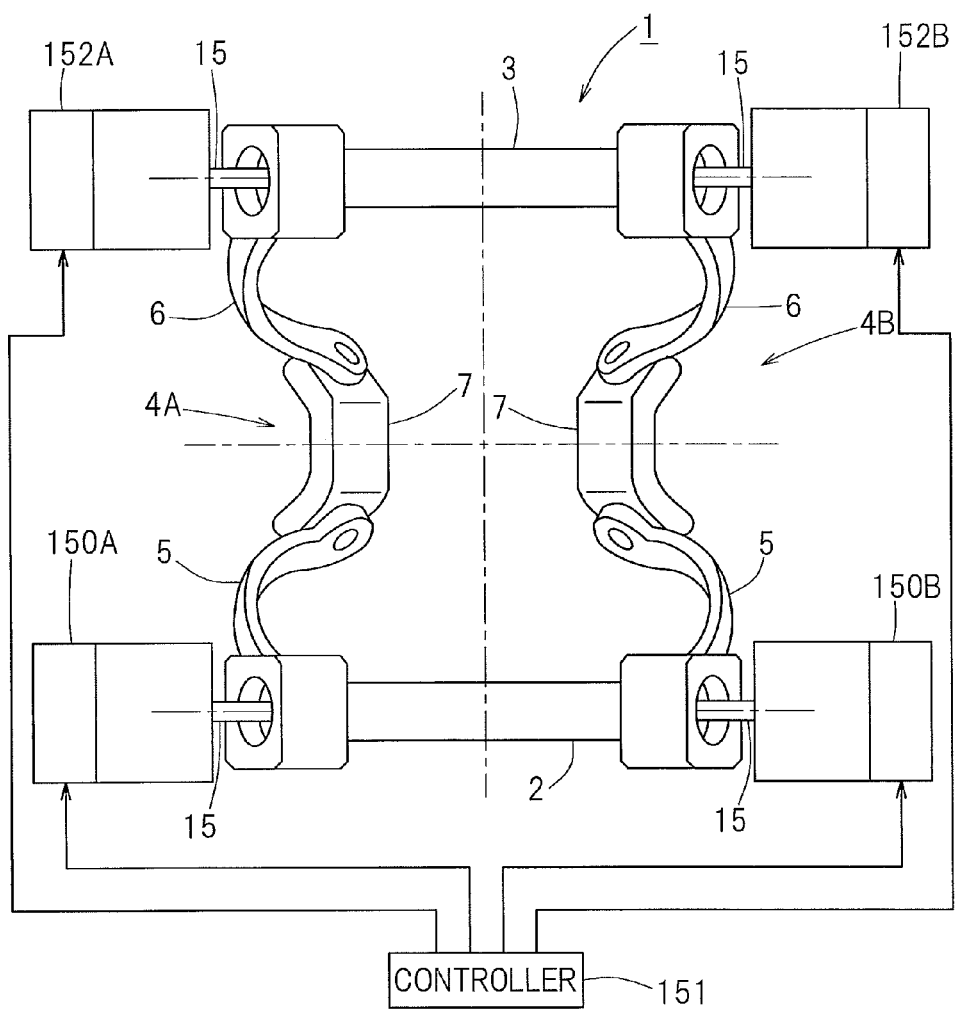
FIG. 30 is a front view of a limb joint portion mounted apparatus according to a thirteenth embodiment of the present invention.

FIG. 30 shows a limb joint portion mounted apparatus according to a thirteenth embodiment. In a link actuating device 1 serving as the limb joint portion mounted apparatus, actuators 152A and 152B capable of arbitrarily changing the angle of the output side end link 6 relative to the output side link hub 3 are respectively provided in both of the first and second link mechanisms 4A and 4B, in addition to the actuators 150A and 150B capable of arbitrarily changing the angle of the input side end link 5 relative to the input side link hub 2. The actuators 152A and 152B are, for example, motors or rotary actuators, and rotate the output side end link 6 by rotationally driving the rotational shaft 15. The actuators 152A and 152B are also controlled by the controller 151. When the actuators 150A, 150B, 152A, and 152B are installed at a total of four locations of the connecting portions between the input side and output side link hubs 2 and 3 and the input side and output side end links 5 and 6 in this way, the load on each of the actuators is reduced. Accordingly, the actuator can be reduced in size, and the device as a whole can be made compact. Since the angles of all of the input side and output side end links 5 and 6 can be determined by the four actuators 150A, 150B, 152A, and 152B, it is not necessary to provide the interlocking unit 9.

Figure 31:
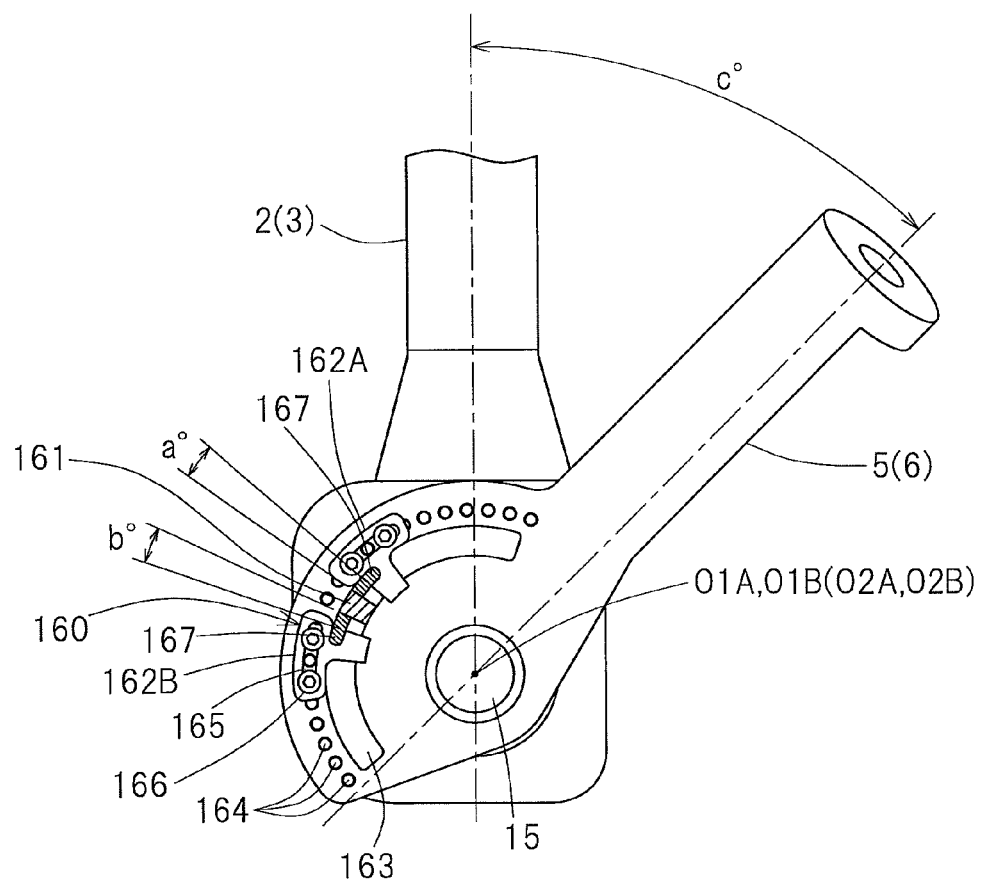
FIG. 31 is a diagram showing an example of a limiter.

FIG. 31 shows a different configuration of a connecting portion between a link hub and an end link. The connecting portion is provided with a limiter 160 that limits the relative rotation angular displacement between a revolute pair between an input side link hub 2 (output side link hub 3) and an input side end link 5 (output side end link 6). The limiter 160 includes a stopper 161 provided in the input side link hub 2 (output side link hub 3) and a pair of stopper receivers 162A and 162B provided in the input side end link 5 (output side end link 6).

The stopper 161 is a columnar member protruding from the end face of the input side link hub 2 (output side link hub 3) toward the input side end link 5 (output side end link 6), and is passed through an arc-shaped slot 163 formed in the input side end link 5 (output side end link 6). The slot 163 has the shape of an arc about the first revolute pair axis O1A or O1B (second revolute pair axis O2A or O2B) between the input side link hub 2 (output side link hub 3) and the input side end link 5 (output side end link 6).

The stopper receivers 162A and 162B are respectively disposed on both sides in the circumferential direction across the stopper 161 and are attached such that their circumferential positions can be changed relative to the input side end link 5 (output side end link 6). More specifically, a plurality of screw holes 164 along the slot 163 are provided in the input side end link 5 (output side end link 6), and by selectively screwing bolts 166 inserted through a bolt insertion hole 165 of the stopper receivers 162A and 162B into any of the plurality of screw holes 164, the stopper receivers 162A and 162B are attached to the input side end link 5 (output side end link 6) such that their circumferential positions can be changed. To prevent the stopper receivers 162A and 162B from moving, two bolts 166 are used to attach one stopper receiver 162A or 162B to the input side end link 5 (output side end link 6). In the illustrated example, the bolt insertion hole 165 is used as a common slot for two bolts 166, but the bolt insertion hole 165 may be provided for each bolt 166.

The stopper receivers 162A and 162B are each provided with a damper 167 on the surface thereof facing the stopper 161. The damper 167 is made of a spring element material such as rubber, and acts to elastically limit the relative rotation angular displacement of the revolute pair between the input side link hub 2 (output side link hub 3) and the input side end link 5 (output side end link 6).

In a state in which the respective dampers 167 of the stopper receivers 162A and 162B are in contact with both side of the stopper 161 as shown in the drawing, when the angle between the input side link hub 2 (output side link hub 3) and the input side end link 5 (output side end link 6) is c°, the angle between the stopper 161 and the stopper receiver 162A is a°, and the angle between the stopper 161 and the stopper receiver 162B is b°, the variable angle range of the input side end link 5 (output side end link 6) relative to the input side link hub 2 (output side link hub 3) is expressed by $(c-a)°$ to $(c+b)°$.

By limiting the relative rotation angular displacement of the revolute pair between the input side link hub 2 (output side link hub 3) and the input side end link 5 (output side end link 6) by the limiter 160, the movable range of the output side link hub 3 relative to the input side link hub 2 is limited. As a result, the movable range of the limb joint portion, to which the link actuating device 1 serving as the limb joint portion mounted apparatus is mounted, is also limited. By changing the settings of the limiter 160, the movable range can be easily adjusted according to the condition of the limb joint portion, which is the affected area. When impact force is applied to the limb, load is abruptly applied to the limb in contact with the input side link hub 2 (output side link hub 3). However, the abrupt change in load is reduced by the damper 167, making it possible to reduce the burden on the limb.

Figure 32A:
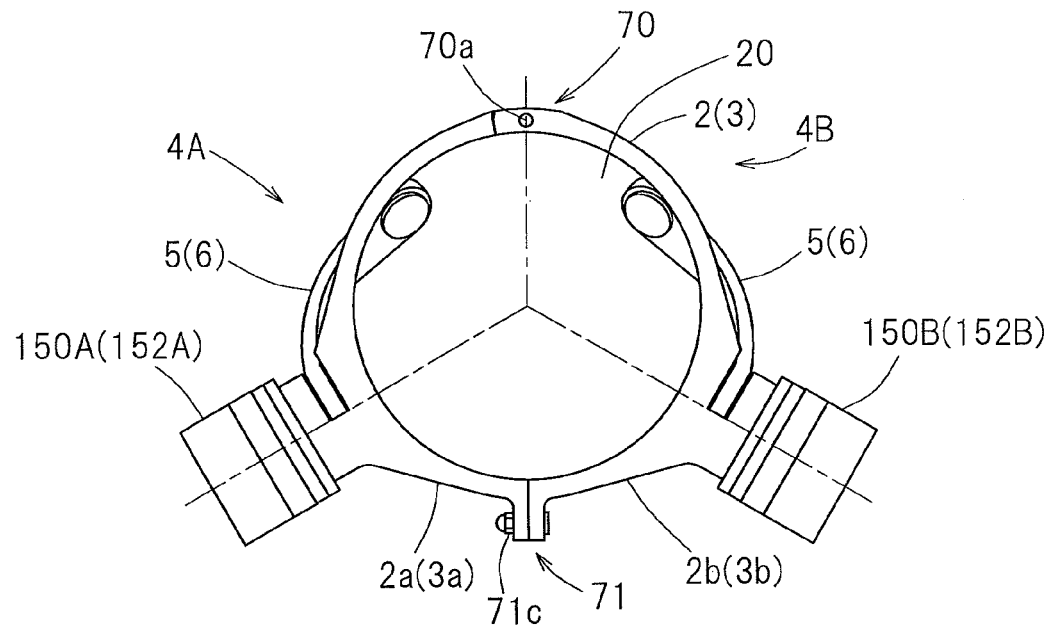
FIG. 32A is a diagram showing a state of a link hub having a different configuration.
Figure 32B:
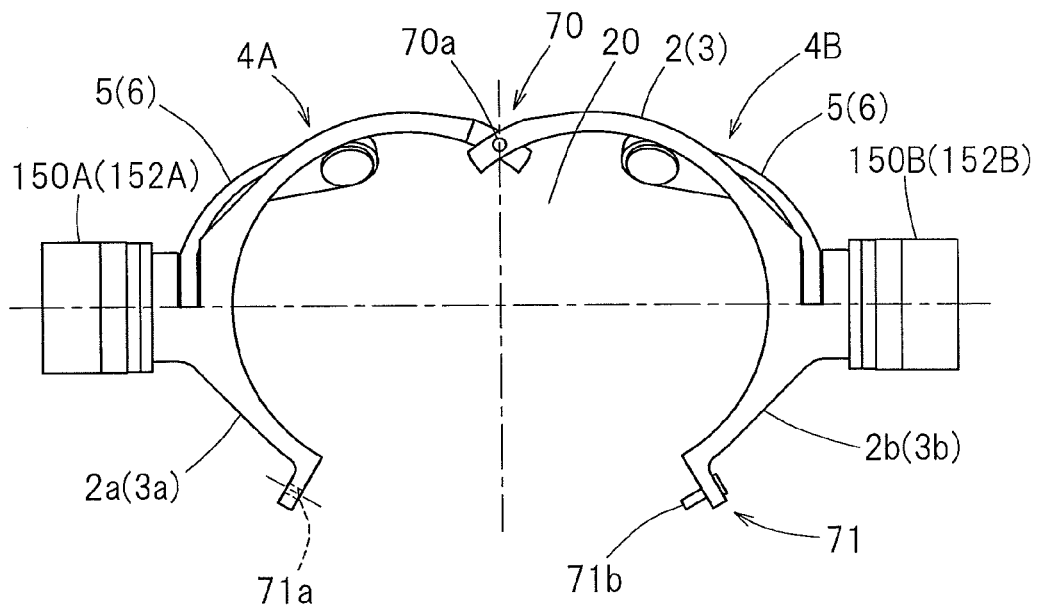
FIG. 32B is a different state of the link hub.

FIGS. 32A and 32B show a different configuration of a link hub, and correspond to FIGS. 22A and 22B. This configuration is different only in that not only the first link mechanism 4A but also the second link mechanism 4B is provided with the actuator 150B (152B). The rest of the configuration is the same as the configuration shown in FIGS. 22A and 22B and achieves the same function and effect, and therefore the detailed description thereof has been omitted.

Figure 33:
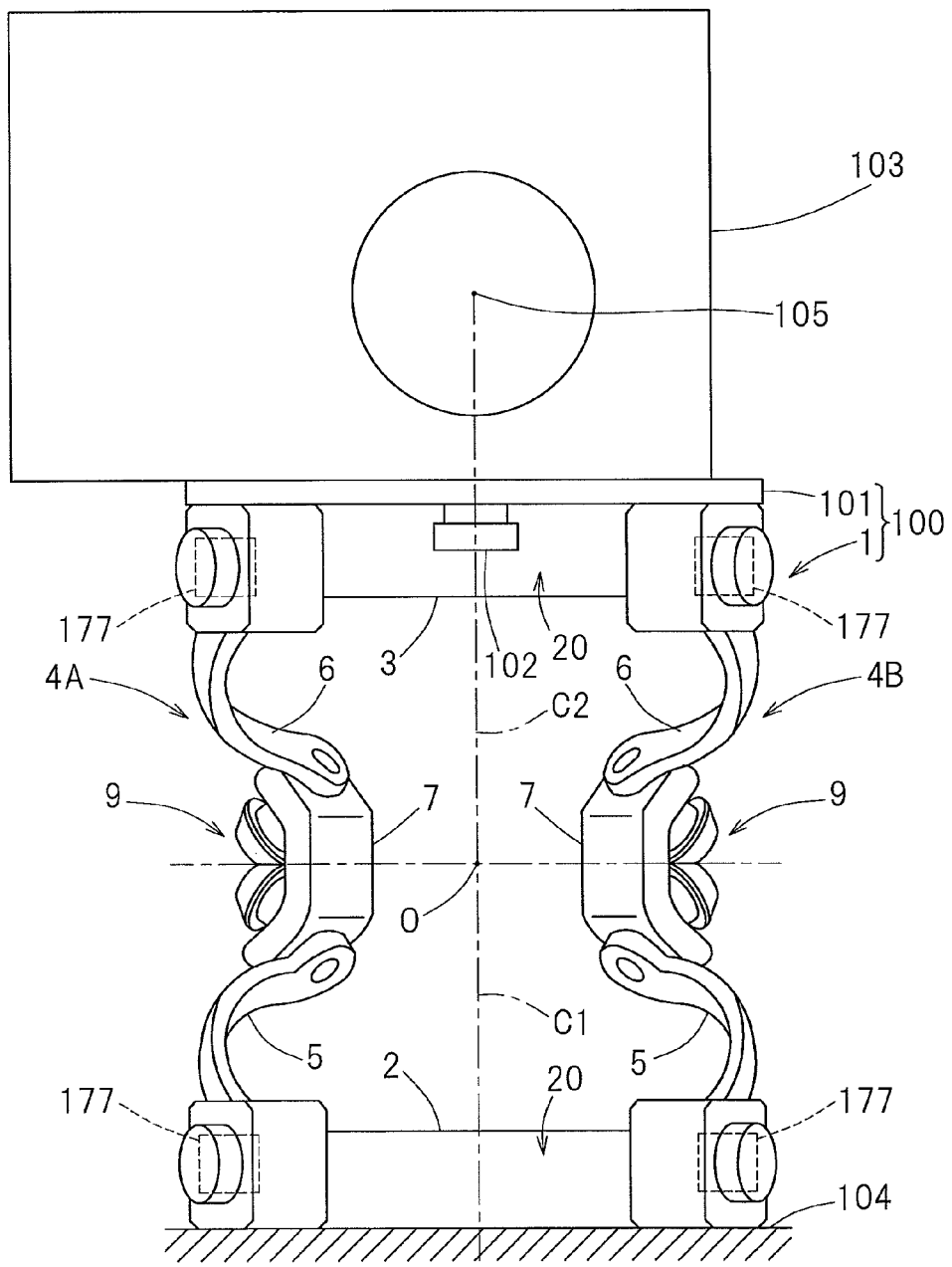
FIG. 33 is a front view showing a platform according to a fourteenth embodiment of the present invention.
Figure 34:
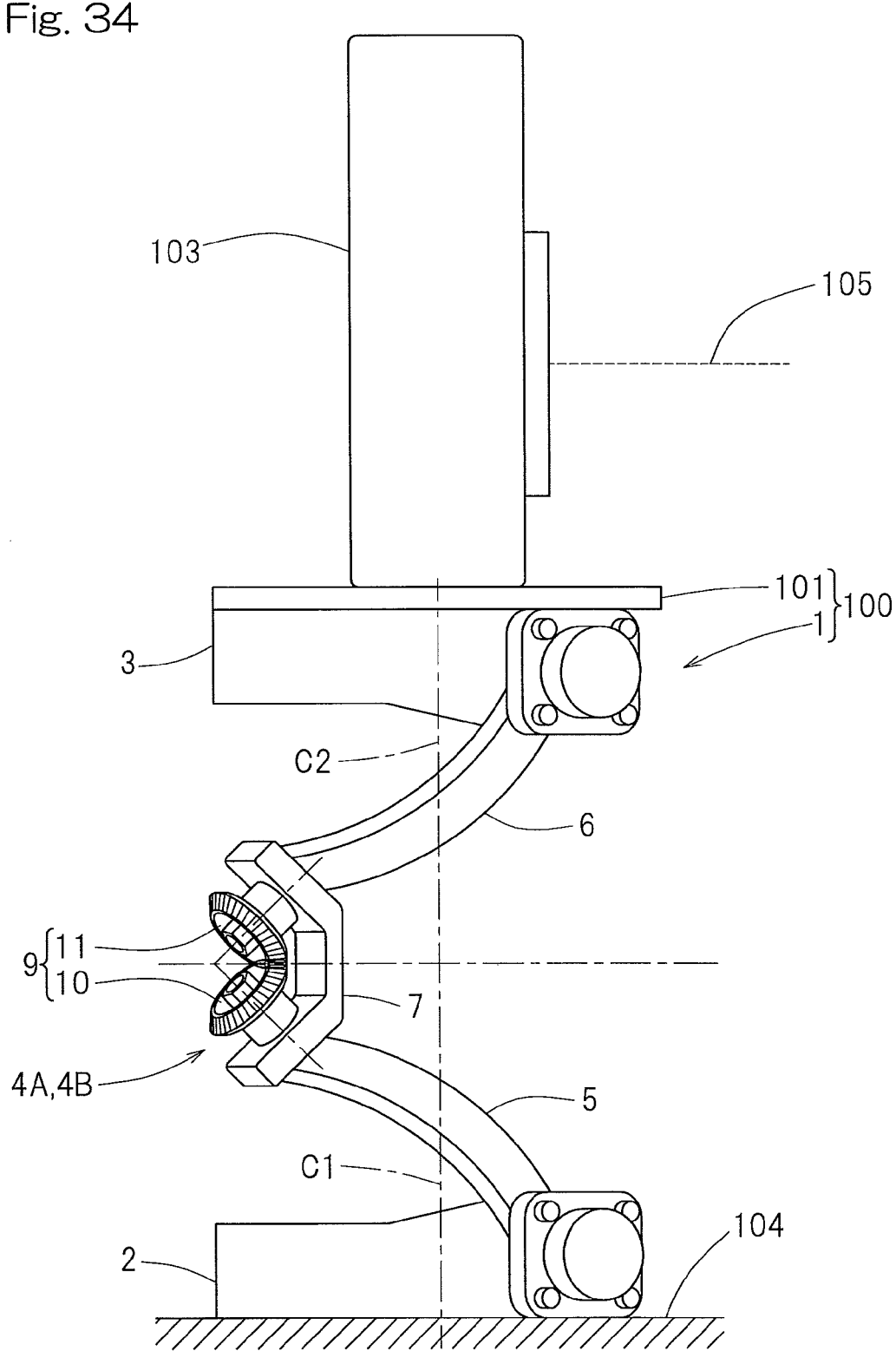
FIG. 34 is a side view showing a usage state of the platform.

A fourteenth embodiment of the present invention will be described with reference to FIGS. 33 to 36. FIGS. 33 and 34 are a front view and a side view showing a usage state of a platform 100 according to the fourteenth embodiment. The platform 100 includes any one of the above-described link actuating devices 1, and a device mount 101 is supported by the link actuating device 1 such that the attitude thereof can be changed. In FIG. 33, a camera as an optical device 103 is mounted to the device mount 101 with a mounting screw 102.

Figure 35:
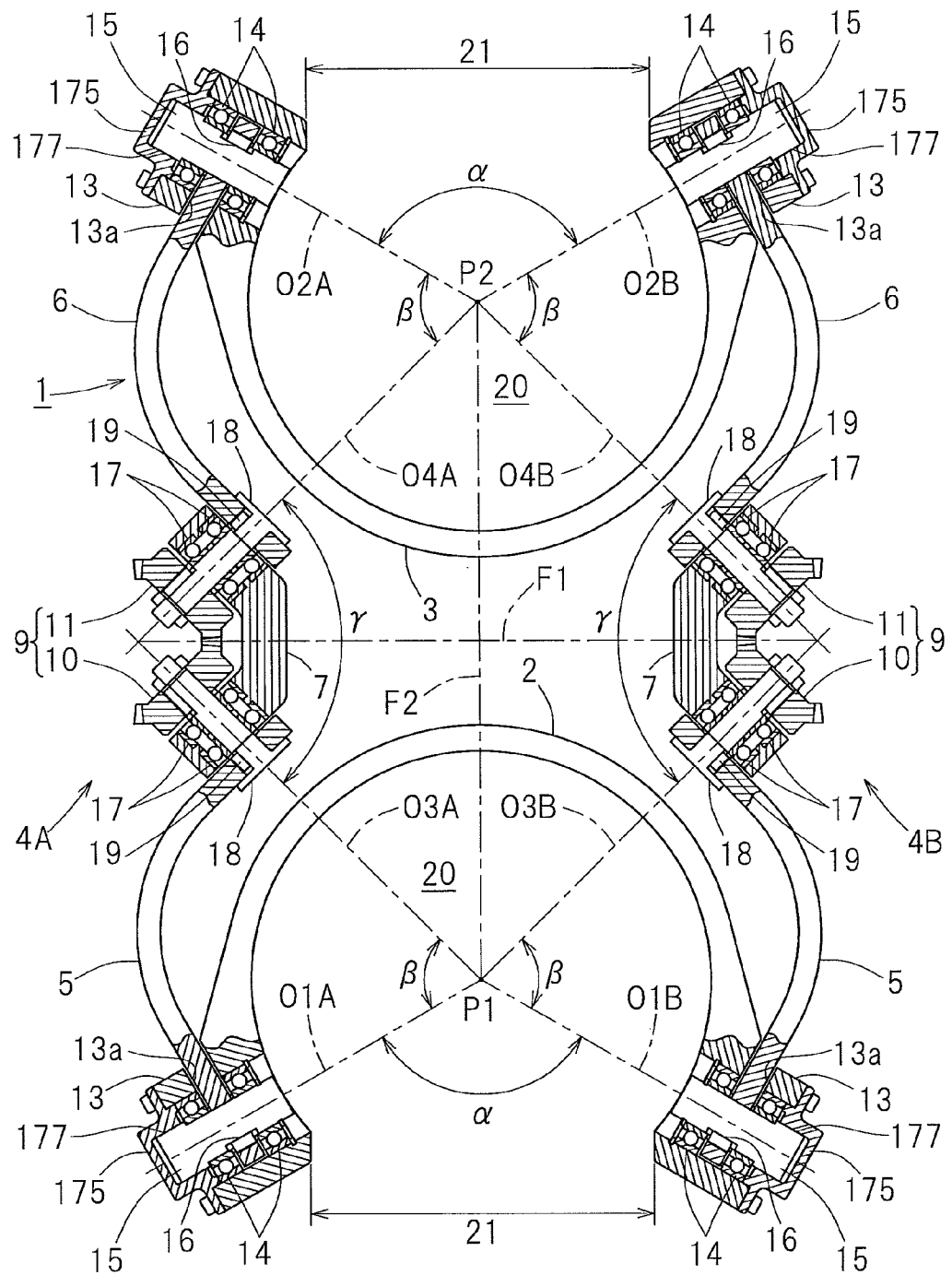
FIG. 35 is a partially broken plan view of the link actuating device in an exploded state.

The perspective view of the link actuating device 1 is the same as that shown in FIG. 1 of the first embodiment, and FIG. 35 is an exploded view of the link actuating device 1. The basic configuration of the link actuating device 1 is the same as that of the first embodiment, and therefore the detailed description thereof has been omitted.

As shown in FIG. 35, the inter-axis angle β between each of the first revolute pair axes O1A and O1B (second revolute pair axes O2A and O2B) of the input side link hub 2 (output side link hub 3) and the input side end link 5 (output side end link 6) and each of the third revolute pair axes O3A and O3B (fourth revolute pair axes O4A and O4B) between the input side end link 5 (output side end link 6) and the intermediate link 7 is 75°. Additionally, the inter-axis angle γ between each of the third revolute pair axes O3A and O3B between the input side end links or the proximal side end links 5 and the intermediate link 7 and each of the fourth revolute pair axes O4A and O4B between the output side end links or the distal side end links 6 and the intermediate link 7 is 90°. That is, the inter-axis angles α, β, and γ satisfy the relationship: $\alpha+2\beta+\gamma=360°$.

By defining the dimensions and the shape of each of the link mechanism components so as to satisfy the above-described relationship, it is possible to develop the link actuating device 1 on a single plane as shown in FIG. 35. The two sets of link mechanisms 4A and 4B are disposed at positions that are mirror symmetrical to each other with respect to the longitudinal cross section F2 passing through the spherical surface link centers P1 and P2 on the proximal end side and the distal end side and bisecting the inter-axis angle α between the respective first revolute pair axes O1A and O1B (second revolute pair axes O2A and O2B) between the input side link hub 2 (output side link hub 3) and the input side end link 5 (output side end link 6). Additionally, the inter-axis angle γ between the third and fourth revolute pair axes O3A and O4A (O3B and O4B) between the input side end link 5 (output side end link 6) and the intermediate link 7 can be arbitrarily set.

Two rolling bearings 14 are disposed with an axial gap, and the proximal end of the end link 5 or 6 is located in the gap portion. A groove 13a, to which the basal portion of the end link 5 or 6 is fitted, is formed in each bearing enclosing portion 13. By restricting the rotational range of the end links 5 and 6 with the groove 13a, the intermediate link 7 of each of the first and second link mechanisms 4A and 4B is always located on the side where the inter-axis angle between the respective first revolute pair axes O1A and O1B (second revolute pair axes O2A and O2B) is greater than 180° as described above.

Figure 36:
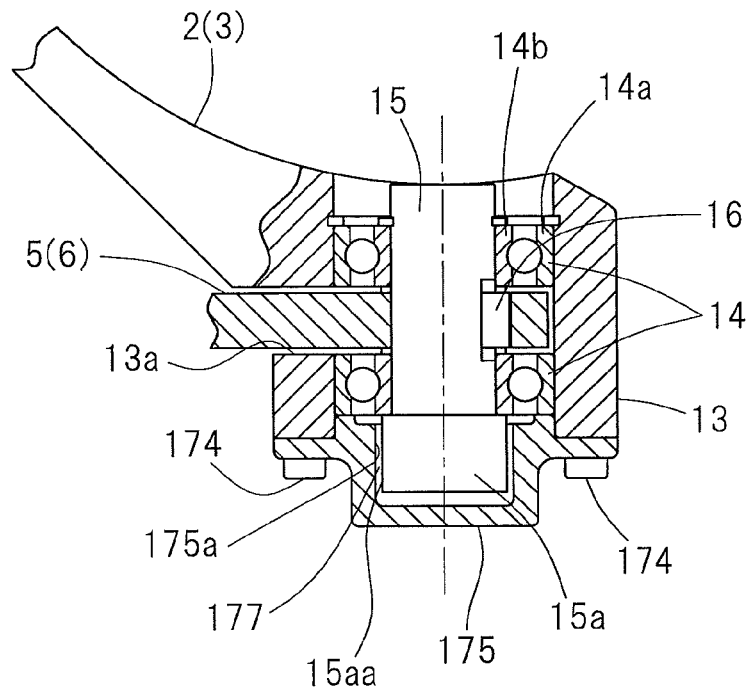
FIG. 36 is a partial enlarged view of FIG. 35.

FIG. 36 is a partial enlarged view of FIG. 35, and shows a revolute pair portion of an input side link hub or a proximal end side link hub 2 and an output side end link or a proximal side end link 5 of the link mechanism 4A. The other revolute pair portions between the link hubs 2 and 3 and the end links 5 and 6 have the same structure. An rolling bearing 14 is, for example, a ball bearing such as a deep groove ball bearing or an angular contact ball bearing, and includes an outer ring 14a fitted to the inner circumference of the bearing enclosing portion 13 by press-fitting or the like and an inner ring 14b fitted to the outer circumference of the rotational shaft (link hub connecting shaft) 15 by press-fitting or the like. Besides double row ball bearings as in the illustrated example, a roller bearing may be used as the rolling bearings 14. Alternatively, a sliding bearing may used in place of the rolling bearings 14.

A link hub flange 175 having a shape that covers an end face of the bearing enclosing portion 13 is fastened with a bolt 174 to the outer end of the bearing enclosing portion 13. The link hub flange 175 has a cylindrical inner circumferential face 175a that opposes a cylindrical outer circumferential face 15aa of an outer end large diameter portion 15a of a rotational shaft (intermediate link connecting shaft) 15 with a slight gap. The cylindrical inner circumferential face 175a of the link hub flange 175 and the cylindrical outer circumferential face 15aa of the rotational shaft (intermediate link connecting shaft) 15 define rotatable opposed portions that are rotatably displaced relative to each other. Also, high-viscosity grease 177 is sealed in the gap between the cylindrical inner circumferential face 175a and the cylindrical outer circumferential face 15aa. The relative rotation between the input side link hub 2 (output side link hub 3) and the input side end link 5 (output side end link 6) is limited by the viscous resistance of the grease 177. That is, the grease 177 defines rotation limiting unit that limits the relative rotation between the two link mechanism components.

Rolling bearings 17 are provided at opposite end portions of each of the intermediate links 7 in FIG. 35, and rotational shafts (link hub connecting shaft) 18 are rotatably supported by the rolling bearings 17. The rotational shafts (link hub connecting shafts) 18 are provided at the distal ends of the end links 5 and 6 via keys 19 so as to rotate together with the end links 5 and 6. The axes of the rotational shafts (intermediate link connecting shafts) 18 coincide with the third and fourth revolute pair axes O3 and O4. The rolling bearings 17 are, for example, ball bearings such as deep groove ball bearings or angular contact ball bearings. Besides double row ball bearings as in the illustrated example, roller bearings may be used as the rolling bearings 17. Alternatively, sliding bearings may be used in place of the rolling bearings 17.

Each of the hollow portions 20 is in communication with the outside of the link hub 2 or 3 via an opening 21 formed between the bearing enclosing portions 13. Each opening 21 is located on the same side with respect to the respective revolute pair axes O1A, O1B, O2A, and O2B for both of the proximal end side and distal end side link hubs 2 and 3. That is, in an attitude in which the proximal end side link hub 2 and the distal end side link hub 3 are parallel to each other as shown in FIGS. 33 and 34, the openings 21 of the two link hubs 2 and 3 face the same side.

By provision of the interlocking unit 9, the link actuating device 1 can define the attitude of the distal end side link hub 3 relative to the proximal end side link hub 2 even if the number of sets of the link mechanisms 4A and 4B is two. Since the number of sets of the link mechanisms 4A and 4B is two, which is fewer than conventionally used three sets of link mechanisms, the interference between the first and second link mechanisms 4A and 4B can be more easily prevented and thus an increased degree of freedom in design is achieved. This enables the link actuating device 1 to have a compact configuration with a small overall outer diameter. Furthermore, it is possible to achieve cost reduction due to the smaller number of the first and second link mechanisms 4A and 4B.

The platform 100 has the above-described configuration, in which an optical device 103 is mounted to a device mount 101 and the proximal end side link hub 2 of the link actuating device 1 is directly placed on a placement stage 104 such as a desk, which is a fixed installation object, as shown in FIGS. 33 and 34. Assuming that the upper face of the placement stage 104 is inclined with respect to the horizontal, an optical axis 105 of the optical device 103 is inclined with respect to the horizontal in a state in which the proximal end side link hub 2 and the distal end side link hub 3 of the link actuating device 1 are parallel to each other. By actuating the link actuating device 1 by manual operation from the state shown in the drawing so as to change the attitude of the distal end side link hub 3 relative to the proximal end side link hub 2, the optical axis 105 is positioned in the tilt direction (the vertical rotational direction and the vertical inclination direction) and the horizontal inclination direction. When the optical device 103 is mounted to the device mount 101 such that the distal end side link hub central axis C2 and the optical axis 105 cross each other as shown in the drawing, the optical axis 105 can be easily positioned horizontally.

High-viscosity grease 177 is sealed as the rotation limiting unit between the rotatable opposed portions of the revolute pair portions between the link hubs 2 and 3 and the end links 5 and 6, or in other words, between the cylindrical inner circumferential face 175a of the link hub flange 175 and the cylindrical outer circumferential face 15aa of the rotational shaft (link hub connecting shaft) 15. Therefore, the relative rotation between the link hubs 2 and 3 and the end links 5 and 6 is permitted, and at the same time, the relative rotation between the link hubs 2 and 3 and the end links 5 and 6 is limited. Accordingly, it is possible to hold the distal end side link hub 3 in any attitude relative to the proximal end side link hub 2, and also fix the optical axis 105 of the optical device 103 in any orientation. Furthermore, rattling between the link hubs 2 and 3 and the end links 5 and 6 is obviated owing to the viscous resistance of the grease 177, thereby preventing wobbling during the manual operation and improving operability. For example, in the case of performing video shooting by mounting a video camera as the optical device 103, it is possible to easily perform shooting without wobbling.

Figure 37:
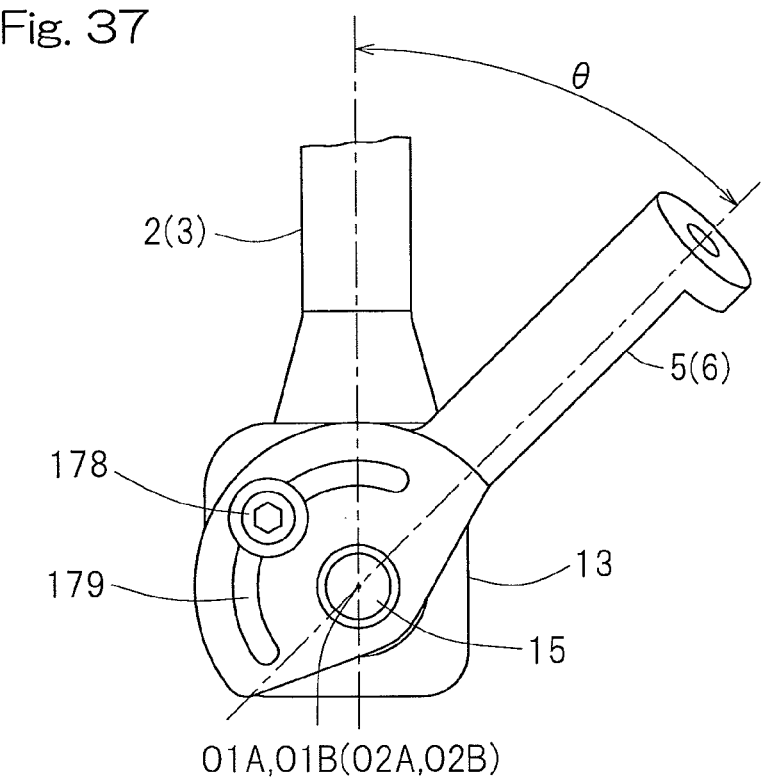
FIG. 37 is a diagram showing an exterior of a revolute pair portion between a link hub and an end link of a link actuating device in a platform according to a fifteenth embodiment.

FIG. 37 shows a fifteenth embodiment using different rotation limiting unit. The rotation limiting unit includes a bolt 178 screwed to the input side link hub 2 (output side link hub 3) through the input side end link 5 (output side end link 6), and limits the rotation of the input side end link 5 (output side end link 6) relative to the input side link hub 2 (output side link hub 3) by the frictional resistance between the head portion of the bolt 178 and the outer face of the input side end link 5 (output side end link 6). The bolt 178 is inserted through an arc-shaped hole 179 about the first revolute pair axis O1A or O1B (second revolute pair axis O2A or O2B) formed in the input side end link 5 (output side end link 6), and is configured to respond to the change in the rotational angle θ of the input side end link 5 (output side end link 6).

Figure 38:
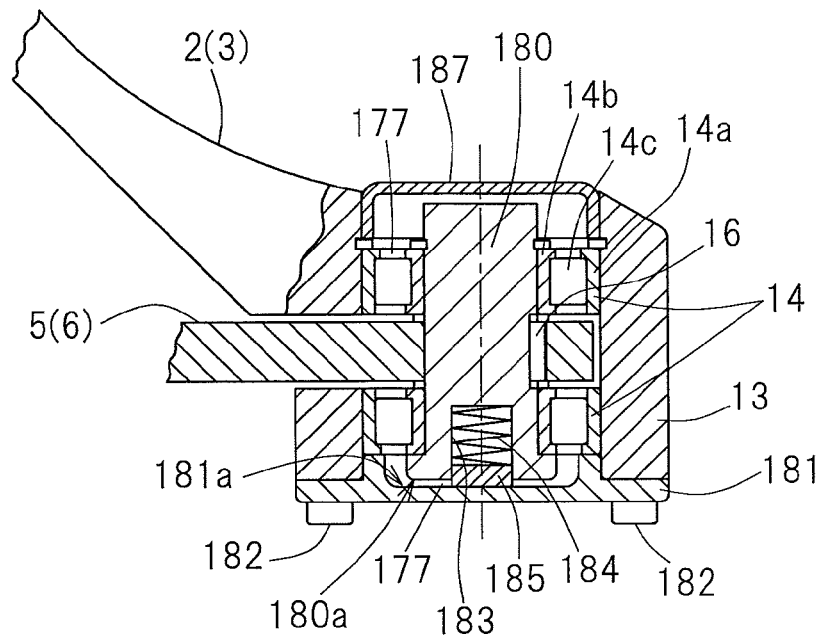
FIG. 38 is a vertical cross-sectional view of a revolute pair portion between a link hub and an end link of a link actuating device in a platform according to a sixteenth embodiment.

FIG. 38 shows a sixteenth embodiment using another different rotation limiting unit. In this rotation limiting unit, one of two link mechanism components includes a shaft member concentric with the revolute pair axis, and the other link mechanism component is used for a revolute pair portion having an opposed surface that opposes the end face of the shaft member contactlessly. FIG. 38 shows a revolute pair portion of the input side link hub 2 (output side link hub 3) and the input side end link 5 (output side end link 6). In this case, the shaft member is a link hub connecting shaft 180, and the opposed surface is an inner end face 181a of a link hub flange 181. The link hub connecting shaft 180 is rotatably supported on the bearing enclosing portion 13 by two rolling bearings 14. Additionally, the link hub flange 181 is fastened with bolts 182 to the outer end of the bearing enclosing portion 13 so as to close the end face of the bearing enclosing portion 13.

A recess 183 is formed in the outer end face of the link hub connecting shaft 180, and a pressing spring member 184 made of a compression coil spring is accommodated in the recess 183. Then, a contact element 185 is pressed against the inner end face 181a of the link hub flange 181 by the pressing spring member 184. The pressing spring member 184 and the contact element 185 constitute rotation limiting unit.

In this example, each rolling bearing 14 is a roller bearing whose rolling element 14c is a roller, with the outer ring 14a being fitted to the inner circumference of the bearing enclosing portion 13 by press-fitting or the like and the inner ring 14b being fitted to the outer circumference of the link hub connecting shaft 180 by press-fitting or the like. High-viscosity grease 177 is sealed inside the rolling bearing 14. The high-viscosity grease 177 is also sealed in the gap between the outer end face 180a of the link hub connecting shaft 180 and the inner end face 181a of the link hub flange 181. By closing both ends of the bearing enclosing portion 13 with the link hub flange 181 and a lid member 187 fitted to the inner end of the bearing enclosing portion 13, the grease 177 inside the rolling bearings 14 and the grease 177 between the outer end face 180a of the link hub connecting shaft 180 and the inner end face 181a of the link hub flange 181 are prevented from leaking from the bearing enclosing portion 13.

In the case of the rotation limiting unit, the relative rotation between the input side link hub 2 (output side link hub 3) and the input side end link 5 (output side end link 6) is limited by the friction between the inner end face 181a of the link hub flange 181 and the contact element 185. The relative rotation between the input side link hub 2 (output side link hub 3) and the input side end link 5 (output side end link 6) is also limited by the high-viscosity grease 177 provided between the outer end face 180a of the link hub connecting shaft 180 and the inner end face 181a of the link hub flange 181. In addition, with this configuration of the revolute pair portion, the grease 177 is sealed inside the rolling bearing 14, and therefore the starting torque at the time of operating the link actuating device 1 is reduced. Furthermore, the operation during the actuation is smooth, thus achieving good operability.

Although the rotation limiting unit in each of the embodiments described above is provided in the revolute pair portions between the link hubs 2 and 3 and the end links 5 and 6, the rotation limiting unit having this configuration may be provided in the revolute pair portions between the end links 5 and 6 and the intermediate link 7.

Figure 39:
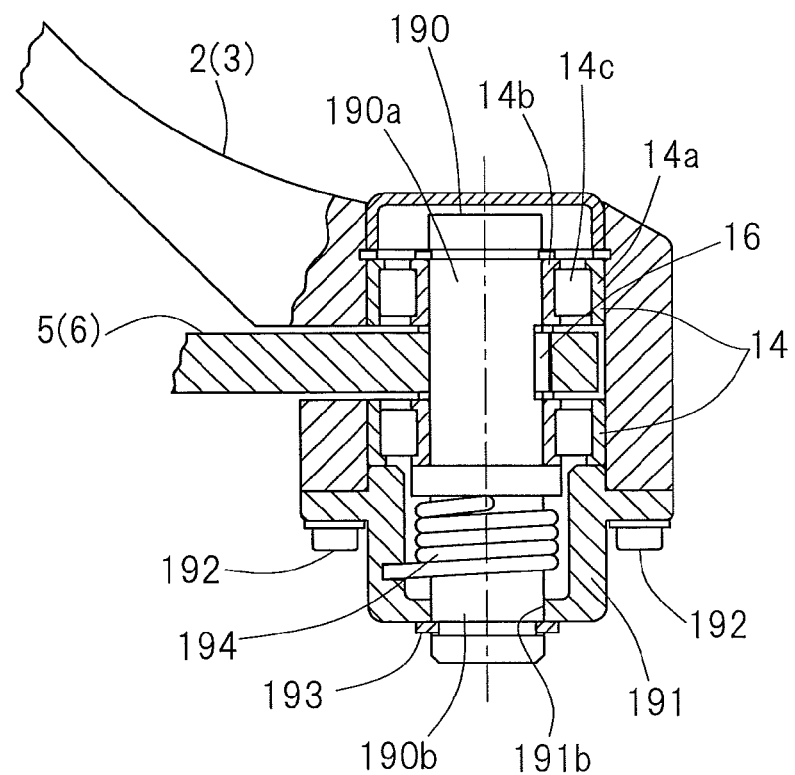
FIG. 39 is a vertical cross-sectional view of a revolute pair portion between a link hub and an end link of a link actuating device in a platform according to a seventeenth embodiment.
Figure 40:
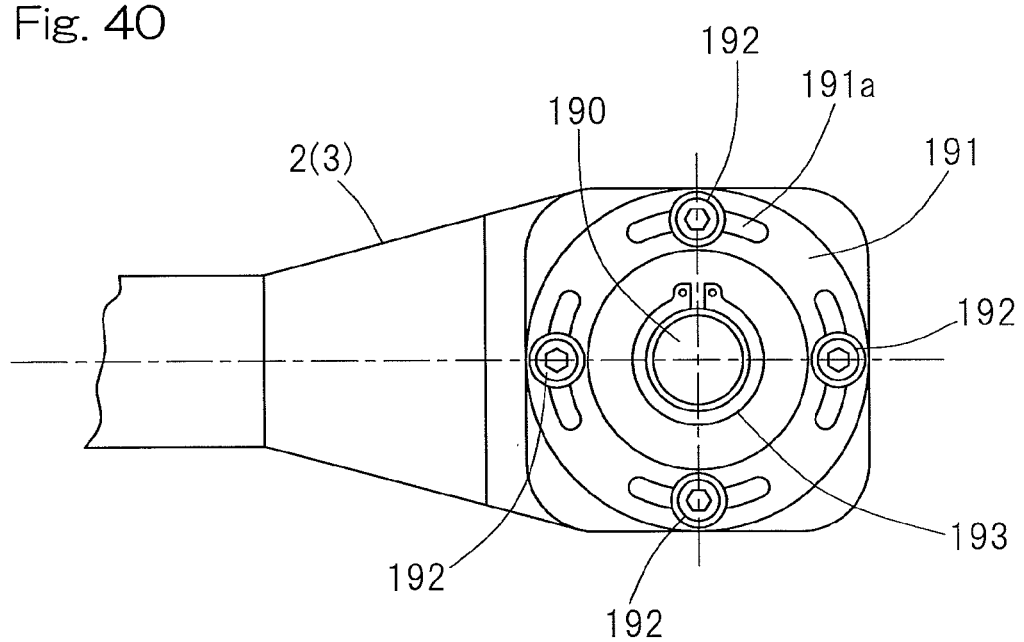
FIG. 40 is a diagram showing an exterior of the revolute pair portion.

FIGS. 39 and 40 show a seventeenth embodiment of a revolute pair portion between an input side link hub 2 (output side link hub 3) and an input side end link 5 (output side end link 6) having a different configuration. In the revolute pair portion as well, each rolling bearing 14 that rotatably supports a link hub connecting shaft 190 is a roller bearing, with the outer ring 14a being fitted to the inner circumference of the bearing enclosing portion 13 by press-fitting or the like and the inner ring 14b being fitted to the outer circumference of the link hub connecting shaft 190 by press-fitting or the like. A link hub flange 191 having the shape of a flanged cylinder is fastened with a plurality of bolts 192 to the outer end of the bearing enclosing portion 13. Bolt holes 191a of the link hub flange 191 are arc-shaped holes, which allow the attachment position of the link hub flange 191 to be adjusted in the circumferential direction.

The link hub connecting shaft 190 includes a spring guide portion 190b extending axially outward from a portion 190a fitted to the rolling bearings 14. The outer end of the spring guide portion 190b protrudes through an axial hole 191b of the link hub flange 191 to the outside, and the link hub connecting shaft 190 is axially positioned by a retaining ring 193 fitted to the protruding portion.

A biasing spring member 194 composed of a torsion spring is fitted around the outer circumference of the spring guide portion 190b, and one end of the biasing spring member 194 is fixed to the link hub connecting shaft 190 and the other end thereof is fixed to the link hub flange 191. The spring force of the biasing spring member 194 biases the input side link hub 2 (output side link hub 3) and the input side end link 5 (output side end link 6) that are the two link mechanism components so as to form a predetermined angle together. For example, even if the distal end side link hub 3 is inclined in either direction from the neutral state that is a state in which the proximal end side link hub 2 and the distal end side link hub 3 are parallel to each other as shown in FIGS. 33 and 34, the biasing spring member 194 biases the distal end side link hub 3 so as to return to the neutral state. The spring force of the biasing spring member 194 described above can be changed by adjusting the attachment position of the link hub flange 191 in the circumferential direction by loosening the bolts 192. That is, the link hub flange 191 and the bolts 192 define the spring force changing unit.

When the biasing spring member 194 is a torsion spring fitted around the outer circumference of the link hub connecting shaft 190 as described above, the biasing spring member 194 can be installed in compact manner. Although the biasing spring member 194 shown in FIG. 39 is a torsion coil spring, it may be a torsion spring that is not in the form of a coil.

By properly adjusting the angle between the input side link hub 2 (output side link hub 3) and the input side end link 5 (output side end link 6) by the spring force of the biasing spring member 194 such that the input side link hub 2 (output side link hub 3) and the input side end link 5 (output side end link 6) form a predetermined angle therebetween, the inclination of the distal end side link hub 3 due to the weight of the optical device 103 (FIGS. 33 and 34) mounted to the device mount 101 (FIGS. 33 and 34) is corrected. This makes it possible to reduce the moment acting on the revolute pair portions of the link actuating device 1. Since the spring force of the biasing spring member 194 can be changed, it is possible to reduce the moment acting on the revolute pair portions according to the change in weight balance resulting from the use of different optical devices 103.

Figure 41:
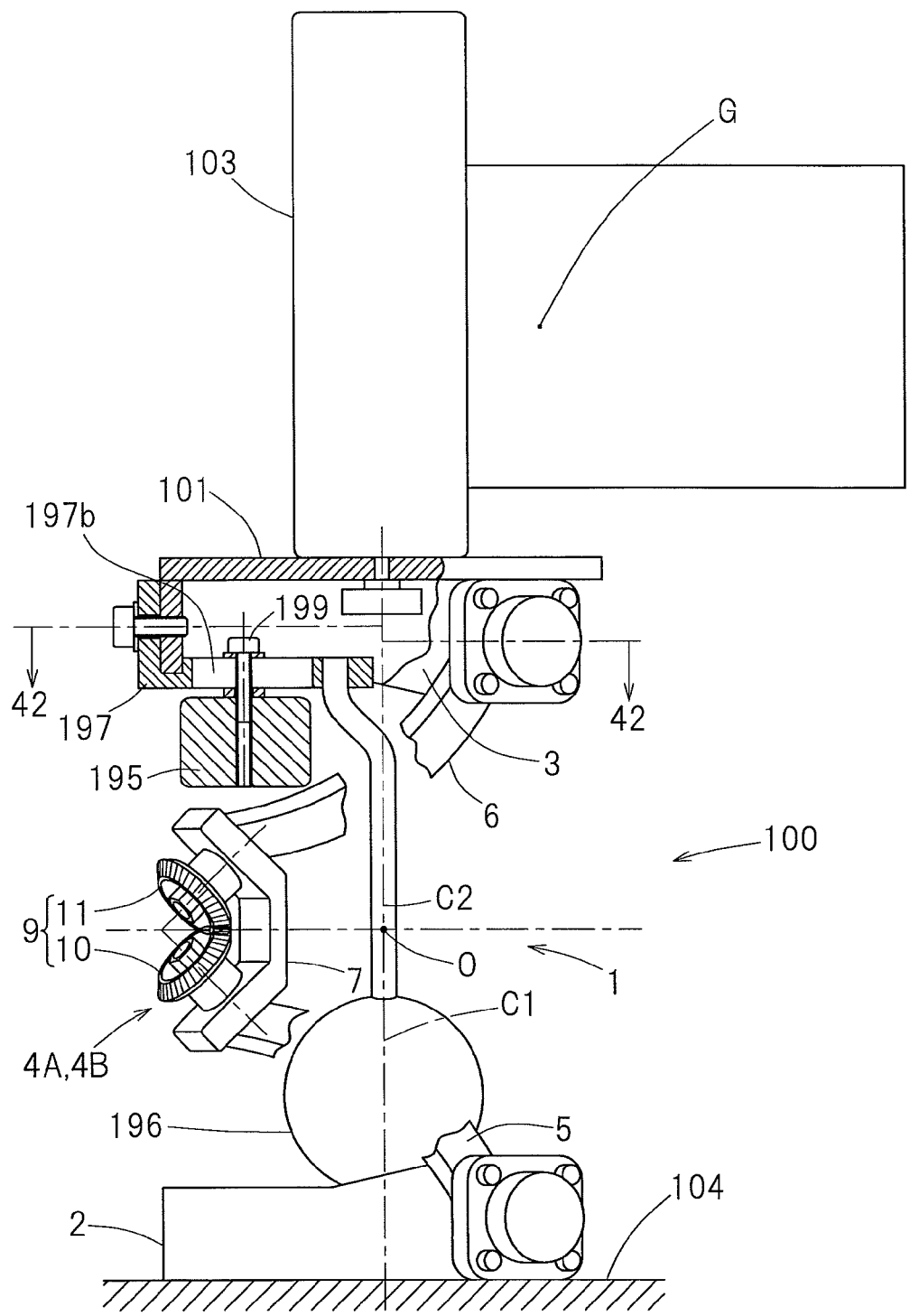
FIG. 41 is a side view showing a usage state of a platform according to eighteenth embodiment of the present invention.
Figure 42:
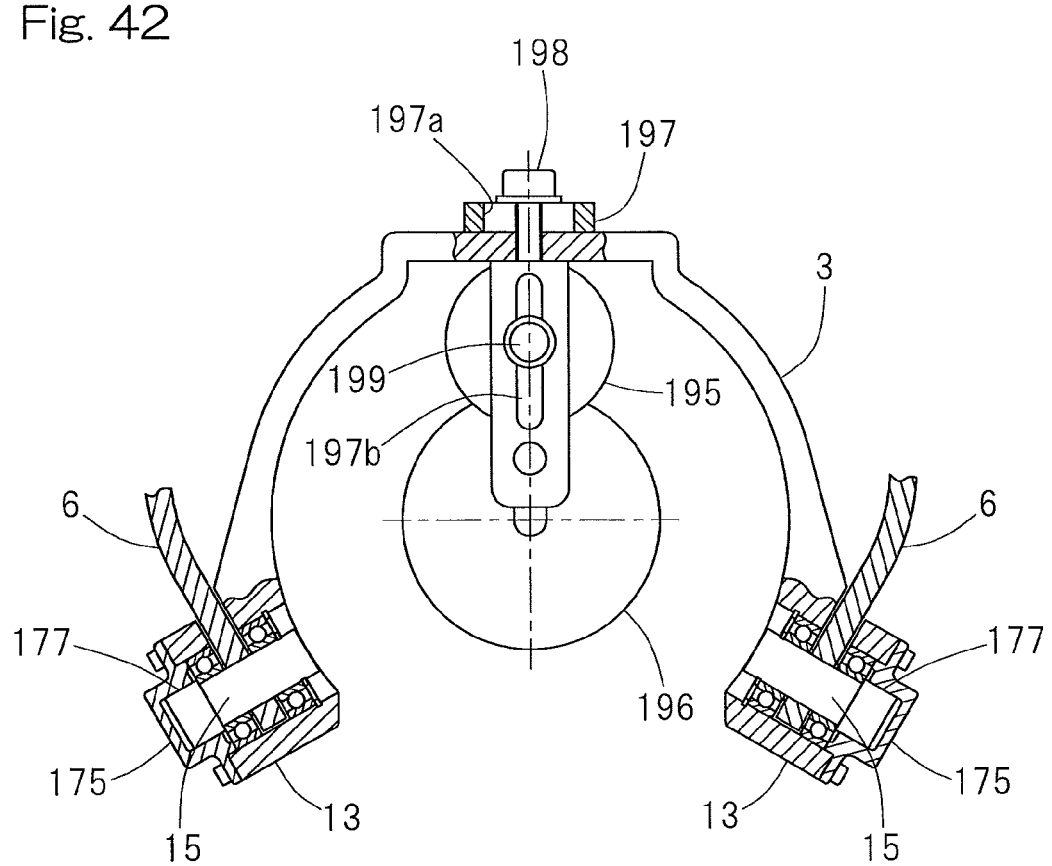
FIG. 42 is a cross-sectional view taken along the line 42-42 in FIG. 41.

FIG. 41 is a side view showing a usage state of a platform according to an eighteenth embodiment of the present invention. FIG. 42 is a cross-sectional view taken along the line 42-42 of FIG. 41. The platform 100 is installed on a placement stage 104 such as a desk, with an input side link hub central axis C1 on the proximal end side facing in the vertical direction, and includes a balance weight 195 that achieves a weight balance with the optical device 103 mounted to the device mount 101, and a counter weight 196 corresponding to the weight of the optical device 103.

Specifically, a weight mounting angle member 197 is fixed to the distal end side link hub 3, and the balance weight 195 and the counter weight 196 are mounted to the weight mounting angle member 197 in a suspended state. The suspension position of the balance weight 195 is on the side opposite to a center of gravity G of the optical device 103 across the output side link hub central axis C2 on the distal end side. The counter weight 196 is located on the output side link hub central axis C2 on the distal end side and on the side opposite to the link center O, and has a weight corresponding to the amount of moment about the link center O of the optical device 103.

The weight mounting angle member 197 is fixed to the distal end side link hub 3 with a bolt 198 inserted through a slot 197a that is long in the right-left direction and is formed in the weight mounting angle member 197. The fixation position of the weight mounting angle member 197 is adjustable in the right-left direction along the slot 197a. The balance weight 195 is suspended by hooking, onto the upper surface of the weight mounting angle member 197, the head portion of a bolt 199 inserted through a slot 197b that is long in the front-back direction and is formed in the weight mounting angle member 197. The suspension position of the balance weight 195 is adjustable in the front-back direction along the slot 197b.

With the provision of the balance weight 195, it is possible to reduce the moment acting on the revolute pair portions of the link actuating device 1 due to the weight of the movable portion of the platform 100 and the weight of the optical device 103. This makes it possible to reduce the load on the rotation limiting unit (e.g., the grease 177), thus simplifying the configuration of the rotation limiting unit. Since the fixation position of the weight mounting angle member 197 and the suspension position of the balance weight 195 are variable, it is possible to reduce the moment acting on the revolute pair portions of the link actuating device 1 according to the change in weight balance resulting from the use of different optical devices 103. Furthermore, with the provision of the counter weight 196, it is possible to reduce the moment acting on the revolute pair portions even if the weight balance is changed as a result of the operation of the link actuating device 1.

Although the balance weight 195 is provided in the weight mounting angle member 197 fixed to the distal end side link hub 3 in the present embodiment, the balance weight 195 may be provided in any portion of the distal side end link 6, the intermediate link 7, and the proximal side end link 5 so long as it is possible to achieve a weight balance with the weights of the platform 100 and the optical device 103.

Figure 43:
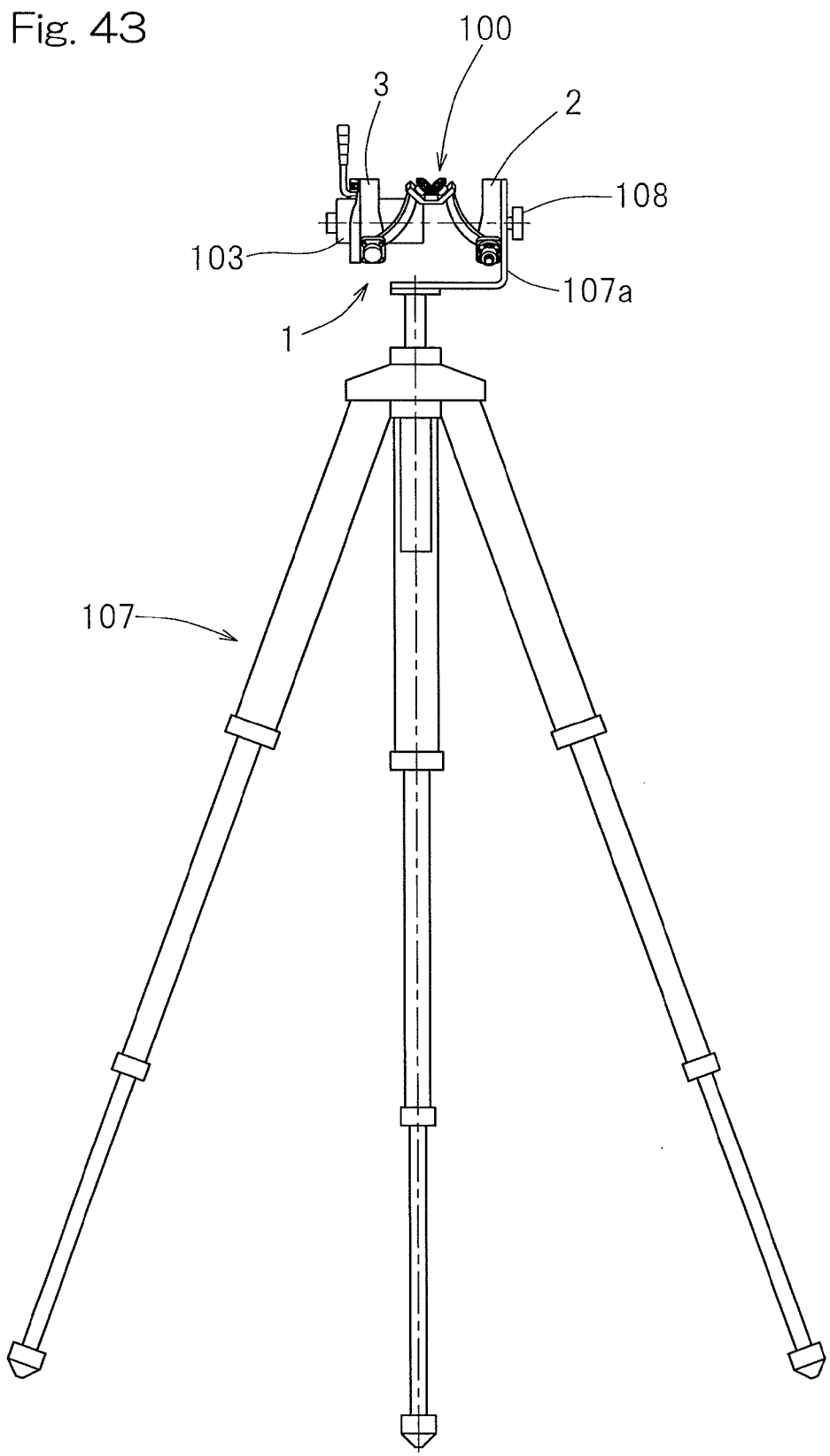
FIG. 43 is a side view showing a usage state of a platform according to a nineteenth embodiment of the present invention.
Figure 44:
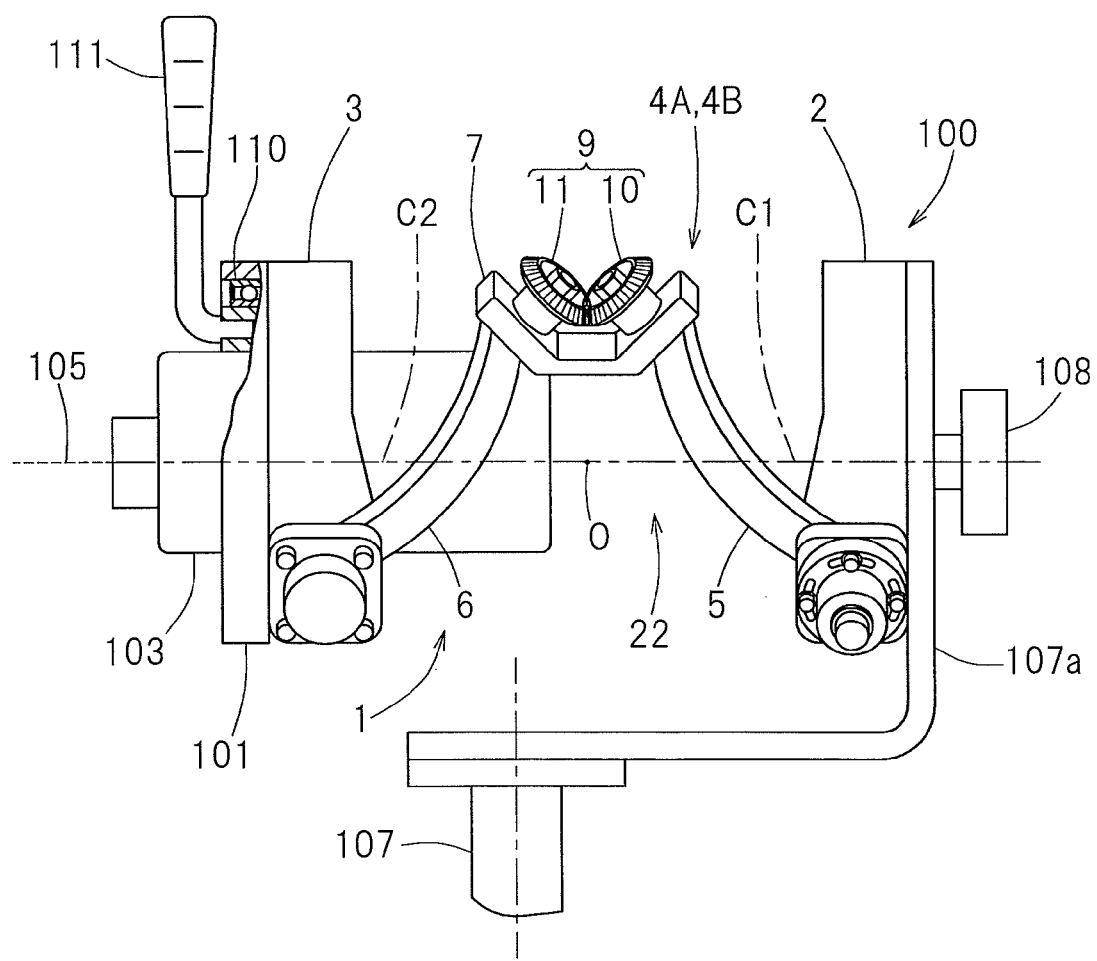
FIG. 44 is an enlarged view of the platform.
Figure 45:
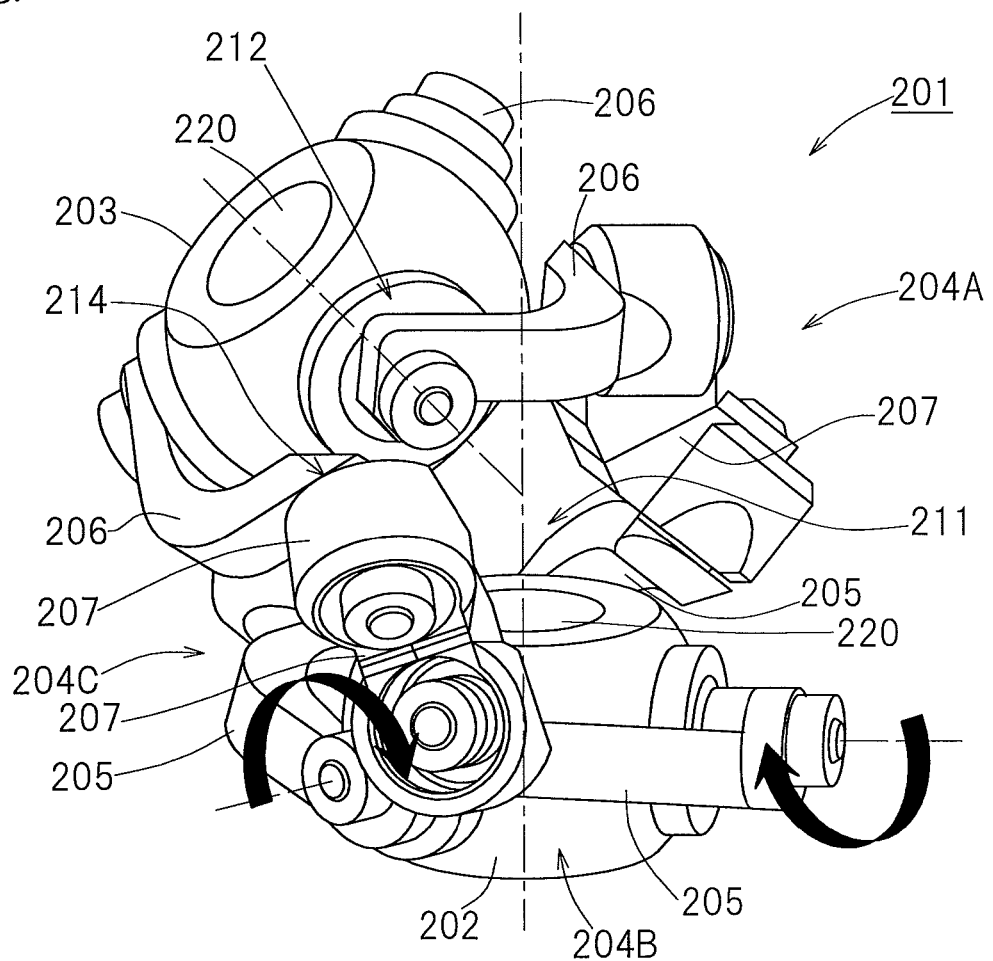
FIG. 45 is a perspective view of a conventional link actuating device.

FIG. 43 is a side view showing a usage state of a platform according to a nineteenth embodiment of the present invention. FIG. 44 is an enlarged view of the platform. The platform 100 is used by being mounted to a tripod 107 serving as the fixed installation object, and the proximal end side link hub 2 of the link actuating device 1 is mounted with a mounting screw 108 to an L-shaped mount 107a of the tripod 107. As shown in FIG. 44, in the mounted state, the input side link hub central axis C1 on the proximal end side is horizontal.

The device mount 101 is provided at the distal end side link hub 3 via a bearing 110 so as to be rotatable about the output side link hub central axis C2. The device mount 101 is provided with a lever 111 for rotation operation. As illustrated, the optical device 103 is mounted to the device mount 101 such that an optical axis 105 coincides with the output side link hub central axis C2 on the distal end side. In the illustrated example, the optical device 103 is mounted such that it passes through the hollow portion 20 (FIG. 35) of the distal end side link hub 3 and a portion thereof fits in a space portion 22 between the two sets of link mechanisms 4A and 4B. Accordingly, the optical device 103 can be mounted in a compact manner.

When the optical device 103 is installed so as to be rotatable about the output side link hub central axis C2 in this way, the positioning of the optical axis 105 in the tilt direction (vertical rotational direction) and the pan direction (horizontal rotational direction) can be performed by the operation of positioning the distal end side link hub 3 relative to the proximal end side link hub 2 of the link actuating device 1. Accordingly, the optical axis 105 can be linearly moved at the time of positioning the optical axis 105, thus speeding up the operation. Moreover, in the case of adjusting, for example, the inclination of an image of the optical device 103 by using the revolute pair about the central axis C2 of the distal end side link hub 3, the adjustment operation can be easily performed since the center of the image and the center of rotation of the optical device 103 coincides or are close to each other.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . Link actuating device (Limb joint mounted apparatus)
2 . . . Input side link hub (Proximal end side link hub)
3 . . . Output side link hub (Distal end side link hub)
4, 4A, 4B . . . Link mechanism
5 . . . Input side end link (Proximal side end link)
6 . . . Output side end link (Distal side end link)
7 . . . Intermediate link
9 . . . Interlocking unit
10, 11 . . . Bevel gear
13 . . . Bearing enclosing portion
14 . . . Rolling bearing
14a . . . Outer ring
20 . . . Hollow portion
21 . . . Opening portion
22A to 22D . . . Actuator
23A, 23B . . . Actuator
30 . . . Linear actuator
33 . . . Screw shaft (Advancing or retracting shaft)
36 . . . Outer cylinder body
40 . . . Auxiliary link
100 . . . Platform
101 . . . Device mount
103 . . . Optical device
150A, 150B, 152A, 152B . . . Actuator
151 . . . Controller
160 . . . limiter
167 . . . Damper
170, 171 . . . Coupling portion
177 . . . Rotation limiting unit (Grease)
184 . . . Pressing spring member
185 . . . Contact element
195 . . . Balance weight
196 . . . Counter weight
O1A, O1B . . . First revolute pair axis between input side link hub and input side end link
O2A, O2B . . . Second revolute pair axis between output side link hub and output side end link
O3 . . . Third revolute pair axis between input side end link and intermediate link
O4 . . . Fourth revolute pair axis between output side end link and intermediate link
P1 . . . Input side spherical surface link center
P2 . . . Output side spherical surface link center

What is claimed is:
1. A link actuating device comprising:
input side and output side link hubs;

input side and output side end links to be rotatably connected to the input side and output side link hubs, respectively;

an intermediate link to be rotatably connected to the input side and output side end links; and two sets of a three-link-chain link mechanism, each three-link-chain mechanism including four revolute pairs composed of the input side end link, the intermediate link and the output side end link, wherein each of the four revolute pairs have a first revolute pair axis between the input side link hub and the input side end link, a second revolute pair axis between the output side link hub and the output side end link, a third revolute pair axis between the input side end link and the intermediate link, a fourth revolute pair axis between the output side end link and the intermediate link;

the two sets of link mechanisms have a positional relationship in which, on both the input side and the output side, the respective first revolute pair axes of the two sets of link mechanisms are located on the same plane and cross each other; and at least one of the two sets of link mechanisms is provided with an interlocking unit to interlock the input side end link and the output side end link to each other so as to be rotationally displaced, wherein the intermediate link of each of the two sets of link mechanisms is located on a side on which an angle between the first revolute pair axes of the two link mechanisms is greater than 180°.

2. The link actuating device according to claim 1, wherein the interlocking unit interlocks the input side end link and the output side end link such that rotational directions thereof relative to the intermediate link are opposite to each other and rotational displacement angles thereof are the same.

3. The link actuating device according to claim 1, wherein geometric models obtained by respectively representing the two sets of link mechanisms by straight lines have the same shape.

4. The link actuating device according to claim 1, wherein geometric models obtained by respectively representing the two sets of link mechanisms by straight lines have shapes in which an input side portion and an output side portion relative to a central portion of the intermediate link are mirror symmetrical to each other.

5. The link actuating device according to claim 1, further comprising rolling bearings that rotatably support the input side and output side end links relative to the input side and output side link hubs, respectively, wherein each of the input side and output side link hubs is provided with a bearing enclosing portion enclosing an outer ring of the corresponding rolling bearing.

6. A link actuating device comprising:

input side and output side link hubs;

input side and output side end links to be rotatably connected to the input side and output side link hubs, respectively;

an intermediate link to be rotatably connected to the input side and output side end links; and two sets of a three-link-chain link mechanism, each three-link-chain mechanism including four revolute pairs composed of the input side end link, the intermediate link and the output side end link, wherein each of the four revolute pairs have a first revolute pair axis between the input side link hub and the input side end link, a second revolute pair axis between the output side link hub and the output side end link, a third revolute pair axis between the input side end link and the intermediate link, a fourth revolute pair axis between the output side end link and the intermediate link;

the two sets of link mechanisms have a positional relationship in which, on both the input side and the output side, the respective first revolute pair axes of the two sets of link mechanisms are located on the same plane and cross each other; and at least one of the two sets of link mechanisms is provided with an interlocking unit to interlock the input side end link and the output side end link to each other so as to be rotationally displaced, wherein the input side and output side link hubs respectively include input side and output side hollow portions each of which penetrates through in a direction parallel to an axis connecting input side and output side link hub centers, the input side and output side link hub centers being a point of intersection between the first revolute pair axes of the two link mechanisms and a point of intersection between the second revolute pair axes of the two link mechanisms, respectively in a state in which the input side and output side link hubs are parallel to each other, the input side and output side hollow portions have a shape in communication with outside of the respective input side and output side link hubs via input side and output side opening portions, the input side opening portion being provided between the first revolute pair axes of the two link mechanisms, the output side opening portion being provided between the second revolute pair axes of the two link mechanisms, and the input side and output side opening portions are located on the same side with respect to the first and second revolute pair axes, respectively.

7. The link actuating device according to claim 1, wherein the interlocking unit is configured to interlock the input side and output side end links to each other so as to be rotationally displaced by meshing between a gear provided in the input side end link and a gear provided in the output side end link.

8. The link actuating device according to claim 1, wherein each of the two sets of link mechanisms is provided with an actuator capable of arbitrarily changing a rotational angle of one of the four revolute pairs.

9. The link actuating device according to claim 1, wherein each of the two sets of link mechanisms is provided with an extendable linear actuator whose opposite ends are connected directly or indirectly to two link mechanism components that include the input side and output side end links or the input side and output side link hubs.

10. The link actuating device according to claim 9, wherein the opposite ends of the extendable linear actuator are directly or indirectly connected to the input side or output side link hub and the input side or output side end link connected to the corresponding link hub.

11. The link actuating device according to claim 9, wherein the extendable linear actuator includes an outer cylinder body and an advancing or retracting shaft that is located inside the outer cylinder body and advances or retracts relative to the outer cylinder body, and the outer cylinder body is fixed to the input side or output side link hub and the advancing or retracting shaft is connected to the input side or output side end link via an auxiliary link that adjusts a positional relationship between the advancing or retracting shaft and the input side or output side end link in response to advancement or retraction of the advancing or retracting shaft.

12. The link actuating device according to claim 9, wherein the opposite ends of the extendable linear actuator are directly or indirectly connected to the input side or output side link hub and the intermediate link.

13. The link actuating device according to claim 9, wherein the opposite ends of the linear actuator are directly or indirectly connected to the input side end link and the output side end link.

14. The link actuating device according to claim 1, wherein one of the two sets of link mechanisms is provided with two or more actuators that are capable of arbitrarily changing rotational angles of the revolute pairs or that change a relative distance between two of a plurality of link mechanism components that include the input side and output side end links or the input side and output side link hubs.

15. The link actuating device according to claim 14, wherein the two or more actuators comprises:
   a first actuator that changes a rotational angle of the first or second revolute pair; and
   a second actuator that changes a rotational angle of the third or fourth revolute pair.

16. The link actuating device according to claim 14, wherein the two or more actuators comprises:
   a first actuator that changes a rotational angle of the first or second revolute pair; and
   a third actuator that changes a relative distance between the input side or output side link hub and the intermediate link.

17. The link actuating device according to claim 14, wherein the two or more actuators comprises:
   a first actuator that changes a rotational angle of the first or second revolute pair; and
   a fourth actuator that changes a relative distance between the input side and output side end links.

18. A limb joint portion mounted apparatus comprising the link actuating device according to claim 1, wherein the input side and output side link hubs respectively include input side and output side hollow portions each of which penetrates through in a direction parallel to an axis connecting input side and output side link hub centers, the input side and output side link hub centers being a point of intersection between the first revolute pair axes of the two link mechanisms and a point of intersection between the second revolute pair axes of the two link mechanisms, respectively in a state in which the input side and output side link hubs are parallel to each other, and
   in a state in which a limb joint portion is located between the input side and output side link hubs and an area continuous with the limb joint portion is inserted in the input side and the output side hollow portion, the limb joint portion mounted apparatus is mounted around the limb joint portion.

19. The limb joint portion mounted apparatus according to claim 18, wherein the interlocking unit interlocks the input side end link and the output side end link such that rotational directions thereof relative to the intermediate link are opposite to each other and rotational displacement angles thereof are the same.

20. The limb joint portion mounted apparatus according to claim 18, wherein the input side and output side link hubs are each divided into two link hub halves arranged in a circumferential direction along an outer circumference of the hollow portion, and the end link of one of the two sets of link mechanisms is rotatably connected to each of the two link hub halves so as to permit the two link hub halves to be coupled to each other by the coupling portion.

21. The limb joint portion mounted apparatus according to claim 20, wherein one of coupling portions that are provided in two locations in the circumferential direction and that couple the two link hub halves to each other is configured to have a hinge structure that pivotably couples the two link hub halves to each other.

22. The limb joint portion mounted apparatus according to claim 18, wherein at least one of the four revolute pairs in each of the link mechanisms is provided with a limiter that limits relative rotation angular displacement of the at least one of the four revolute pairs.

23. The limb joint portion mounted apparatus according to claim 18, wherein at least one of the four revolute pairs in each of the link mechanisms is provided with a damper that elastically limits relative rotation angular displacement of the at least one of the four revolute pairs.

24. The limb joint portion mounted apparatus according to claim 18, wherein each of the two sets of link mechanisms is provided with an actuator that permits relative rotation angular displacement of at least one of the four revolute pairs to be changed, and a controller that controls the actuator such that the limb joint portion is moved within a movable range is provided.

25. The limb joint portion mounted apparatus according to claim 18, wherein each of the two sets of link mechanisms is provided with an actuator that permits relative rotation angular displacement of at least one of the four revolute pairs to be changed, and a controller that controls the actuator so as to assist movement of the limb joint portion within a movable range is provided.

26. A platform comprising:
   a device mount to which an optical device is mounted; and
   the link actuating device according to claim 1 that supports the device mount such that an attitude of the device mount is changed,
   wherein for each of the two sets of link mechanisms, at least one of the four revolute pairs is provided with a rotation limiting unit that limits relative rotation between the two link mechanism components constituting the at least one of the four revolute pairs.

27. The platform according to claim 26, wherein the rotation limiting unit is grease that is sealed between rotatable opposed portions of the two link mechanism components that are opposed each other and are rotatably displaced relative to each other.

28. The platform according to claim 27, wherein the two link mechanism components are rotatably connected each other via a rolling bearing at a location other than the rotatable opposed portions, and the grease is sealed inside the rolling bearing.

29. The platform according to claim 26, wherein one of the two link mechanism components includes a shaft member that is concentric with the revolute pair axis,
   the other link mechanism component includes an opposed surface that opposes an end face of the shaft member contactlessly, and
   the rotation limiting unit includes a contact element in contact with the opposed surface and a pressing spring member that is provided between the end face of the shaft member and the opposed surface and presses the contact element against the opposed surface.

30. The platform according to claim 26, wherein the proximal end side link hub is installed with a central axis thereof facing in a vertical direction, and at least one of the proximal side end link, the intermediate link, the distal side end link and the distal end side link hub is provided with a balance weight that achieves a weight balance among the link actuating device, the device mount, and the optical device mounted to the device mount.

31. The platform according to claim 26, wherein when an axis connecting link hub centers is termed as a link hub central axis, each of the link hub centers being a point of intersection between respective first or second the revolute pair axes of the proximal end side and distal end side link hubs in a state in which the proximal end side and distal end side link hubs are parallel to each other, the proximal end side link hub is installed such that the link hub central axis thereof faces in a vertical direction, and a counter weight, which corresponds to an amount of moment around a link center of the optical device and is mounted to the device mount, is provided on a side opposite to a side of the optical device with respect to the link center.

32. The platform according to claim 26, further comprising a biasing spring member provided between the two link mechanism components of the three-link-chain link mechanism including the four revolute pairs, the biasing spring member biasing the two link mechanism components so as to form a predetermined angle together.

33. The platform according to claim 32, wherein the biasing spring member is a torsion spring that is provided around the revolute pair axis between the two link mechanism components, one end of the torsion spring being fixed to one of the two link mechanism components and the other end thereof being fixed to the other of the link mechanism component.

34. The platform according to claim 26, wherein when $\alpha$ represents an angle between the first or second revolute pair axes of the first and second link mechanisms, $\beta$ represents an inter-axis angle between the first and third revolute pair axes or an inter-axis angle between the second and fourth revolute pair axes, and $\gamma$ represents an inter-axis angle between the third and fourth revolute pair axes, $\alpha+2\beta+\gamma=360°$ is satisfied.

35. The platform according to claim 26, wherein when an axis connecting link hub centers is termed as a link hub central axis, each of the link hub centers being a point of intersection between respective first or second the revolute pair axes of the proximal end side and distal end side link hubs in a state in which the proximal end side and distal end side link hubs are parallel to each other, the proximal end side link hub and the fixed installation object are connected by a revolute pair that is rotatable about the proximal end side link hub central axis, or the distal end side link hub and the device mount are connected by a revolute pair that is rotatable about the distal end side link hub central axis.

36. The platform according to claim 26, wherein the optical device is mounted to the device mount such that the distal end side link hub central axis and an optical axis of the optical device coincide or extend parallel to each other.

37. The platform according to claim 26, wherein the optical device is mounted to the device mount such that at least a part of the optical device is disposed in a space portion between the two sets of link mechanisms.

* * * * *